(12) United States Patent
Van

(10) Patent No.: US 9,526,795 B2
(45) Date of Patent: Dec. 27, 2016

(54) N-BOC-DENDRIMERS AND THEIR CONJUGATES

(71) Applicant: Annam Biosciences, LLC, San Diego, CA (US)

(72) Inventor: Sang Van, San Diego, CA (US)

(73) Assignee: Annam Biosciences, LLC, San Diego, CA (US)

( * ) Notice: Subject to any disclaimer, the term of this patent is extended or adjusted under 35 U.S.C. 154(b) by 0 days.

(21) Appl. No.: 14/424,672

(22) PCT Filed: Aug. 27, 2013

(86) PCT No.: PCT/US2013/056909
§ 371 (c)(1),
(2) Date: Feb. 27, 2015

(87) PCT Pub. No.: WO2014/036037
PCT Pub. Date: Mar. 6, 2014

(65) Prior Publication Data
US 2015/0224206 A1     Aug. 13, 2015

Related U.S. Application Data

(60) Provisional application No. 61/815,879, filed on Apr. 25, 2013, provisional application No. 61/694,200, filed on Aug. 28, 2012.

(51) Int. Cl.
| | |
|---|---|
| *A01N 43/04* | (2006.01) |
| *A61K 31/70* | (2006.01) |
| *A61K 47/48* | (2006.01) |
| *A61K 49/12* | (2006.01) |
| *C08G 73/02* | (2006.01) |
| *C08G 83/00* | (2006.01) |
| *A61K 31/337* | (2006.01) |
| *A61K 31/4745* | (2006.01) |
| *A61K 31/519* | (2006.01) |
| *A61K 31/555* | (2006.01) |
| *A61K 31/704* | (2006.01) |

(52) U.S. Cl.
CPC ....... *A61K 47/48215* (2013.01); *A61K 31/337* (2013.01); *A61K 31/4745* (2013.01); *A61K 31/519* (2013.01); *A61K 31/555* (2013.01); *A61K 31/704* (2013.01); *A61K 47/48107* (2013.01); *A61K 47/48192* (2013.01); *A61K 49/124* (2013.01); *C08G 73/024* (2013.01); *C08G 73/028* (2013.01); *C08G 83/004* (2013.01)

(58) Field of Classification Search
None
See application file for complete search history.

(56) References Cited

FOREIGN PATENT DOCUMENTS

WO    WO 2011/059609    5/2011

OTHER PUBLICATIONS

Aldersley, Simon James (2002) Synthesis and characterization of aliphatic hyperbranched polyamidoamines and polyamides. Doctoral thesis, Durham University.*
Tao et al. Chem. Commun. (2007), pp. 3441-3443.*
Chapman et al. J. Am. Chem. Soc. (1994), vol. 116, pp. 11195-11196.*
Wu et al. Chem. Commun. (2005), pp. 5775-5777.*
Zeng et al., "Dendrimers in Supra molecular Chemistry From Molecular Recognition to Self-Assembly" Chem. Rev. (1997) 97(5):1681-1712.
International Search Report and Written Opinion mailed Jan. 7, 2014 for PCT Application No. PCT/US2013/056909, filed Aug. 27, 2013.

* cited by examiner

*Primary Examiner* — Patrick Lewis
(74) *Attorney, Agent, or Firm* — Knobbe, Martens, Olson & Bear, LLP

(57) ABSTRACT

Asymmetrical dendritic compound of the Formula (I) as described herein can contain multiple functional moieties as represented by $R^1$ and $R^2$ in Formula (I). In various embodiments, the functional moieties include N-Boc, a targeting ligand, a drug, and/or an imaging agent. A number of such functionalized asymmetrical dendritic compounds can be used for various therapies, including cancer treatment.

21 Claims, 12 Drawing Sheets

Formula (Ia)

$R^1$—$X^1$—NH—L—G0—(NH-$X^2$-$R^2$)$_2$

Formula (Ib)

$R^1$—$X^1$—NH—L—G1—(NH-$X^2$-$R^2$)$_4$

A mixture of standard PAMAM dendrimer G0-folic acid conjugates

G0-4 folic acids

No further conjugation possible

| Chloramphenicol-glutaric acid-dendrimer-(folate)$_4$ | Concentration, μM |
|---|---|
| S66 | 190 |
| S68 | 48 |
| S69 | 24 |
| S70 | 12 |
| S71 | 6 |

N-BOC-DENDRIMERS AND THEIR CONJUGATES

CROSS-REFERENCE TO RELATED APPLICATIONS

This application claims priority to U.S. Provisional Application No. 61/694,200, entitled "N-BOC DENDRAMINE AND ITS CONJUGATES," filed on Aug. 28, 2012; which is incorporated herein by reference in its entirety. This application also claims priority to U.S. Provisional Application No. 61/815,879, entitled "N-BOC DENDRIMERS AND THEIR CONJUGATES," filed on Apr. 25, 2013; which is incorporated herein by reference in its entirety.

BACKGROUND OF THE INVENTION

Field of the Invention

The present invention relates to a composition for enhancing drug delivery, imaging resolution and/or affinity. More specifically, the present invention relates to a composition comprising mono-protected Boc-dendrimers and their conjugates.

Description of the Related Art

Cancer continues to be a significant health problem in our society and the number of cases per year is increasing as the population ages. Cancer is likely to impact 1 in 3 of us. According to the American Cancer Society's annual cancer statistics report, "Cancer Statistics, 2013," 1.6 million Americans will be diagnosed with invasive cancer in 2013, and 0.5 million Americans will die from cancer this year. Cytotoxic agents are currently the major chemotherapeutic treatment modality for most types of cancer. However, current cancer chemotherapeutic treatments remain inherently toxic and have severe side effects.

The role of magnetic resonance imaging (MRI) in the diagnosis and evaluation of cancer continues to evolve and become important because it is non-invasive and non-irradiating. See Bulte et al. "Magnetic resonance microscopy and histology of the CNS," *Trends in Biotechnology*, 2002, 20, S24-S28. Although images of tissues can be obtained, contrast agents significantly improve MRI resolution. A current FDA-approved MRI contrast agent is Gd-DTPA, commercialized as MAGNEVIST® gadopentetate dimeglumine Caravan et al. reported other Gd-chelates that are under development, see Caravan et al. "Gadolinium(III) Chelates as MRI Contrast Agents: Structure, Dynamics, and Applications," *Chem. Rev.* 1999, 99, 2293-2352. Similar to chemotherapeutic agents, currently approved contrast agents are also nonselective.

The folate-receptor (FR) is overexpressed on a number of major malignancies including adenocarcinoma of the lung and ovarian cancer, see Pribble P, Edelman M J. EC145: a novel targeted agent for adenocarcinoma of the lung. Expert Opin Investig Drugs. 2012; 21(5):755-61. However, relatively few small molecule drug conjugates with folic acid have been investigated since Dr. Fuchs's group at University of Purdue reported that Taxol-folic acid conjugates failed to demonstrate selective killing of folate receptor-expressing tumor cells in vitro or enhanced in vivo antitumor activity over Taxol when administered in an equimolar quantity formulated in the same injection vehicle. See Lee J W, Lu J Y, Low P S, Fuchs P L. Synthesis and evaluation of taxol-folic acid conjugates as targeted antineoplastics. Bioorg Med Chem. 2002, 10, 2397-414.

U.S. Pat. No. 7,128,893 disclosed vitamin-targeted imaging agents coupled via a divalent linker (vitamin-linker-imaging agent); U.S. Pat. No. 7,601,332 disclosed a vitamin-targeted drug delivery conjugate via a divalent linker (vitamin-linker-drug).

Relatively few multi-valent linker platforms have been reported. See the following U.S. patents: U.S. Pat. No. 4,435,548; U.S. Pat. No. 4,507,466; U.S. Pat. No. 4,558,120; U.S. Pat. No. 4,568,737; U.S. Pat. No. 4,587,329; U.S. Pat. No. 4,871,779; U.S. Pat. No. 4,631,337. U.S. Pat. No. 5,714,166, disclosed bioactive and/or targeted dendrimer conjugates. However, when a drug is conjugated to a dendrimer and followed by conjugation of a vitamin, a number of species result because it is difficult to control the location and the amount of the drug and the vitamin on the dendrimer. See Majoros I J, Myc A, Thomas T, Mehta C B, Baker J R. PAMAM Dendrimer-Based Multifunctional Conjugate for Cancer Therapy: Synthesis, Characterization, and Functionality. Biomacromolecules 2006, 7, 572-579.

Despite billions of dollars poured every year into developing better treatment options, there is an urgent need for safer and more effective therapies.

SUMMARY OF THE INVENTION

An embodiment provides an asymmetrical dendritic compound represented by the Formula (I):

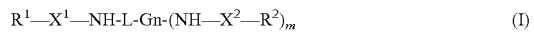

$$R^1—X^1—NH-L-Gn-(NH—X^2—R^2)_m \qquad (I)$$

wherein: Gn is a dendritic PAMAM group, having a core group and a shell group, for which n is zero or an integer in the range of 1 to 3 that specifies the generation of the dendritic PAMAM group; $R^1—X^1—NH-L$ is a group attached to the core group, wherein $R^1$ is selected from H, $NH_2NH$, $CO_2C(CH_3)_3$, a maleimide group, a targeting ligand, a drug, and an imaging agent; $X^1$ is absent or selected from $C(=O)(CH_2)_aC(=O)$, $C_{1-4}$ alkylene and $C_{1-8}$ alkyleneoxide; and L is absent or selected from $C_{1-4}$ alkylene and $C_{1-8}$ alkyleneoxide; $(NH—X^2—R^2)_m$ is a terminal group attached to the shell group, wherein m is 2, 4, 8 or 16 and specifies the number of the attached $NH—X^2—R^2$ terminal groups; each $X^2$ is independently absent or a linker selected from $C_{1-4}$ alkylene, succinimidyl, $C_{1-8}$ alkyleneoxide, $C(=O)(CH_2)_aC(=O)$, $C(=O)(CH_2)_aC(=O)—NH—C_{1-4}$alkylene-NH, $C(=O)(CH_2)_aC(=O)—NH—C_{1-8}$alkyleneoxide-NH; and each $R^2$ is independently selected from H, hydroxyl, a maleimide group, a succinimide group, a targeting ligand, a drug, and an imaging agent; each a is independently an integer in the range of 1 to 4; and each $R^2$ is different from $R^1$.

Another embodiment provides an asymmetrical dendritic compound as described herein that is represented by the Formulae (Ia), (Ib), (Ic) or (Id) as follows:

Formula (Ia)
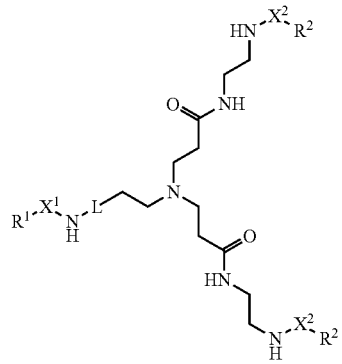
Formula (Ib)
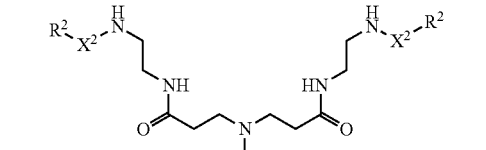
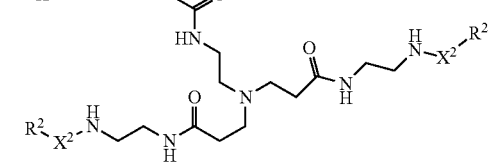
Formula (Ic)
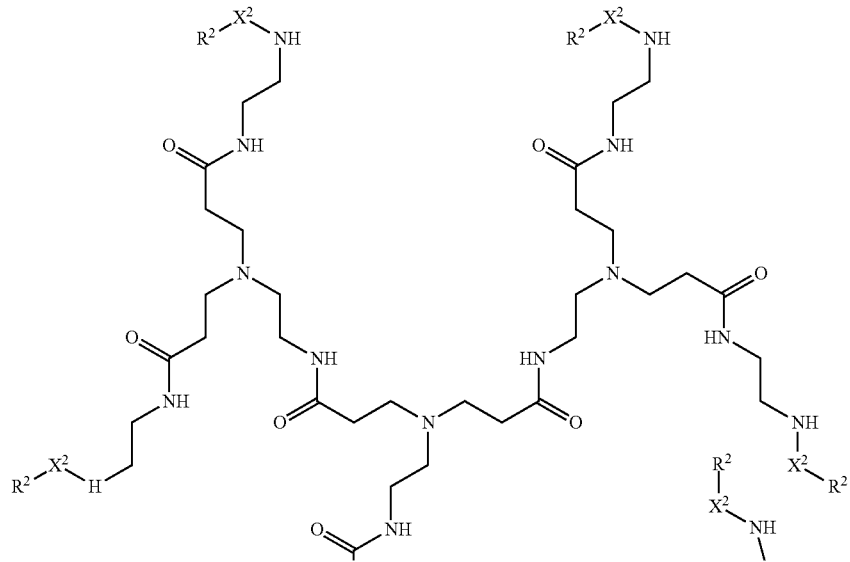

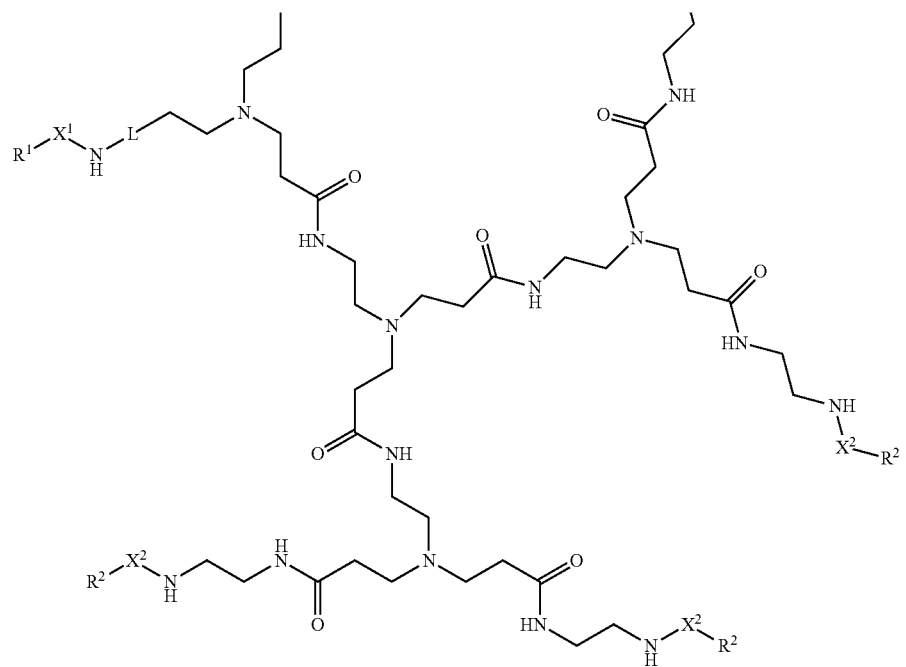
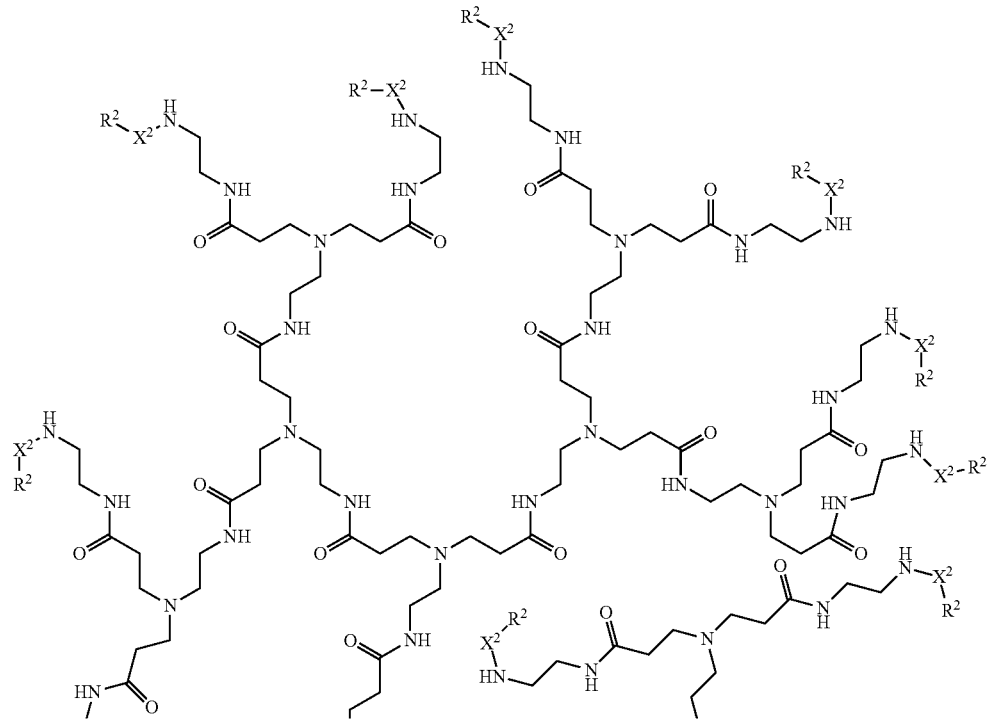
Formula (Id)

-continued

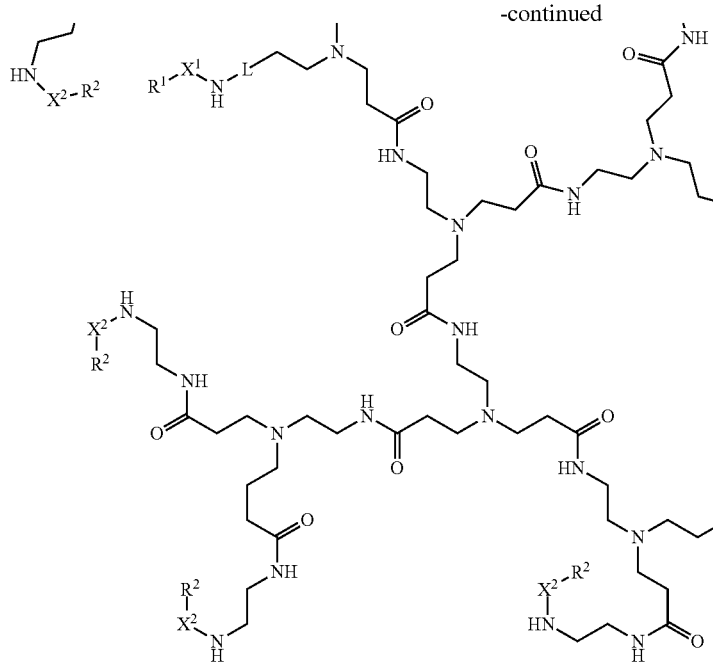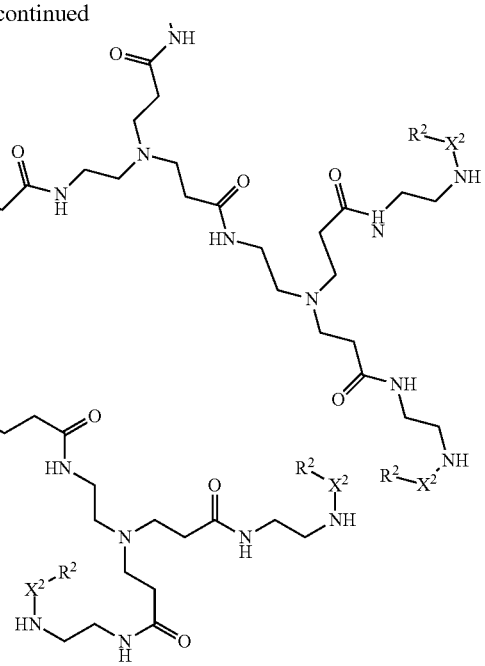

Another embodiment provides an asymmetrical dendritic compound as described herein in which $R^1$ is selected from the group consisting of H, $CO_2C(CH_3)_3$, and maleimide.

Another embodiment provides an asymmetrical dendritic compound as described herein in which $R^2$ comprises a targeting ligand.

Another embodiment provides an asymmetrical dendritic compound as described herein in which the targeting ligand is selected from the group consisting of folic acid, mannose, anisamide, RGD peptide, NGR peptide, galactosamine, antibody, antibody fragment, and protein.

Another embodiment provides an asymmetrical dendritic compound as described herein in which $R^2$ comprises an imaging agent.

Another embodiment provides an asymmetrical dendritic compound as described herein in which the imaging agent is selected from the group consisting of a Gadolinium (III)-chelate, a Technetium(99m)-chelate, a Gallium-chelate, and a Thallium-chelate.

Another embodiment provides an asymmetrical dendritic compound as described herein in which the imaging agent is selected from the group consisting of $^{64}Cu$ diacetyl-bis($N^4$-methylthiosemicarbazone), $^{18}F$-fluorodeoxyglucose, 3'-deoxy-3'-($^{18}F$)fluorothymidine, and $^{18}F$-fluoromisonidazole.

Another embodiment provides an asymmetrical dendritic compound as described herein in which $R^2$ comprises a drug.

Another embodiment provides a therapeutic agent represented by the Formula (I), wherein: Gn is a dendritic PAMAM group, having a core group and a shell group, for which n is zero or an integer in the range of 1 to 3 that specifies the generation of the dendritic PAMAM group; $R^1$—$X^1$—NH-L is a group attached to the core group, wherein $R^1$ is selected from a targeting ligand, an anticancer drug, and an imaging agent; $X^1$ is absent or selected from C(=O)($CH_2$)$_a$C(=O), $C_{1-4}$ alkylene and $C_{1-8}$ alkyleneoxide; and L is absent or selected from $C_{1-4}$ alkylene and $C_{1-4}$ alkyleneoxide; (NH—$X^2$—$R^2$)$_m$ is a terminal group attached to the shell group, wherein m is 2, 4, 8 or 16 and specifies the number of the attached NH—$X^2$—$R^2$ terminal groups; each $X^2$ is independently absent or a linker selected from $C_{1-4}$ alkylene, succinimidyl, $C_{1-8}$ alkyleneoxide, C(=O)($CH_2$)$_a$C(=O), C(=O)($CH_2$)$_a$C(=O)—NH—$C_{1-4}$alkylene-NH, C(=O)($CH_2$)$_a$C(=O)—NH—$C_{1-8}$alkyleneoxide-NH; each $R^2$ is independently selected from a targeting ligand, an anticancer drug, and an imaging agent; each a is independently an integer in the range of 1 to 4; and each $R^2$ is different from $R^1$.

Another embodiment provides a therapeutic agent as described herein in which one of $R^1$ and $R^2$ comprises a targeting ligand and the other of $R^1$ and $R^2$ comprises an anticancer drug or an imaging agent.

Another embodiment provides a therapeutic agent as described herein in which $R^1$ comprises an anticancer drug.

Another embodiment provides a therapeutic agent as described herein in which the anticancer drug is selected from the group consisting of doxorubicin, platinum, paclitaxel, docetaxel, combretastin A-4, vinblastine, vincristine, vinorelbine, camptothecin, SN-38, etoposide, teniposide, auristatin, calicheamicin, maytansinoid, and duocarmycin.

Another embodiment provides a therapeutic agent as described herein in which $R^1$ comprises an anticancer drug and $R^2$ comprises a folic acid targeting ligand.

Another embodiment provides a therapeutic agent as described herein in which $R^1$ comprises an imaging agent.

Another embodiment provides a therapeutic agent as described herein in which the imaging agent is selected from the group consisting of a Gadolinium (III)-chelate, a Technetium(99m)-chelate, a Gallium-chelate, and a Thallium-chelate.

Another embodiment provides a therapeutic agent as described herein in which the imaging agent is selected from the group consisting of $^{64}Cu$ diacetyl-bis($N^4$-methylthiosemicarbazone), $^{18}F$-fluorodeoxyglucose, 3'-deoxy-3'-($^{18}F$)fluorothymidine, and $^{18}F$-fluoromisonidazole.

Another embodiment provides a method of delivering a therapeutic agent to a cell, comprising contacting the cell with a therapeutic agent as described herein. In an embodiment, the contacting is conducted in vitro. In another embodiment, the contacting is conducted in vivo.

Another embodiment provides a method of treating cancer, comprising identifying a patient in need of cancer treatment and administering a therapeutically effective amount of a therapeutic agent as described herein.

Another embodiment provides a therapeutic agent as described herein for use in the treatment of cancer.

Another embodiment provides the use of a therapeutic agent as described in the manufacture of a medicament for the treatment of cancer.

Some embodiments disclosed herein relate to a N-Boc-dendrimer. Other embodiments disclosed herein relate to N-Boc-dendrimer with generation 0 (G0). Other embodiments disclosed herein related to N-Boc-dendrimers with generations 1 (G1), 2 (G2), 3 (G3), and 4 (G4).

Some embodiments disclosed herein relate to a method of making N-Boc-dendrimers G0, G1, G2, G3, and G4.

Some embodiments of the compositions disclosed herein relate to N-Boc-dendrimer that can include two targeting ligands. The targeting ligand is selected from the group consisting of folic acid, mannose, anisamide, RGD peptide, NGR peptide, galactosamine, antibody, antibody fragments, and protein. Other embodiments of the compositions disclosed herein relate to N-Boc-dendrimer that can include four targeting ligands. Other embodiments of the compositions disclosed herein relate to N-Boc-dendrimer that can include eight targeting ligands. Other embodiments of the compositions disclosed herein relate to N-Boc-dendrimer that can include sixteen targeting ligands. Other embodiments of the compositions disclosed herein relate to N-Boc-dendrimer that can include thirty-two targeting ligands.

Some embodiments of the compositions disclosed herein relate to dendrimer that can include an imaging agent and two targeting ligands. The imaging agent can be selected from optical imaging agent and magnetic resonance imaging, and the targeting ligand is selected from the group consisting of folic acid, mannose, anisamide, RGD peptide, NGR peptide, galactosamine, antibody, antibody fragments, and protein. Other embodiments of the compositions disclosed herein relate to dendrimer that can include an imaging agent and four targeting ligands. Other embodiments of the compositions disclosed herein relate to dendrimer that can include an imaging agent and eight targeting ligands. Other embodiments of the compositions disclosed herein relate to dendrimer that can include an imaging agent and sixteen targeting ligands. Other embodiments of the compositions disclosed herein relate to dendrimer that can include an imaging agent and thirty-two targeting ligands.

Some embodiments of the compositions disclosed herein relate to dendrimer that can include an anticancer drug and two targeting ligands. The drug is selected from the group consisting of doxorubicin, platinum, SN-38, paclitaxel, docetaxel, combretastin A-4, vinblastine, vincristine, vinorelbine, camptothecin, etoposide, teniposide, auristatin, calicheamicin, maytansinoid, and duocarmycin. The targeting ligand is selected from the group consisting of folic acid, mannose, anisamide, RGD peptide, NGR peptide, galactosamine, antibody, antibody fragments, and protein. Other embodiments of the compositions disclosed herein relate to dendrimer that can include a drug and four targeting ligands. Other embodiments of the compositions disclosed herein relate to dendrimer that can include a drug and eight targeting ligands. Other embodiments of the compositions disclosed herein relate to dendrimer that can include sixteen targeting ligands. Other embodiments of the compositions disclosed herein relate to dendrimer that can include thirty-two targeting ligands.

Some embodiments described herein relate to a method of imaging a tumor that can include administering an effective amount of a dendrimer that includes an imaging contrast agent and two targeting ligands described herein. The targeting ligand is selected from the group consisting of folic acid, mannose, anisamide, RGD peptide, NGR peptide, galactosamine, antibody, antibody fragments, and protein. Other embodiments described herein relate to a method of imaging a tumor using a dendrimer that includes an imaging contrast agent and four targeting ligands. Still other embodiments described herein relate to a method of imaging a tumor using a dendrimer that includes an imaging contrast agent and eight targeting ligands. Still other embodiments described herein relate to a method of imaging a tumor using a dendrimer that includes an imaging contrast agent and sixteen and thirty-two targeting ligands.

Some embodiments described herein relate to a method of treating a tumor that can include administering an effective amount of a dendrimer that includes a drug and two targeting ligands described herein. The targeting ligand is selected from the group consisting of folic acid, mannose, anisamide, RGD peptide, NGR peptide, galactosamine, antibody, antibody fragments, and protein. Other embodiments described herein relate to a method of treating a tumor using a dendrimer that includes a drug and four targeting ligands. Still other embodiments described herein relate to a method of treating a tumor using a dendrimer that includes a drug and eight targeting ligands. Still other embodiments described herein relate to a method of treating a tumor using a dendrimer that includes a drug and sixteen targeting ligands. Still other embodiments described herein relate to a method of treating a tumor using a dendrimer that includes a drug and thirty-two targeting ligands.

Another embodiment described herein relates to a method of making the dendrimer that includes an imaging agent with two targeting ligands, four targeting ligands, eight targeting ligands, sixteen, or thirty-two targeting ligands comprising the steps of at dissolving N-Boc-dendrimer described herein in an aprotic solvent (e.g. DMF, DCM, or DMSO), and coupling with two targeting ligands, four targeting ligands, eight targeting ligands, sixteen, or thirty-two targeting ligands; then deprotect the Boc protecting group-dendrimer-two, four, eight, sixteen, or thirty-two ligands, respectively, with trifluoroacetic acid and follow with a coupling of an imaging agent.

Another embodiment described herein relates to a method of making the dendrimer that includes an imaging agent with two targeting ligands, four targeting ligands, eight targeting ligands, sixteen targeting ligands, thirty-two ligands comprising the steps of at dissolving N-Boc-dendrimer described herein in an aprotic solvent (e.g. DMF or DMSO), and coupling with two targeting ligands, four targeting ligands, eight targeting ligands, sixteen, or thirty-two targeting ligands; then deprotect the Boc protecting group-dendrimer-two targeting ligands, four targeting ligands, eight targeting ligands, sixteen, or thirty-two targeting ligands, respectively, with trifluoroacetic acid and follow with coupling of a anticancer drug. The drug is selected from the group consisting of doxorubicin, platinum, SN-38, paclitaxel, docetaxel, combretastin A-4, vinblastine, vincristine, vinorelbine, camptothecin, etoposide, teniposide, auristatin, calicheamicin, maytansinoid, and duocarmycin. The targeting ligand is selected from the group consisting of folic acid, mannose, anisamide, RGD peptide, NGR peptide, galactosamine, antibody, antibody fragments, and protein.

Some embodiments of the compositions disclosed herein relate to dendrimer that can include a maleimide group and two anticancer drugs. For example, the drug is selected from a group of doxorubicin, platinum, SN-38, paclitaxel, docetaxel, combretastin A-4, vinblastine, vincristine, vinorelbine, camptothecin, etoposide, teniposide, auristatin, calicheamicin, maytansinoid, and duocarmycin. The targeting ligand is selected from the group consisting of folic acid, mannose, anisamide, RGD peptide, NGR peptide, galactosamine, antibody, antibody fragments, and protein. Other embodiments of the compositions disclosed herein relate to dendrimer that can include a drug and four targeting ligands. Other embodiments of the compositions disclosed herein relate to dendrimer that can include a drug and eight targeting ligands. Other embodiments of the compositions disclosed herein relate to dendrimer that can include a drug and sixteen and thirty-two targeting ligands.

Another embodiment described herein relates to a method of making the dendrimer that includes a maleimide group and two anticancer drugs, four anticancer drugs, eight anticancer drugs, sixteen, or thirty-two anticancer drugs comprising the steps of at dissolving N-Boc-dendrimer described herein in an aprotic solvent (e.g. DMF, DCM, or DMSO), and coupling with two anticancer drugs, four anticancer drugs, anticancer drugs, sixteen, or thirty-two anticancer drugs; then deprotect the Boc protecting group-dendrimer-two anticancer drugs, four anticancer drugs, anticancer drugs, sixteen, or thirty-two anticancer drugs with trifluoroacetic acid (TFA) and follow with coupling of a maleimide group.

These and other embodiments are described in greater detail below.

DETAILED DESCRIPTION OF THE PREFERRED EMBODIMENTS

Figure 1A:
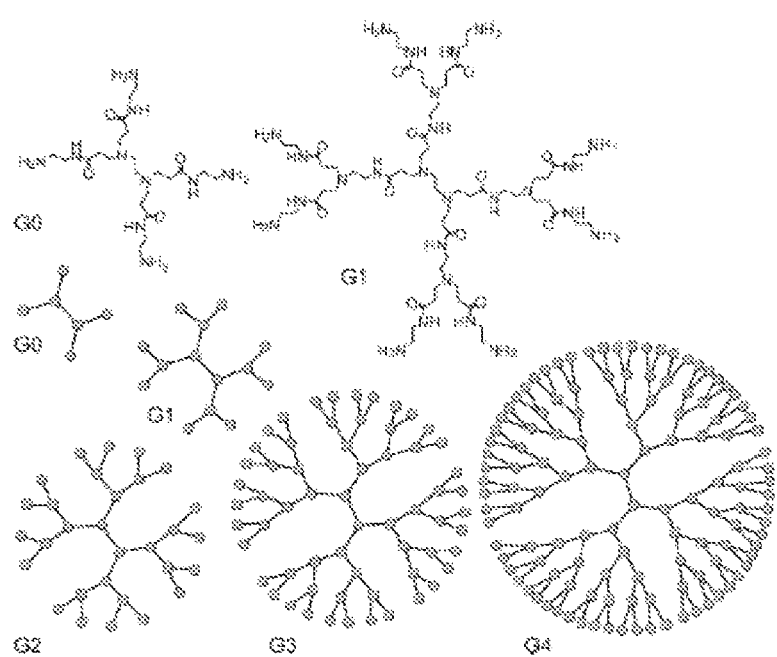
FIG. 1A is a schematic illustrating the chemical structures of G0 and G1 PAMAM dendrimers, and schematic depictions of G0, G1, G2, G3 and G4 PAMAM dendrimers.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

The term "dendrimer" and similar terms are used herein in a manner consistent with the understanding of those skilled in the art, see D A Tomalia, "Birth of a New Macromolecular Architecture: Dendrimers as Quantized Building Blocks for Nanoscale Organic Chemistry", Aldrichimica Acta, 37(2) 39-57 (2004), which may be referred to herein as "Tomalia 2004" and which is hereby incorporated by reference in its entirety and particularly for the purpose of describing dendrimers and methods of making them. Various terms used to characterize aspects of dendrimers (such as generation, G0, G1, G2, G3, G4, core, shell, etc.) are likewise used in a manner consistent with the understanding of those skilled in the art, see Tomalia 2004. For example, the term "PAMAM dendrimer" and similar terms are used herein in a manner consistent with the understanding of those skilled in the art to refer to poly (amidoamine) dendrimers, see, e.g., FIG. 1A and Tomalia 2004 at p. 44. The term "asymmetrical dendrimer" and similar terms are used herein in a manner consistent with the understanding of those skilled in the art to refer to dendrimers that are functionalized in a non-symmetrical manner, e.g., as represented by the Formula (I) and illustrated in FIG. 1B. Those skilled in the art will recognize that an asymmetrical dendrimer is a type of dendrimer.

The terms "targeting agent", "targeting ligand" and similar terms are used herein in a manner consistent with the understanding of those skilled in the art to refer to compounds that can be attached to a dendrimer to provide specific targeting to a particular body tissue. For example, the use of folic acid as a folate receptor targeting agent for a dendrimer to which folic acid is attached is disclosed in Majoros et al, "PAMAM Dendrimer-Based Multifunctional Conjugate for Cancer Therapy: Synthesis, Characterization, and Functionality", Biomacromolecules 7 572-579 (2006), which may be referred to herein as "Majoros 2006."

A variety of targeting agents known to those skilled in the art may be attached to the asymmetrical dendrimers described herein. See, e.g., Jie et al, "Peptides as targeting probes against tumor vasculature for diagnosis and drug delivery", Journal of Translational Medicine 10(Supp11):51 1-9 (2012), which may be referred to herein as "Jie 2012." Examples of targeting agents include folic acid (including folic acid itself and derivatives that target folate receptor), mannose (including mannose itself and derivatives that target mannose receptors, which are highly expressed in cells of the immune system), anisamide (including anisamide itself and derivatives that target the sigma receptor), RGD peptide (including arginine-glycine-aspartic acid itself and derivatives that target tumor vasculature), NGR peptide (including asparagine-glycine-arginine itself and derivatives that target tumor vasculature), galactosamine (including galactosamine itself and derivatives that target the asialoglycoprotein receptor), antibody (see Jie 2012), antibody fragment (see Jie 2012), and protein (see Jie 2012).

The term "imaging agent" and similar terms are used herein in a manner consistent with the understanding of those skilled in the art to refer to compounds that can be attached to a dendrimer to enhance in vitro and/or in vivo imaging of the dendrimer. Examples of imaging agents include Gadolinium (III)-chelate, Technetium(99m)-chelate, Gallium-chelate, Thallium-chelate, $^{64}Cu$ diacetyl-bis(N$^4$-methylthiosemicarbazone), $^{18}F$-fluorodeoxyglucose, 3'-deoxy-3'-($^{18}F$)fluorothymidine, and $^{18}F$-fluoromisonidazole.

The term "drug" and similar terms are used herein in a manner consistent with the understanding of those skilled in the art to refer to compounds that can provide a therapeutic or diagnostic benefit to subjects to which they are administered in effective amounts, whether or not such compounds have received regulatory approval for such purpose. For example, the term "anticancer drug" and similar terms are used herein to refer to drugs having efficacy against cancer, such as fluoromisonidazole, doxorubicin, platinum, paclitaxel, docetaxel, combretastin A-4, vinblastine, vincristine, vinorelbine, camptothecin, SN-38, etoposide, teniposide, auristatin, calicheamicin, maytansinoid, and duocarmycin. In this context, those skilled in the art will understand that reference herein to a drug as "platinum" includes reference to various anticancer drugs that contain platinum, such as cisplatin. Similarly, those skilled in the art will recognize that the term "SN-38" refers to an anticancer drug that is the active metabolite of the topoisomerase I inhibitor irinotecan.

Various asymmetrical dendritic compounds described herein include a targeting ligand, a drug, or an imaging agent, e.g., as $R^1$ or $R^2$. Those skilled in the art will recognize that attachment of such a targeting ligand, drug, or imaging agent to the asymmetrical dendritic compounds may be accomplished in various ways, e.g., by chemical bonding (directly or via an appropriate linker). Thus, those skilled in the art understand that the chemical structure of the attached version of the targeting ligand, drug, or imaging agent may differ slightly from the non-attached version because of the manner in which it is attached (e.g., by covalent bond). For example, a folic acid (also referred to herein as folate) targeting ligand can be attached to an asymmetrical dendritic compound by an amide bond as illustrated in Formulae (XXI) to (XXVIII). Thus, reference herein to a targeting ligand, drug, or imaging agent will be understood to include both attached and unattached versions, depending on the context, unless stated otherwise.

Figure 2:
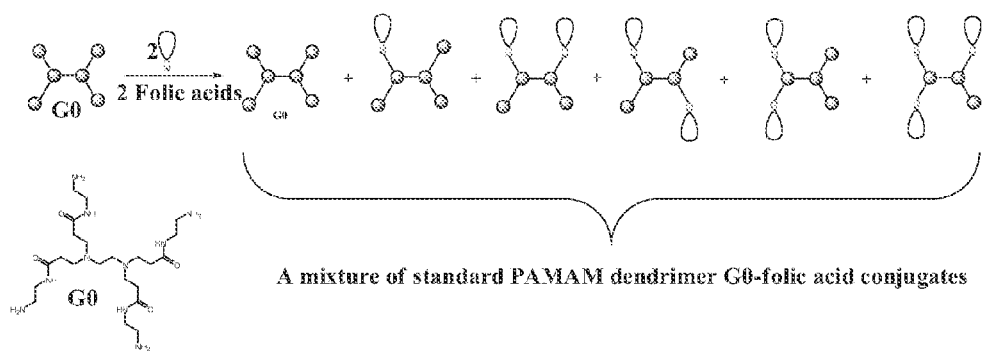
FIG. 2 is a schematic illustrating the conjugation of two folic acids onto a PAMAM dendrimer G0, which generates a mixture of products.
Figure 3:
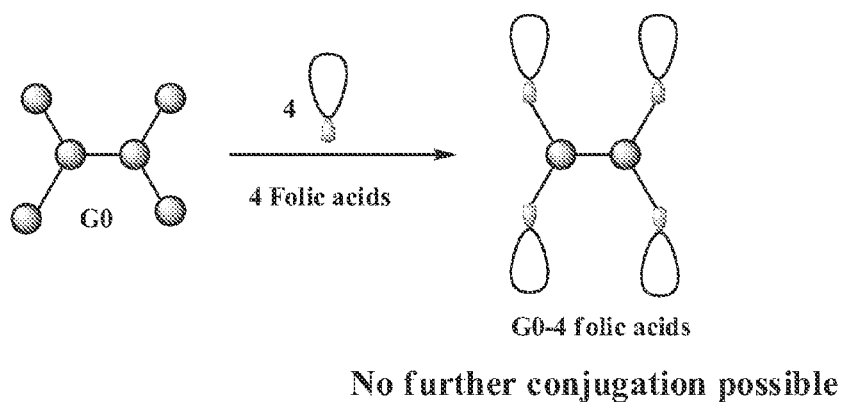
FIG. 3 is a schematic illustrating the conjugation of four folic acids onto a PAMAM dendrimer G0.

Various embodiments provide an asymmetrical dendritic compound represented by the Formula (I), wherein Gn is a dendritic PAMAM group, having a core group and a shell group, for which n is zero or an integer in the range of 1 to 3 that specifies the generation of the dendritic PAMAM group. Formula (I) also includes a $R^1$—$X^1$—NH-L group attached to the core group, and a number of $X^2$—$R^2$ terminal groups attached to the shell group. The asymmetrical dendrimers of the Formula (I) can be prepared in a precise and well controlled manner as described in greater detail herein, and thus are substantially pure. For example, in various embodiments the asymmetrical dendrimers of the Formula (I) have a purity of about 95% or greater, e.g., about 98% or greater, by weight based on total weight of asymmetrical dendrimers. Since the basis for evaluating the purity of the asymmetrical dendrimers of the Formula (I) is the total amount of asymmetrical dendrimers, those skilled in the art will recognize that the asymmetrical dendrimers of the Formula (I) may be substantially pure even when intermixed with other components, e.g., when dissolved in a solvent. In contrast, prior methods of making asymmetrical dendrimers tend to result in a statistical mixture of products. For example FIG. 2 illustrates a mixture of products resulting from the reaction between 2 moles of a folic acid ligand and one mole of a G0 PAMAM dendrimer. Under the reaction conditions illustrated in FIG. 2, the G0 PAMAM dendrimers are functionalized with an average of about 2 folic acids per dendrimer, but the product of the illustrated reaction is a mixture that also contains unreacted G0 PAMAM dendrimer as well as mono- and tri-functionalized dendrimer. Likewise, the methods disclosed in Majoros 2006 involve attaching folic acid to partially acetylated monofunctional dendrimer conjugates, resulting in mixtures containing a variety of functionalized dendrimers having different numbers of attached folic acid molecules (calculated average of 4.5 per dendrimer, see Majoros 2006 at p. 576). Those skilled in the art will recognize that the reaction between a folic acid ligand and PAMAM dendrimer illustrated in FIG. 2 can also result in a G0 dendrimer functionalized with 4 folic acids as illustrated in FIG. 3. Such conjugation with all of the readily available amine groups of the PAMAM dendrimer renders the resulting G0-4 folic acids conjugate difficult or impossible to further functionalize (e.g, with drug and/or imaging agent) as illustrated in FIG. 3.

Those skilled in the art understand that symmetrical dendrimers are often represented by the formula Gx, where x is the generation of the dendrimer. For example, FIG. 1A illustrates conventional PAMAM dendrimers of generation G0 and G1. In some cases, the notation Gx-R is used to represent conventional dendrimers, where x is the generation of the dendrimer and R is the terminal group of the dendrimer. Thus, the amine-terminated conventional PAMAM dendrimers of generation G0 and G1 illustrated in FIG. 1A can be referred to as G0-NH$_2$ and G1-NH$_2$, respectively.

Figure 1B:
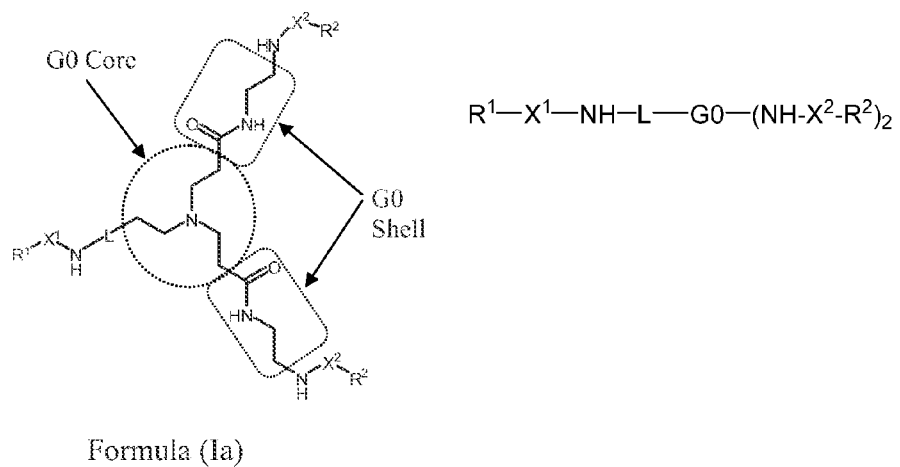
FIG. 1B illustrates aspects of the chemical structures of embodiments of the asymmetrical dendritic compounds represented by the Formula (I).
Figure 1B:
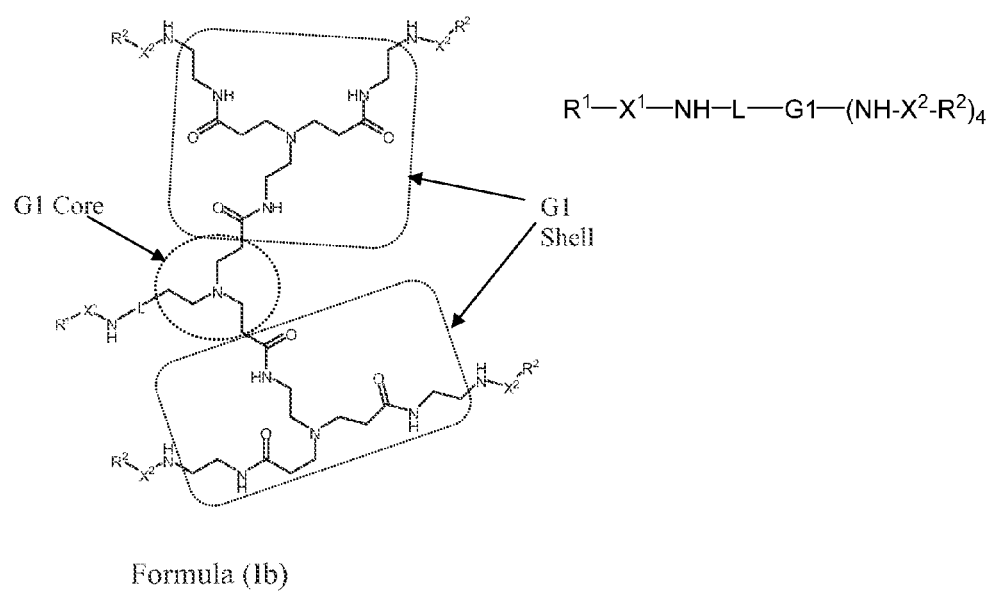

The terminology used to represent conventional dendrimers has been adapted to represent the asymmetrical dendritic compounds of the general Formula (I) described herein. For example, FIG. 1B shows asymmetrical dendritic compounds of the Formula (Ia) and (Ib) in which the core and shell groups of the dendritic PAMAM group have been indicated. Those skilled in the art will recognize that the asymmetrical dendritic compounds of the Formula (Ia) can be represented by the Formula (I) in which n=0 and m=2. In particular, FIG.

1B illustrates compounds of the Formula (Ia) in which a $R^1$—$X^1$—NH-L group is attached to the core of a G0 dendritic PAMAM group and two (m=2) NH—$X^2$—$R^2$ terminal groups are attached to the shell groups. Likewise, those skilled in the art will recognize that the asymmetrical dendritic compounds of the Formula (Ib) can be represented by the Formula (I) in which n=1 and m=4. In particular, FIG. 1B also illustrates compounds of the Formula (Ib) in which a $R^1$—$X^1$—NH-L group is attached to the core of a G1 dendritic PAMAM group and four (m=4) NH—$X^2$—$R^2$ terminal groups are attached to the shell groups. The asymsuch as certain of the aforementioned L groups can be arranged in the opposite way. Thus, for example, reference herein to an L group as —OCH$_2$CH$_2$OCH$_2$CH$_2$— will be understood to include —CH$_2$CH$_2$OCH$_2$CH$_2$O— and vice versa, unless otherwise indicated.

Some embodiments described herein relate to a method of making N-Boc-dendrimers comprising a two-stage reaction: (1) Michael addition reaction of mono-protected N-Boc-diamine with methyl acrylate to form the N-Boc-dendrimer methyl ester, (2) amidation of ethylene diamine with the N-Boc-dendrimer methyl ester to form N-Boc-dendrimers as shown in the following reaction scheme:

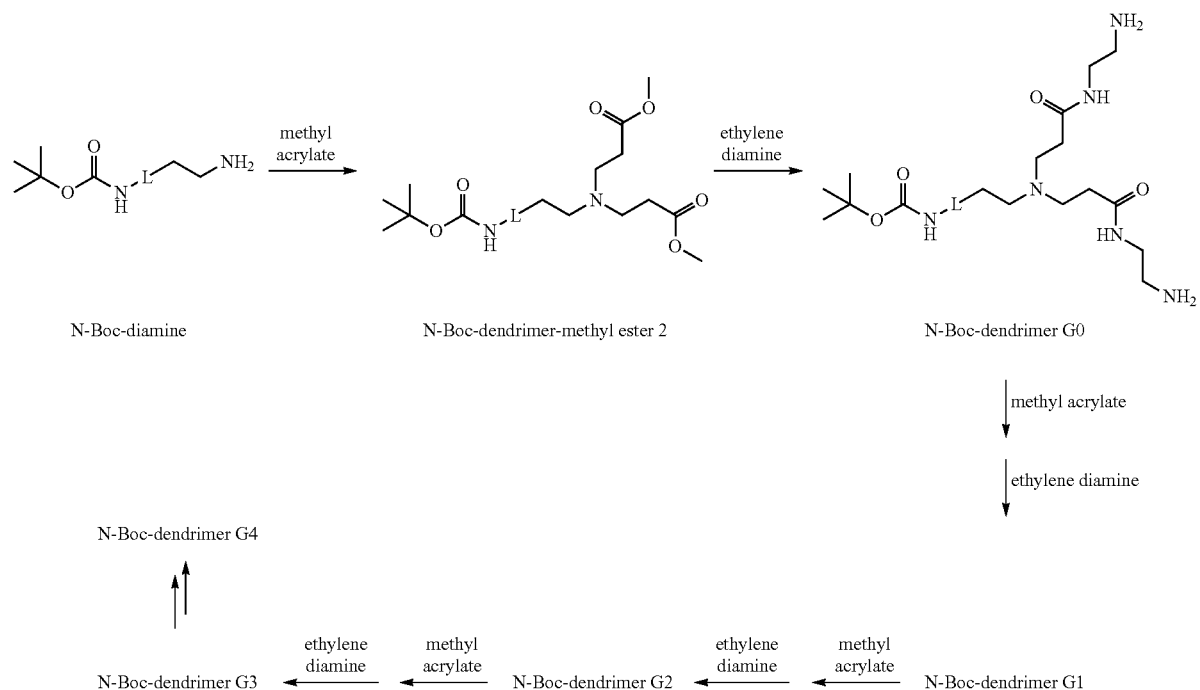

metrical dendritic compounds of the Formula (I) may be referred to herein as dendrimers.

Figure 4A:
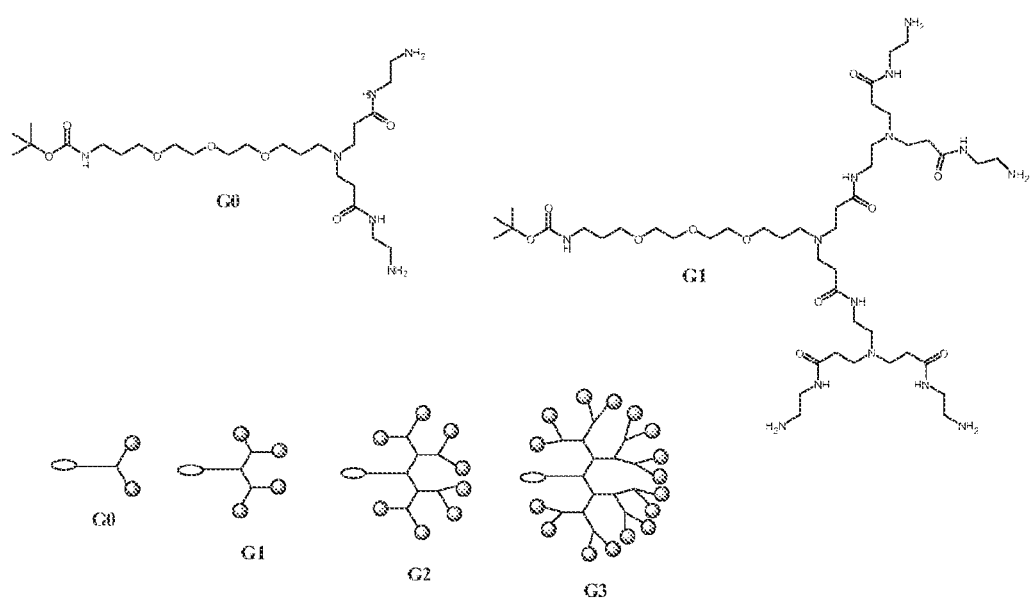
FIG. 4A illustrates the chemical structures of embodiments of G0 and G1 N-Boc-dendrimers, as well as schematic depictions of N-Boc-dendrimers, generations 0-3 (G0-G3).
Figure 4B:
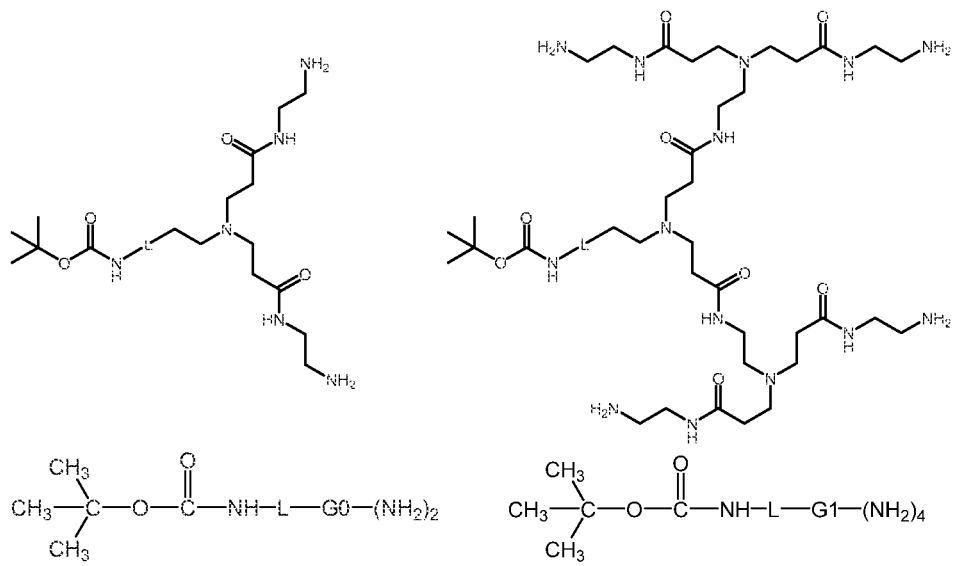
FIGS. 4B-4D illustrate the chemical structures of various N-Boc-dendrimers and the corresponding Formula (I) for each.
Figure 4C:
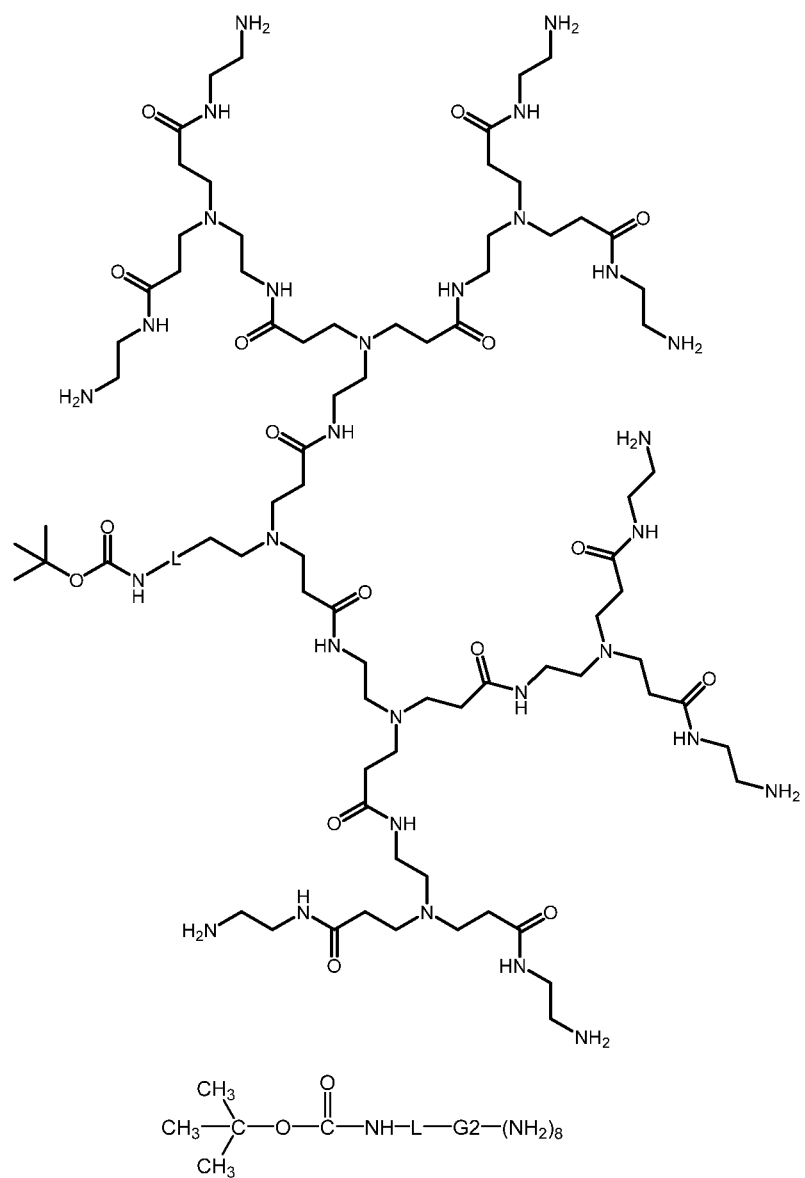
Figure 4D:
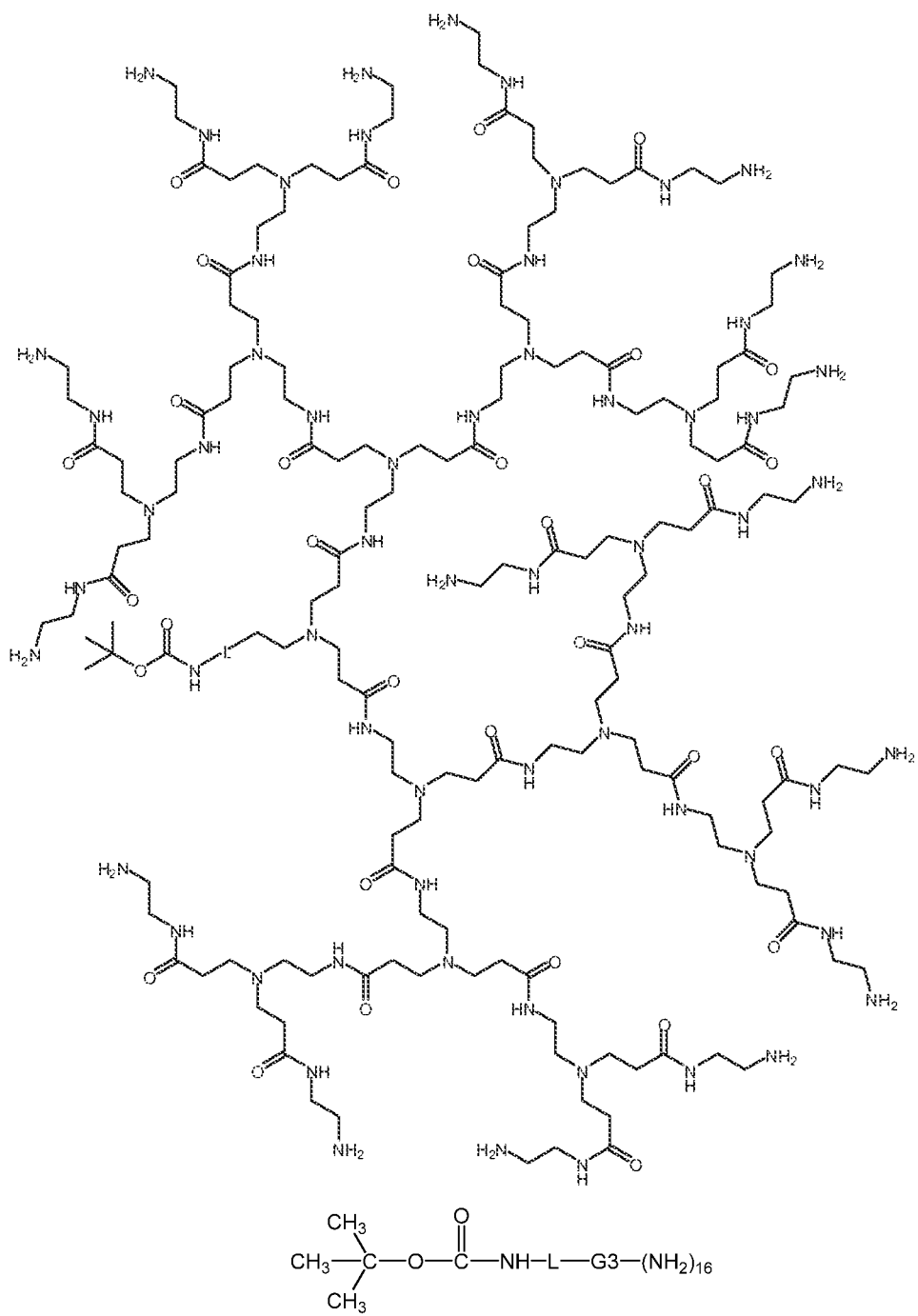

Some embodiments described herein are directed to G0, G1, G2 and G3 asymmetrical dendritic compounds of the general Formula (I) in which the $R^1$—$X^1$—NH-L group comprises N-Boc (which may be generally referred to herein as N-Boc-dendrimers). For example, FIG. 4A illustrates the chemical structures of embodiments of G0 and G1 N-Boc-dendrimers, as well as schematic depictions of G0, G1, G2 and G3 asymmetrical dendritic compounds of the Formula (I). The structures of various N-Boc-dendrimers and the corresponding Formula (I) for each are illustrated in FIGS. 4B-4D.

Those skilled in the art will recognize that N-Boc-dendrimers having such structures may be represented by Formula (I) in which $R^1$ is CO$_2$C(CH$_3$)$_3$, $X^1$ is absent, n is zero or an integer in the range of 1 to 3, $X^2$ is absent, and $R^2$ is H. In various embodiments, each L is independently absent or selected from C$_{1-4}$ alkylene and C$_{1-8}$ alkyleneoxide; e.g., each L can be independently absent or selected from the group consisting of —CH$_2$—, —CH$_2$CH$_2$—, —CH$_2$CH$_2$CH$_2$—, —CH$_2$CH$_2$CH$_2$CH$_2$—, —OCH$_2$CH$_2$OCH$_2$CH$_2$—, and —CH$_2$OCH$_2$CH$_2$OCH$_2$CH$_2$OCH$_2$CH$_2$—. Those skilled in the art will recognize that various groups herein In the reaction scheme, L is defined as described elsewhere herein. Those skilled in the art will recognize that such two-stage reactions can be continued to expand the dendritic PAMAM group to G1, G2, G3, G4, etc., by reaction with ethylene diamine and methyl acrylate in the usual manner, as desired.

Other embodiments described herein relate to a method of making N-Boc-dendrimers comprising a two-stage reaction: (1) Michael addition reaction of mono-protected N-Boc-diamine and methyl acrylate to form the N-Boc-dendrimer methyl ester, (2) amidation of ethylene diamine and the N-Boc-dendrimer methyl ester at various temperatures in the range of 30° C. to 100° C., e.g., 30° C., 40° C., 50° C., 60° C., 70° C., 80° C., 90° C., or 100° C., to form the N-Boc-dendrimer. Still other embodiments described herein relate to a method of making N-Boc-dendrimers comprising a two-step reaction: (1) Michael addition reaction of mono-protected N-Boc-diamine and methyl acrylate to form the N-Boc-dendrimer methyl ester, (2) amidation of ethylene diamine and the N-Boc-dendrimer methyl ester to form N-Boc-dendrimer at a temperature in the range of 20° C. to 90° C. Still other embodiments described herein relate to a method of making N-Boc-dendrimer comprising a two-step reaction: (1) Michael addition reaction of mono-protected N-Boc-diamine and methyl acrylate to form the N-Bocdendrimer methyl ester, (2) amidation of ethylene diamine and the N-Boc-dendrimer methyl ester to form N-Boc-dendrimer in methanol at a temperature in the range of ambient temperature to 100°, e.g., 30° C., 40° C., 50° C., 60° C., 70° C., 80° C., 90° C., or 100° C., to form the N-Boc-dendrimer.

Some embodiments of the compositions described herein relate to N-Boc-dendrimers that can include two targeting ligands and its protected (N-Boc) or deprotected ($X^1$ absent, $R^1$=H) form. For example, the targeting ligand can each be independently selected from the group consisting of folic acid, mannose, anisamide, RGD peptide, NGR peptide, galactosamine, antibody, antibody fragments, and protein. Other embodiments of the compositions disclosed herein relate to N-Boc-dendrimers that can include four targeting ligands. Other embodiments of the compositions disclosed herein relate to N-Boc-dendrimers that can include eight targeting ligands. Other embodiments of the compositions disclosed herein relate to N-Boc-dendrimers that can include sixteen targeting ligands. For example, the dendrimers can have the following structures as shown in Formulae (V)-(XII):

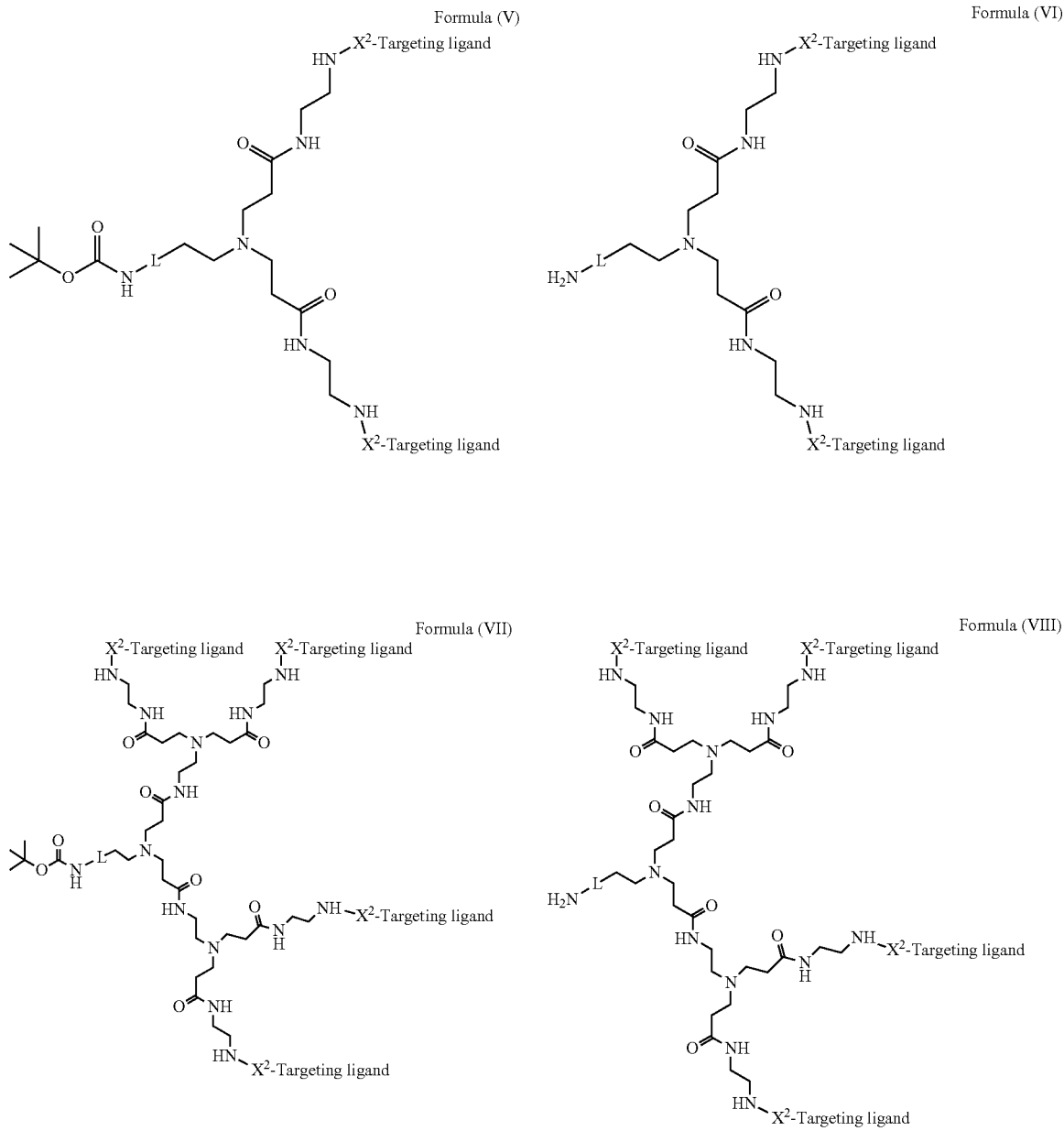

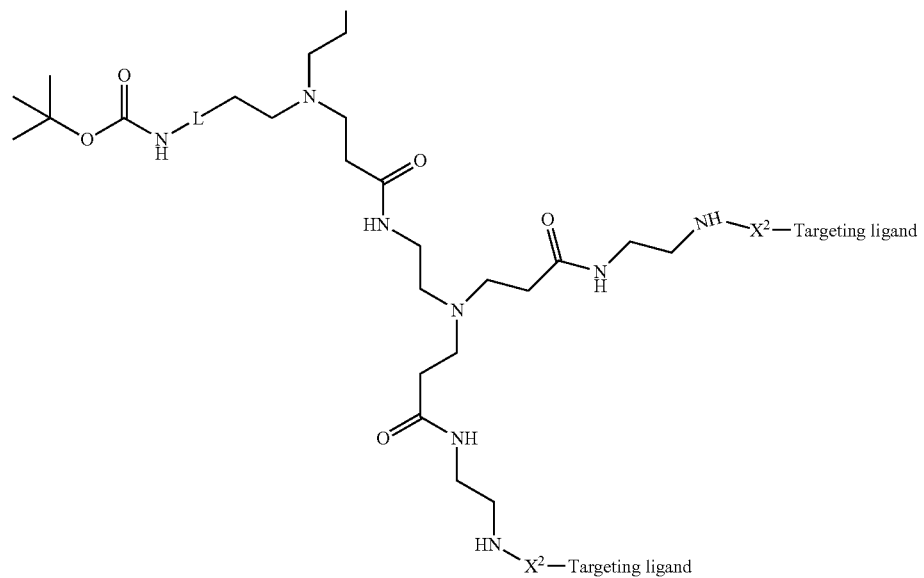
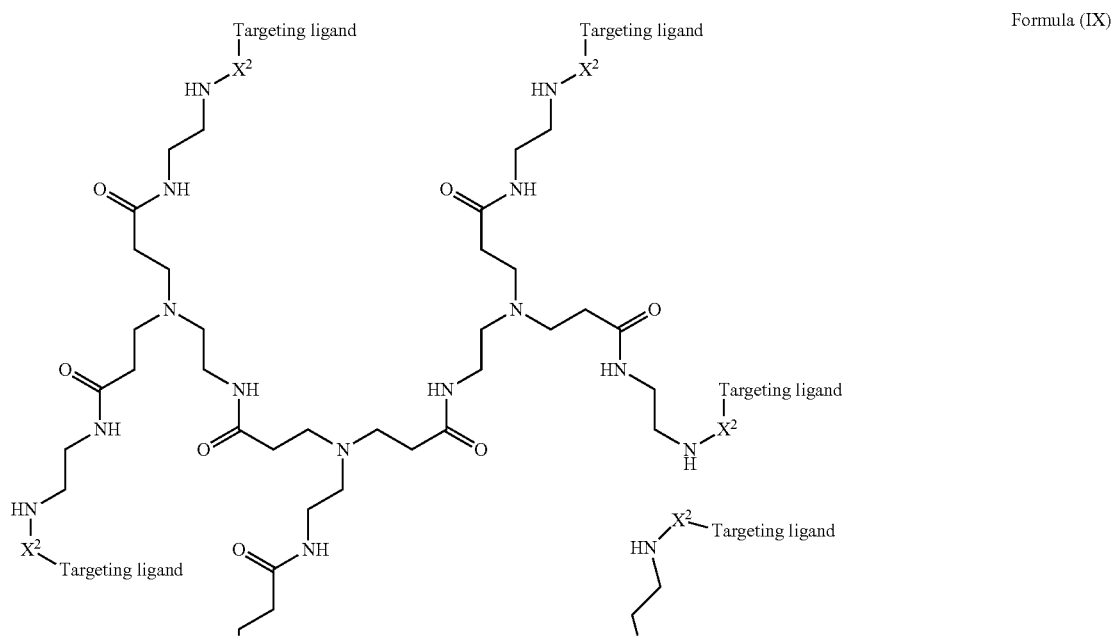
Formula (IX)

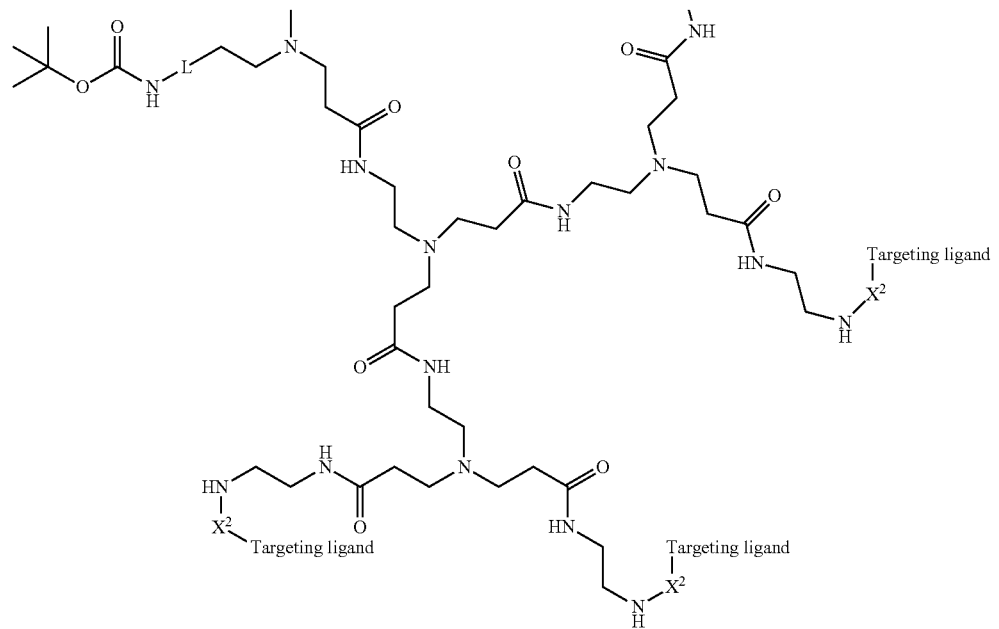
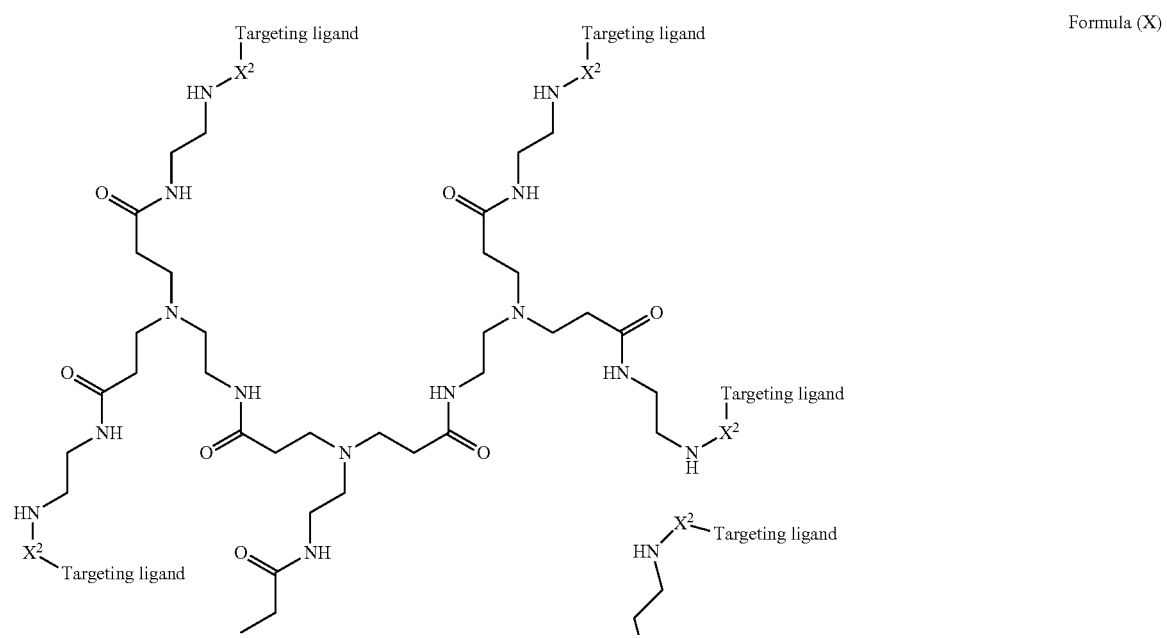
Formula (X)

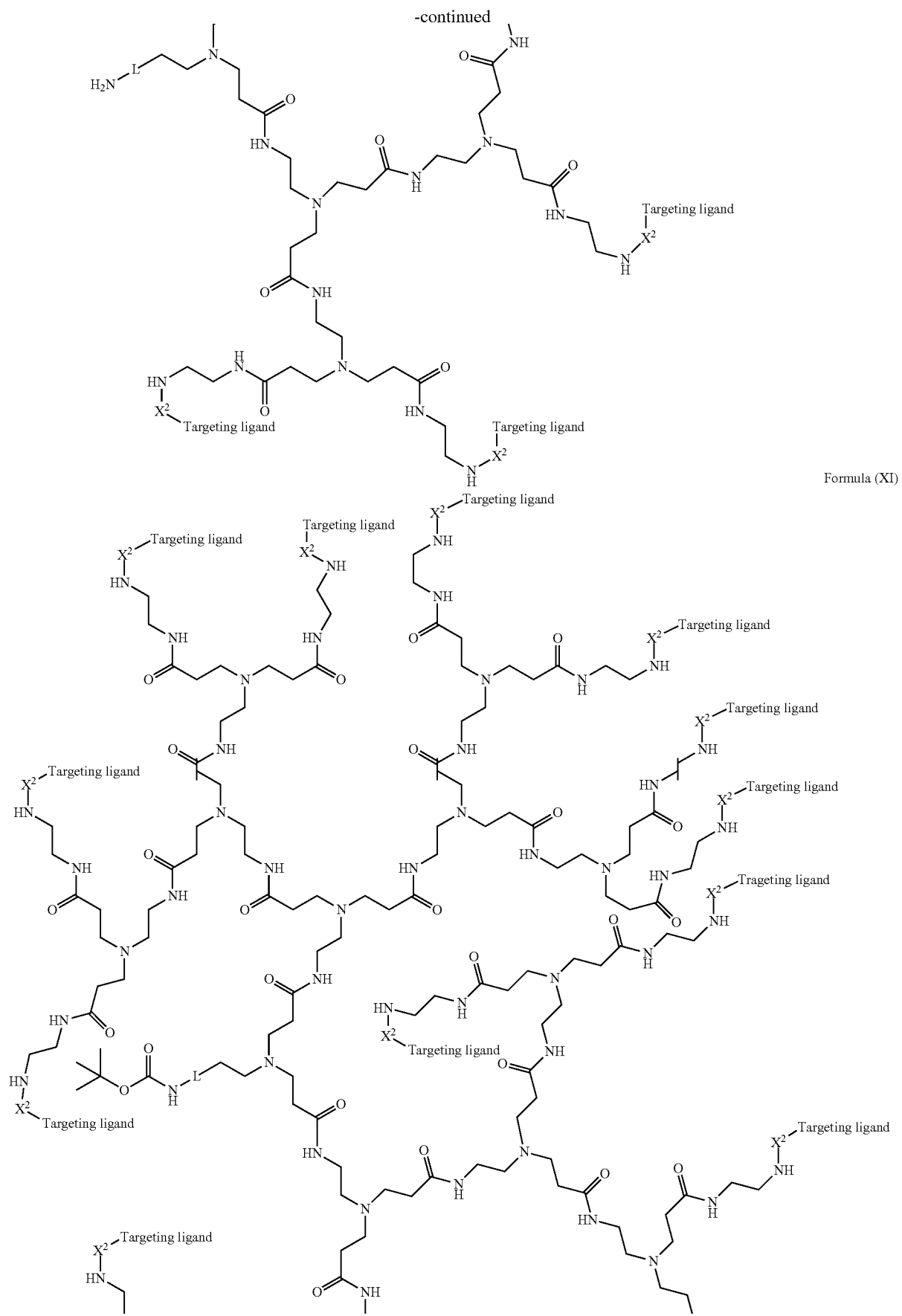
Formula (XI)

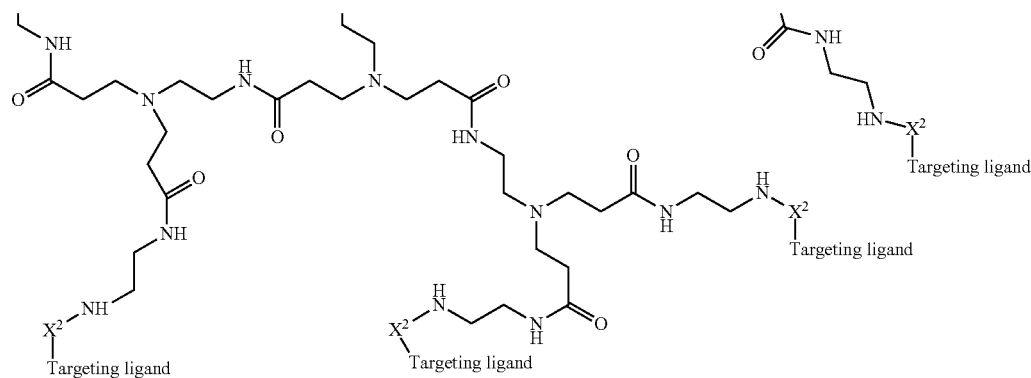
Formula (XII)
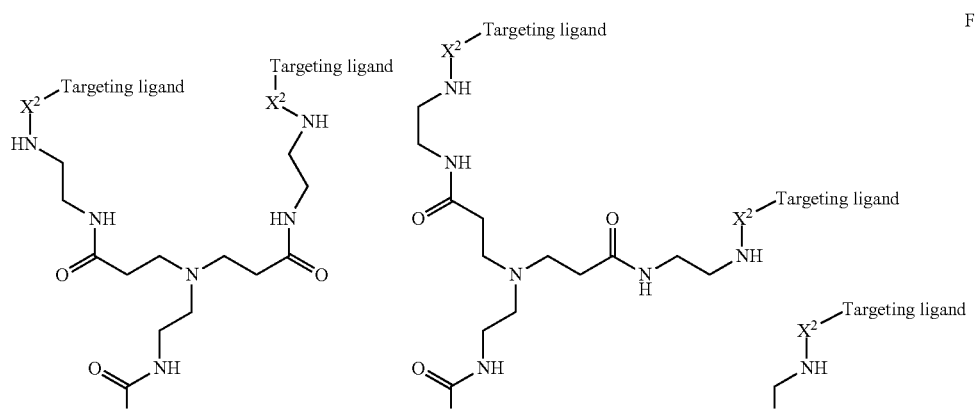
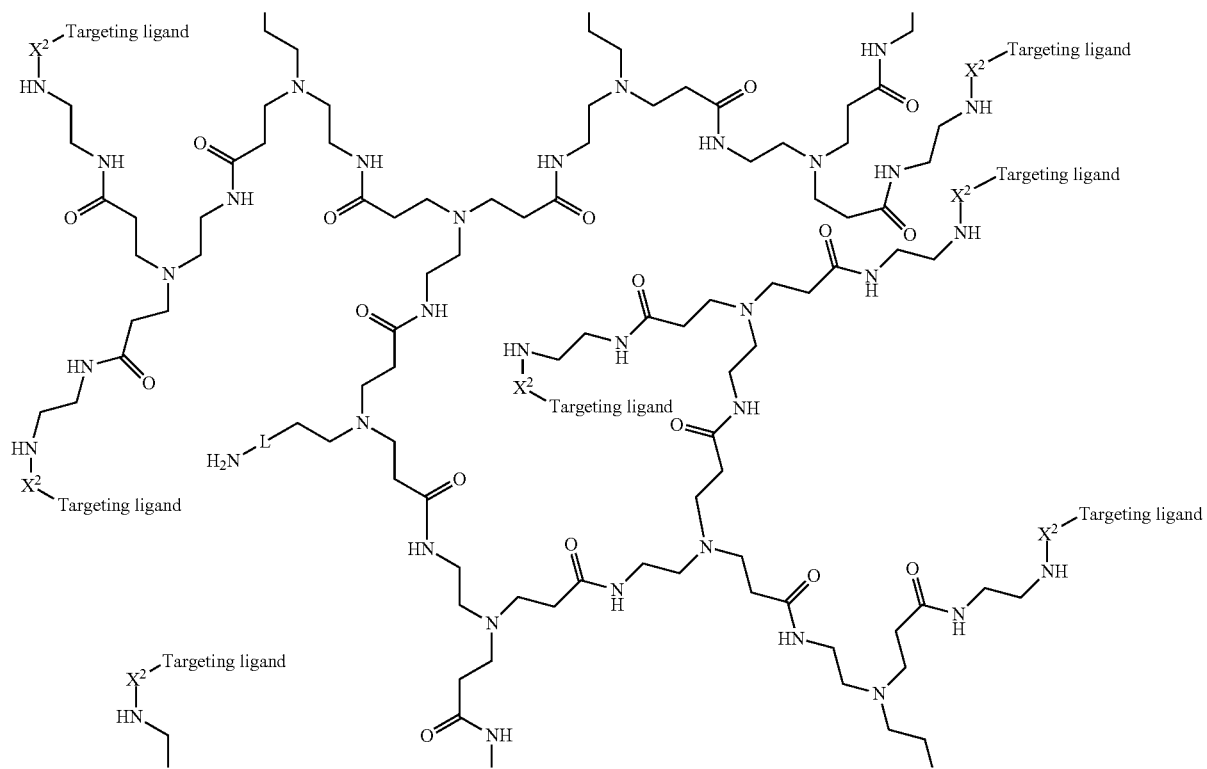

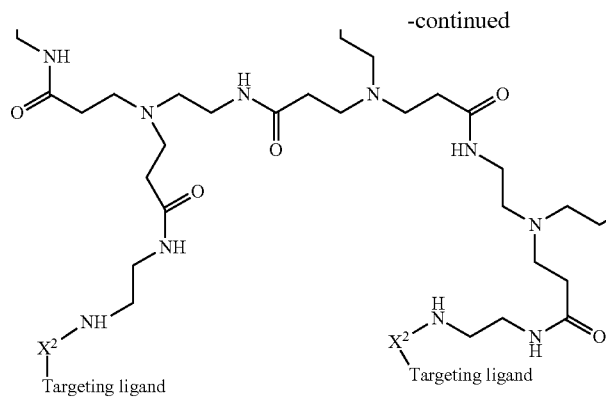
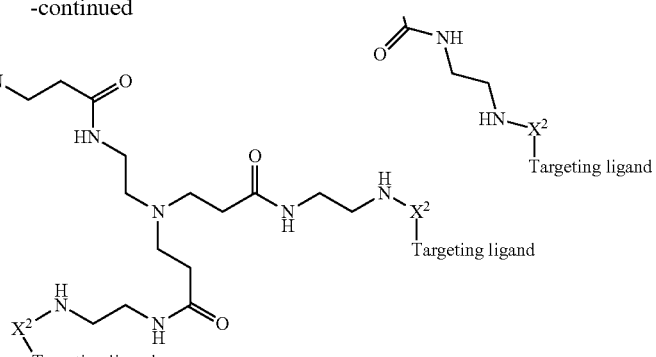

Those skilled in the art will recognize that protected and unprotected N-Boc-dendrimers of the Formulae (V)-(XII) may be represented by Formula (I) in which $R^1$ is $CO_2C(CH_3)_3$ (protected) or H (unprotected), $X^1$ is absent, n is zero or an integer in the range of 1 to 3, and each $R^2$ is independently a targeting ligand (e.g., folic acid). In various embodiments, $X^1$ is absent or a linker (e.g., $C_{1-4}$ alkylene or $C_{1-8}$ alkyleneoxide), each L is independently absent or selected from $C_{1-4}$ alkylene and $C_{1-8}$ alkyleneoxide; e.g., L can be independently absent or selected from the group consisting of —$CH_2$—, —$CH_2CH_2$—, —$CH_2CH_2CH_2$—, —$CH_2CH_2CH_2CH_2$—, —$OCH_2CH_2OCH_2CH_2$—, and —$CH_2OCH_2CH_2OCH_2CH_2OCH_2CH_2CH_2$—; $X^2$ is absent or a linker (e.g., $C_{1-4}$ alkylene or $C_{1-8}$ alkyleneoxide); and each targeting ligand is independently selected from the group consisting of folic acid, mannose, anisamide, RGD peptide, NGR peptide, galactosamine, antibody, antibody fragments, and protein.

Some embodiments of the compositions disclosed herein relate to asymmetrical dendritic compounds that can include an imaging agent and two targeting ligands. For example, the imaging agent can be selected from optical imaging agent and magnetic resonance imaging agent, and each of the targeting ligands can be independently selected from the group consisting of folic acid, mannose, anisamide, RGD peptide, NGR peptide, galactosamine, antibody, antibody fragment, and protein. Other embodiments of the compositions disclosed herein relate to dendrimers that can include an imaging agent and four targeting ligands. Other embodiments of the compositions disclosed herein relate to dendrimers that can include an imaging agent and eight targeting ligands. Other embodiments of the compositions disclosed herein relate to dendrimers that can include an imaging agent and sixteen targeting ligands. For example, the dendrimers can have the following structures as shown in Formulae (XIII)-(XVI):

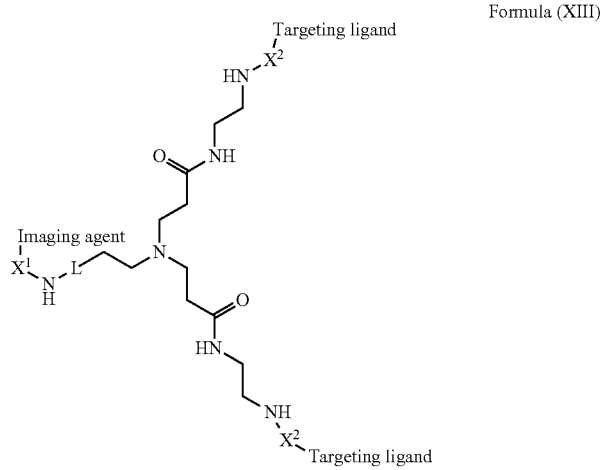

Formula (XIII)

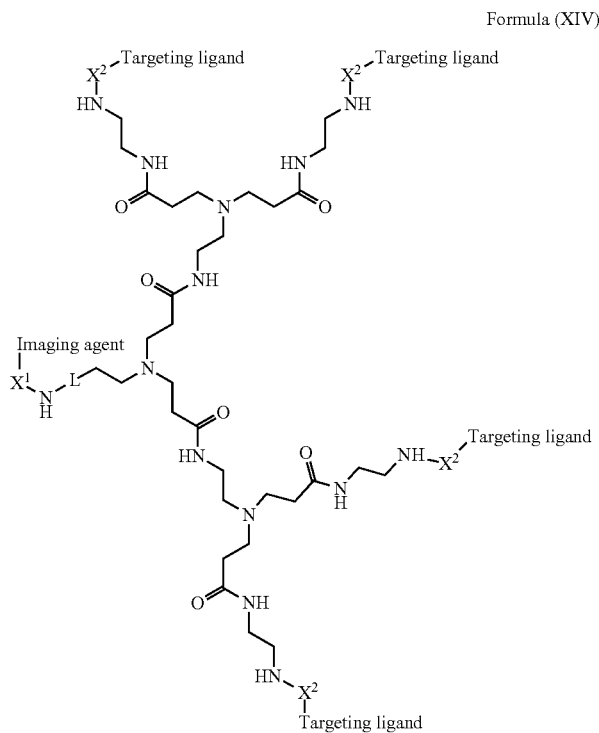

Formula (XIV)

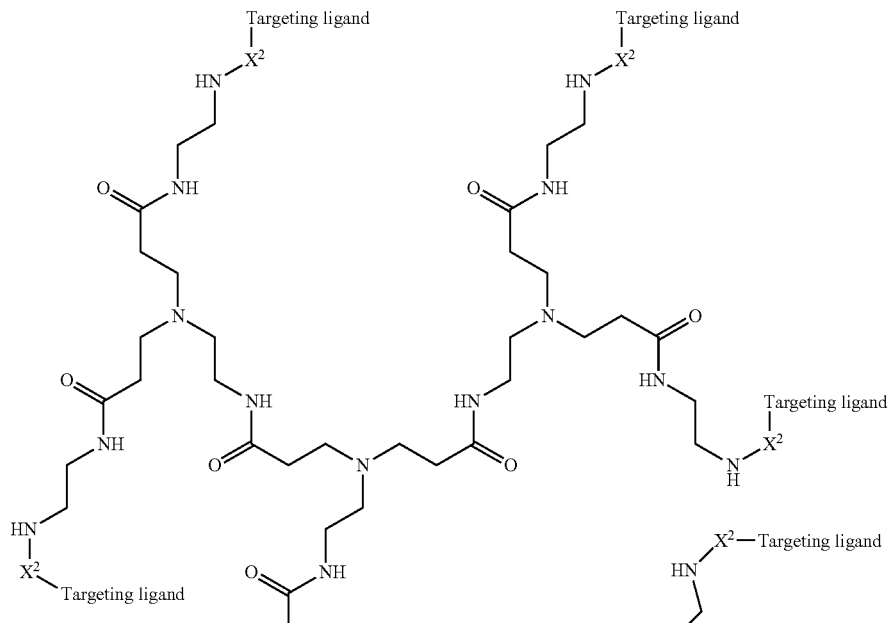
Formula (XV)
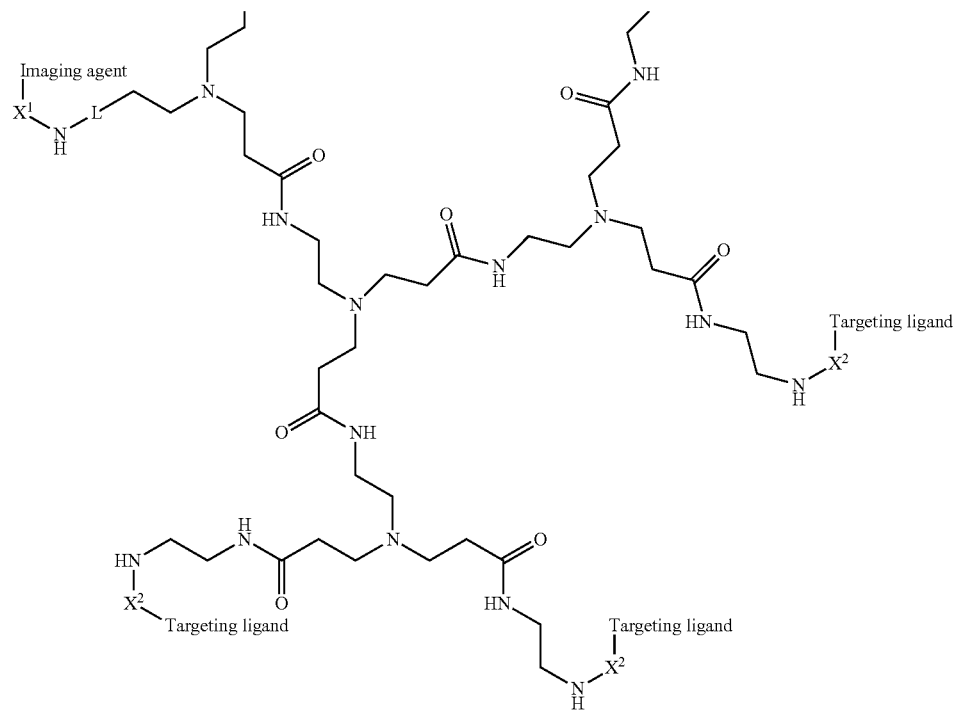

Formula (XVI)
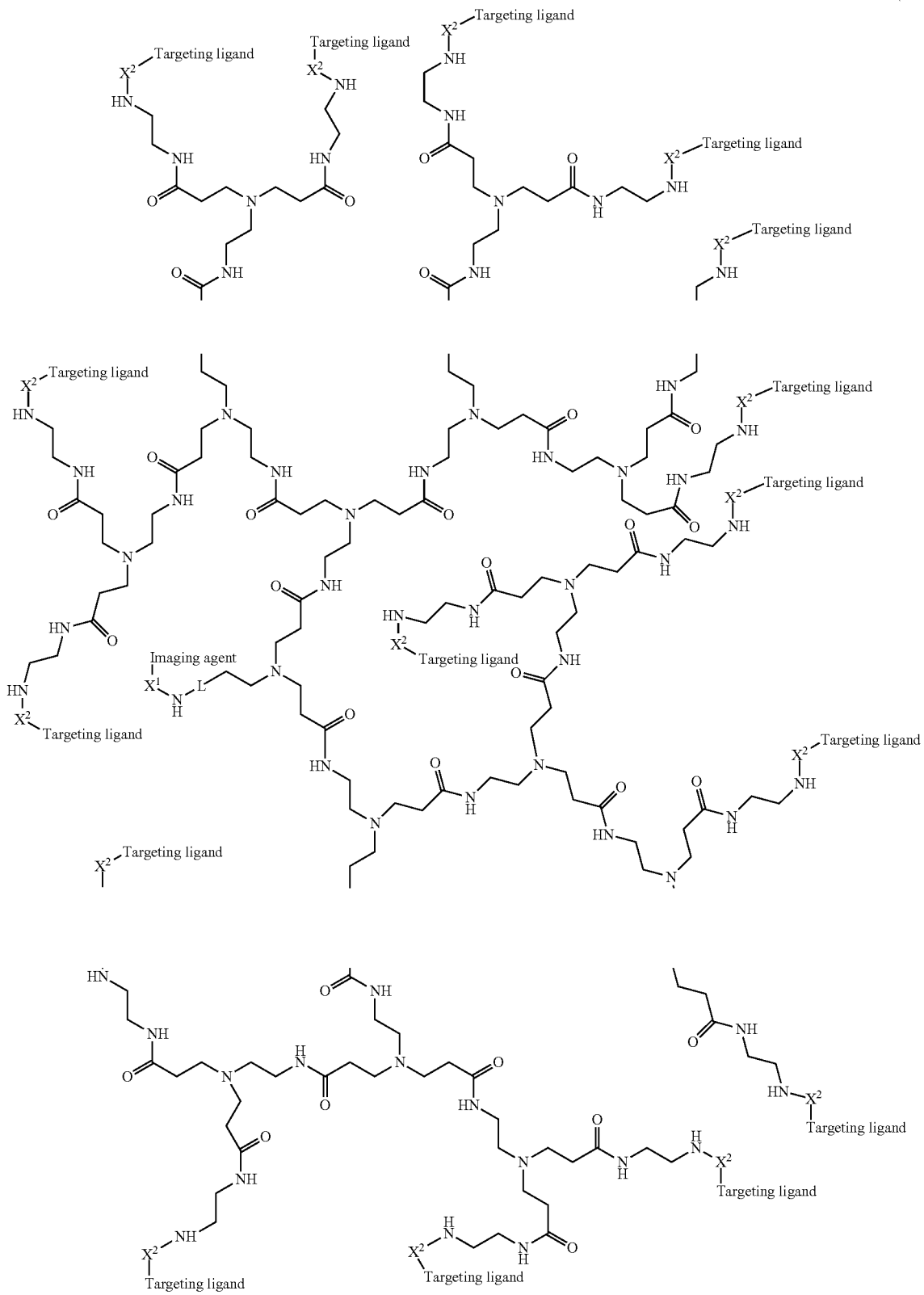

Those skilled in the art will recognize that asymmetrical dendritic compounds of the Formulae (XIII)-(XVI) may be represented by Formula (I) in which $R^1$ is an imaging agent, n is zero or an integer in the range of 1 to 3, and each $R^2$ is independently a targeting ligand (e.g., folic acid). In various embodiments, $X^1$ and $X^2$ are each independently absent or a linker (e.g., $C_{1-4}$ alkylene or $C_{1-8}$ alkyleneoxide), each L is independently absent or selected from $C_{1-4}$ alkylene and $C_{1-8}$ alkyleneoxide; e.g., L can be independently absent or selected from the group consisting of —$CH_2$—, —$CH_2CH_2$—, —$CH_2CH_2CH_2$—, —$CH_2CH_2CH_2CH_2$—, $OCH_2CH_2OCH_2CH_2$—, and —$CH_2OCH_2CH_2OCH_2CH_2OCH_2CH_2CH_2$—; and each targeting ligand is independently selected from the group consisting of folic acid, mannose, anisamide, RGD peptide, NGR peptide, galactosamine, antibody, antibody fragments, and protein.

Figure 5:
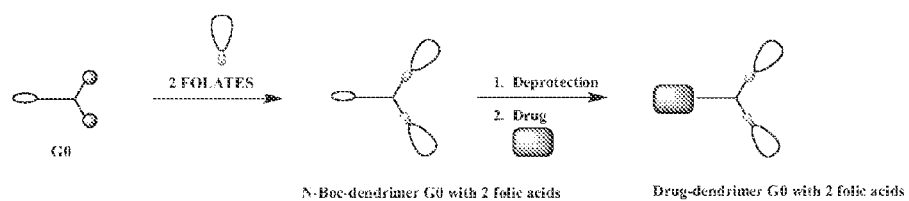
FIG. 5 is a schematic illustrating the conjugation of two folic acids onto N-Boc-dendrimer G0, which generates one product N-Boc-dendrimer with 2 folic acids. The product is further conjugated with a drug to become a drug-dendrimer with 2 folic acid targeting ligands.
Figure 6:
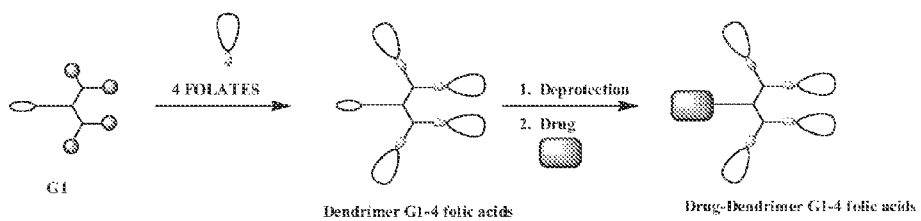
FIG. 6 is a schematic illustrating the conjugation of four folic acids onto N-Boc-dendrimer G1, which generates one product N-Boc-dendrimer with 4 folic acids. The product is further conjugated with a drug to become a drug-dendrimer with 4 folic acid targeting ligands.
Figure 7:
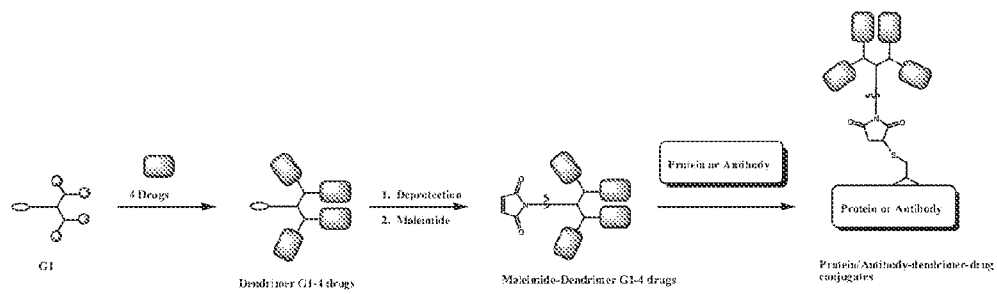
FIG. 7 is a schematic illustrating the conjugation of 4 drugs onto N-Boc-dendrimer G0, which generates one product N-Boc-dendrimer with 4 attached drugs. The product is further conjugated with a maleimide group to become a maleimide-dendrimer with 4 attached drugs, then further conjugated with protein and/or antibody to form a protein/antibody-dendrimer-drug conjugate.

Some embodiments of the compositions disclosed herein relate to dendrimers that can include a drug and two targeting ligands. For example, FIG. 5 schematically illustrates the conjugation of two folic acid targeting agents with a G0 N-Boc dendrimer to form a G0 N-Boc dendrimer with 2 folic acid ligands, followed by deprotection (conversion of N-Boc to amine) and conjugation with a drug to form a G0 drug-dendrimer with 2 folic acid ligands. Similarly, FIG. 6 schematically illustrates the conjugation of four folic acid targeting agents with a G1 N-Boc dendrimer to form a G1 N-Boc dendrimer with 4 folic acid ligands, followed by deprotection and conjugation with a drug to form a G1 drug-dendrimer with 4 folic acid ligands. Likewise, FIG. 7 schematically illustrates the conjugation of four drugs with a G1 N-Boc dendrimer to form a G1 N-Boc dendrimer with 4 drugs, followed by deprotection and conversion of the resulting amine to a maleimide group, followed by conjugation with a protein or antibody to form a G1 protein/antibody-dendrimer drug conjugate.

Various drugs can be attached to the asymmetrical dendritic compounds of the Formula (I) described herein. For example, the drug can be an anticancer drug, for example an anticancer drug selected from the group consisting of doxorubicin, platinum, paclitaxel, docetaxel, combretastin A-4, vinblastine, vincristine, vinorelbine, camptothecin, SN-38, etoposide, teniposide, auristatin, calicheamicin, maytansinoid, and duocarmycin. Each of the targeting ligands can be independently selected from the group consisting of folic acid, mannose, anisamide, RGD peptide, NGR peptide, galactosamine, antibody, antibody fragment, and protein. Other embodiments of the compositions disclosed herein relate to dendrimers that can include a drug and four targeting ligands. Other embodiments of the compositions disclosed herein relate to dendrimers that can include a drug and eight targeting ligands. Other embodiments of the compositions disclosed herein relate to dendrimers that can include a drug and sixteen targeting ligands. For example, the dendrimers can have the following structures as shown in Formulae (XVII)-(XX):

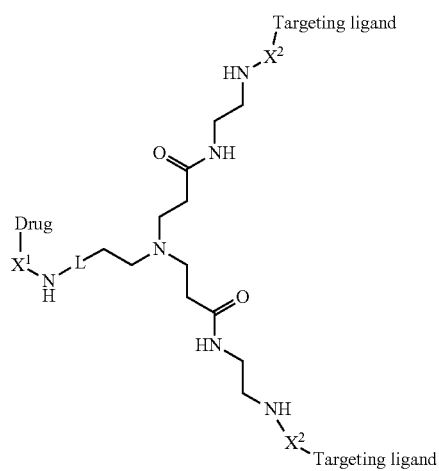

Formula (XVII)

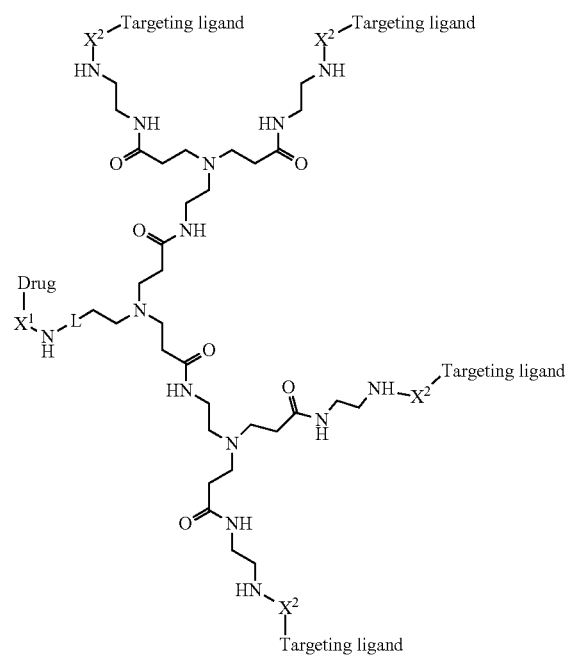

Formula XVIII)

-continued
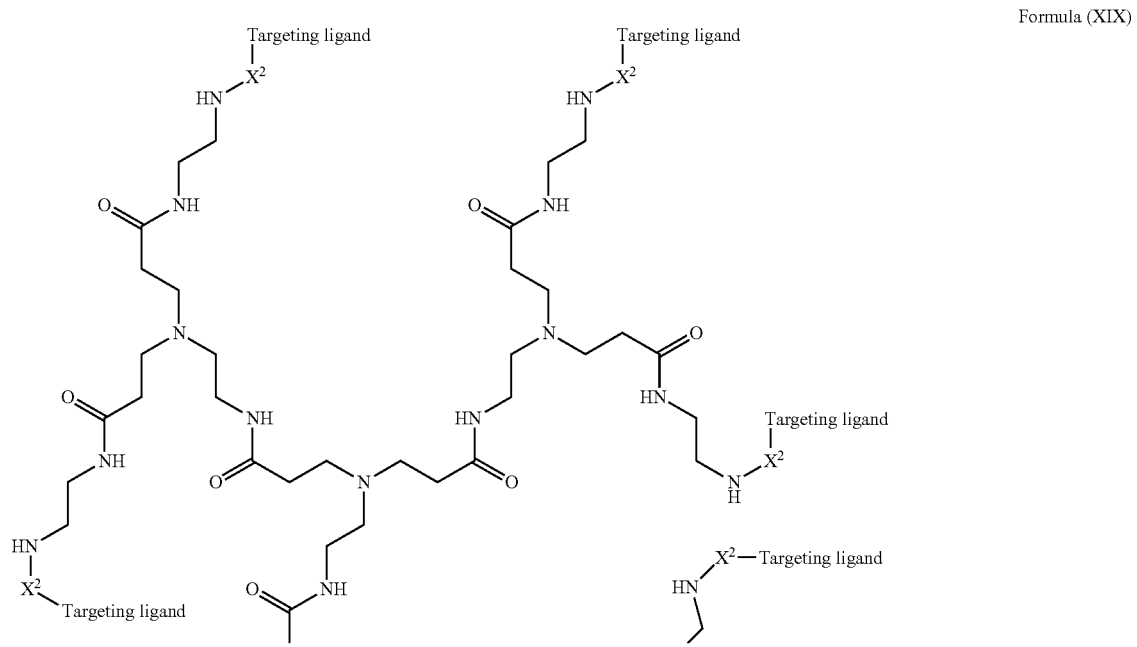
Formula (XIX)
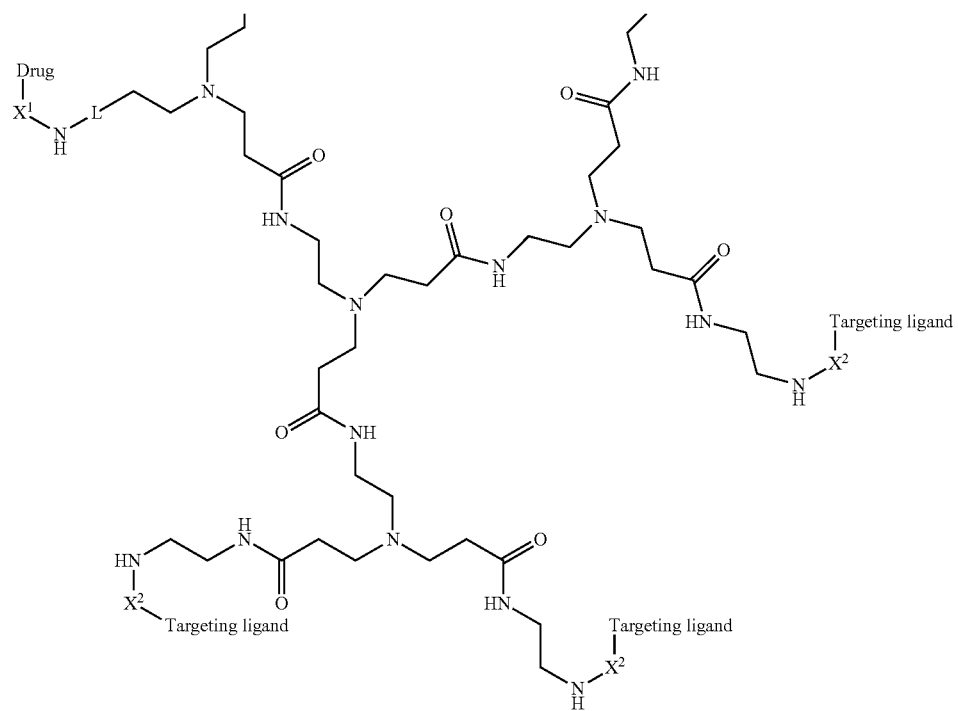

-continued

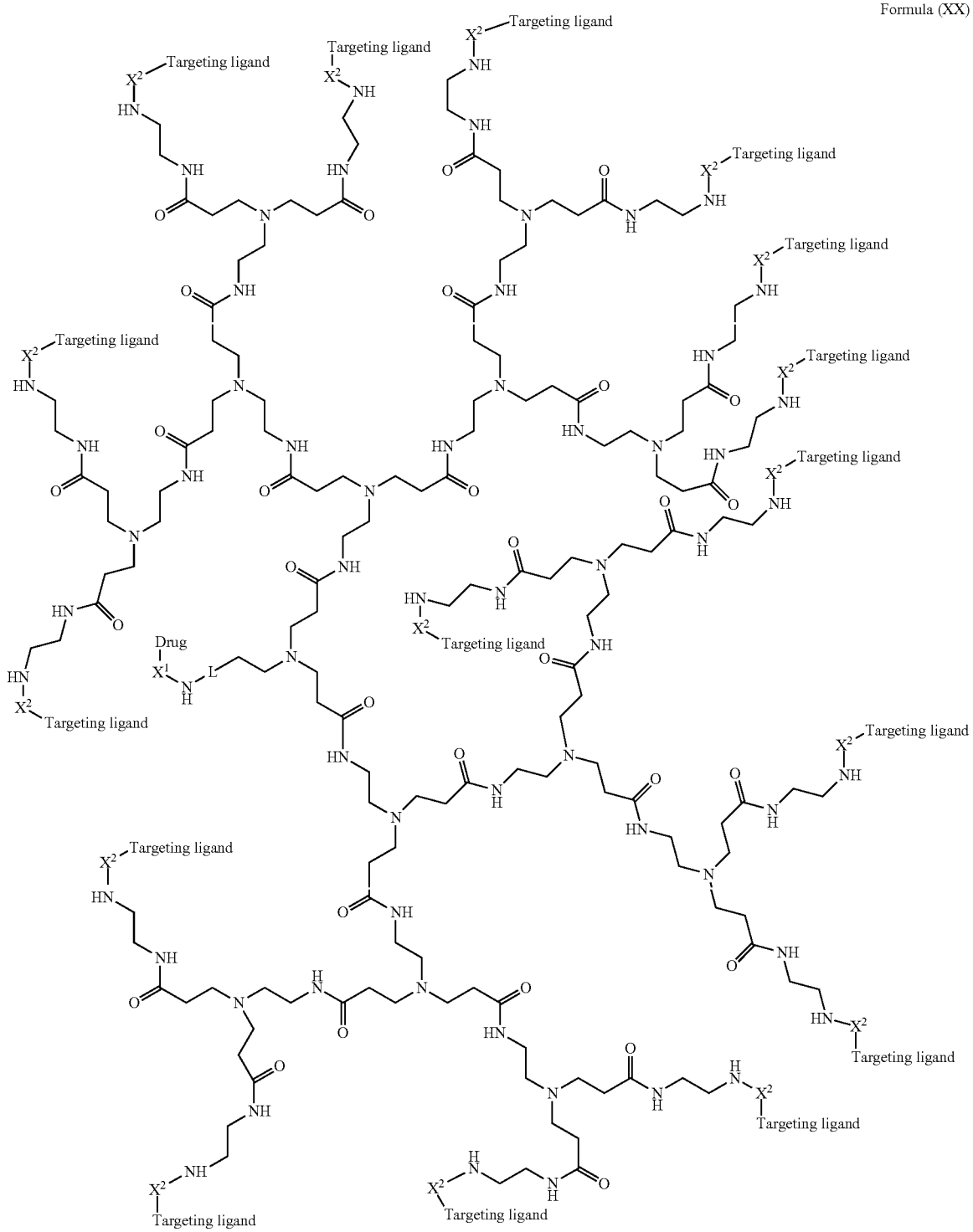

Formula (XX)

Those skilled in the art will recognize that asymmetrical dendritic compounds of the Formulae (XVII)-(XX) may be represented by Formula (I) in which $R^1$ is a drug, n is zero or an integer in the range of 1 to 3, and each $R^2$ is independently a targeting ligand (e.g., folic acid). In various embodiments, the drug is an anticancer drug; $X^1$ and $X^2$ are each independently absent or a linker (e.g., $C_{1-4}$ alkylene and $C_{1-8}$ alkyleneoxide), and each L is independently absent or selected from $C_{1-4}$ alkylene and $C_{1-8}$ alkyleneoxide; e.g., L can be independently absent or selected from the group consisting of —$CH_2$—, —$CH_2CH_2$—, —$CH_2CH_2CH_2$—, —$CH_2CH_2CH_2CH_2$—, —$OCH_2CH_2OCH_2CH_2$—, and —$CH_2OCH_2CH_2OCH_2CH_2OCH_2CH_2$—. For example, the drug can be selected from the group consisting of doxorubicin, platinum, SN-38, paclitaxel, docetaxel, combretastin A-4, vinblastine, vincristine, vinorelbine, camptothecin, etoposide, teniposide, auristatin, calicheamicin, maytansinoid, and duocarmycin; and the targeting ligands can be selected from the group consisting of folic acid, mannose, anisamide, RGD peptide, NGR peptide, galactosamine, antibody, antibody fragment, and albumin protein.

Some embodiments of the compositions disclosed herein relate to N-Boc-dendrimers that can include two folate ligands. Other embodiments of the compositions disclosed herein relate to N-Boc-dendrimers that can include four folate ligands. Other embodiments of the compositions disclosed herein relate to N-Boc-dendrimers that can include eight folate ligands. Other embodiments of the compositions disclosed herein relate to N-Boc-dendrimers that can include sixteen folate ligands. The N-Boc-dendrimers can be in their protected or deprotected form. For example, the dendrimers can have the following structures as shown in Formulae (XXI)-(XXVIII):

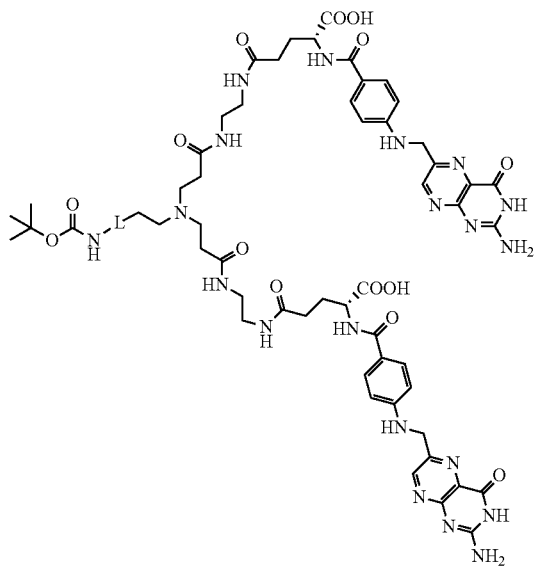

Formula (XXI)

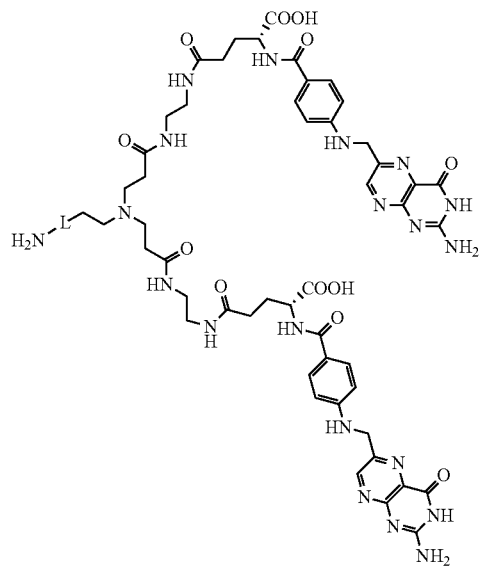

Formula (XXII)

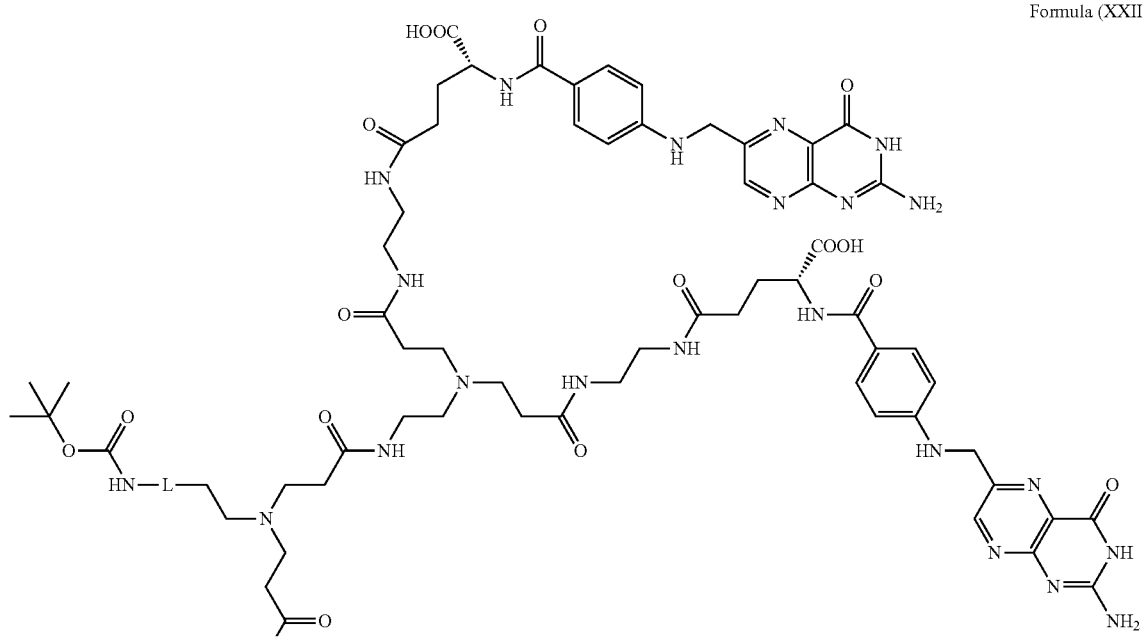

Formula (XXIII)

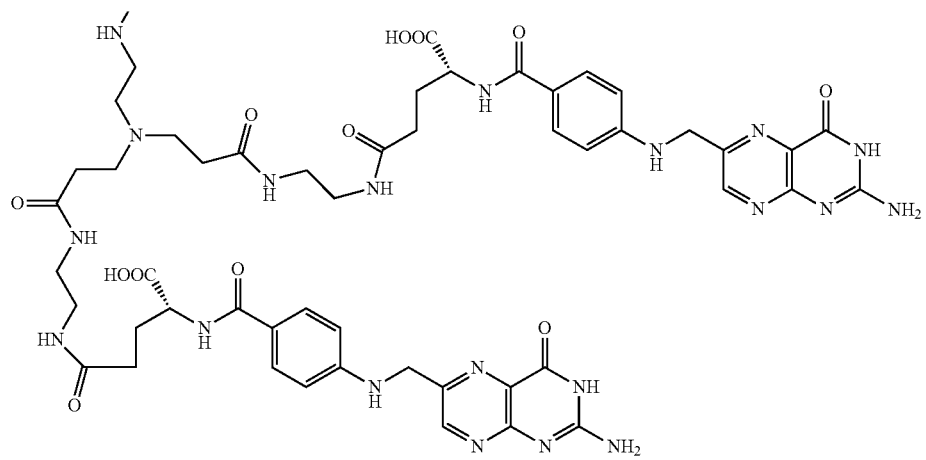
Formula (XXIV)
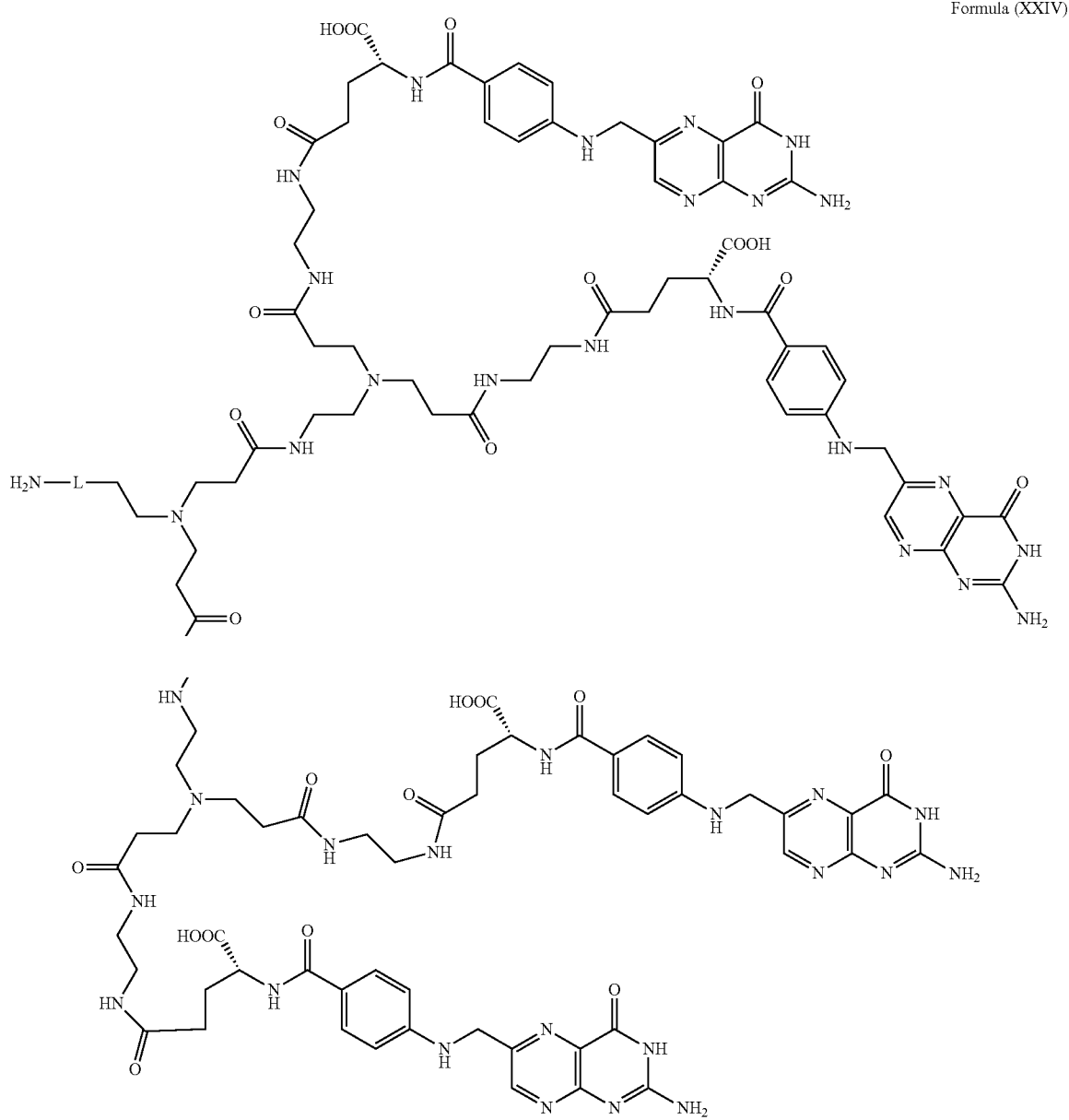

Formula (XXV)
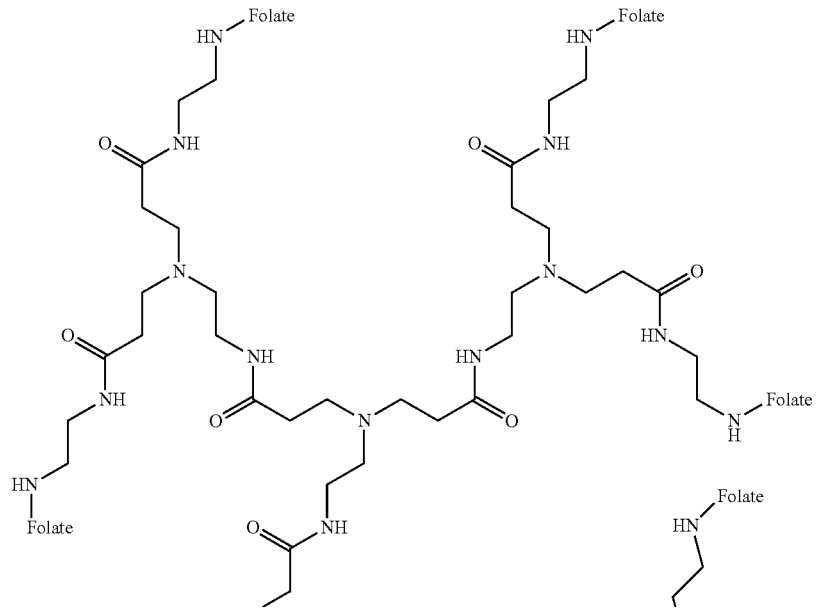
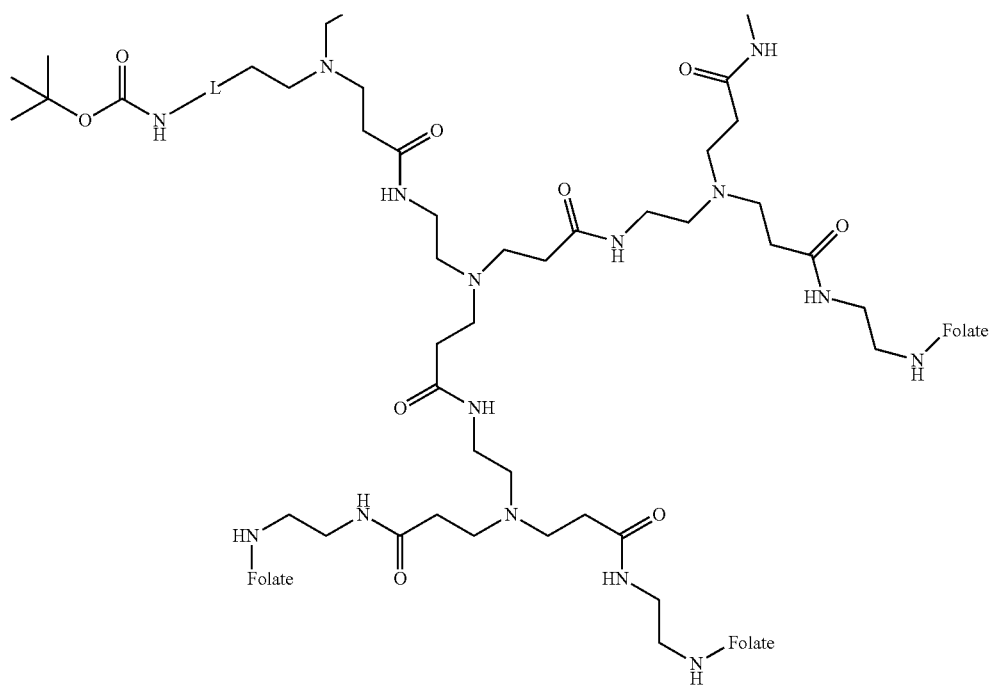
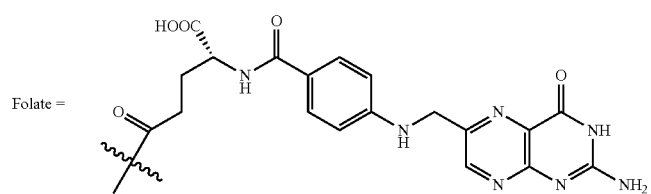

Formula (XXVI)
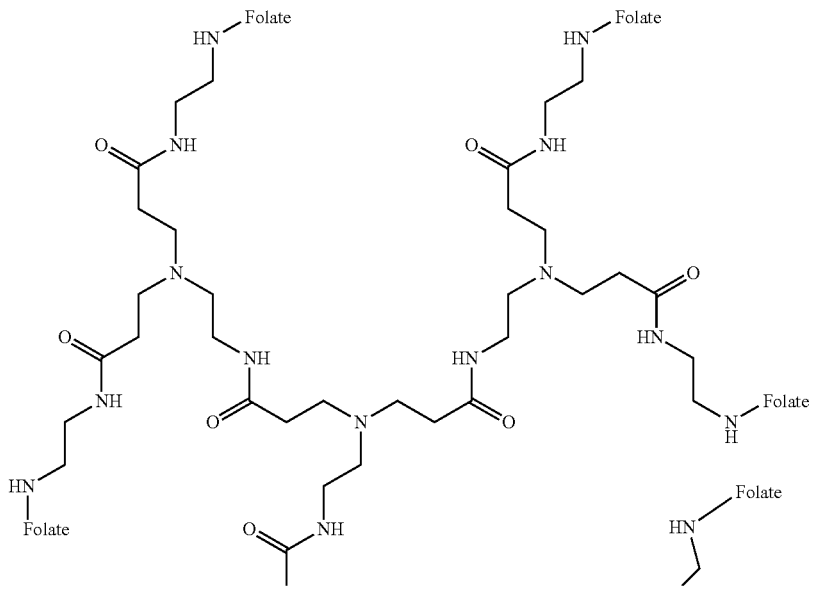
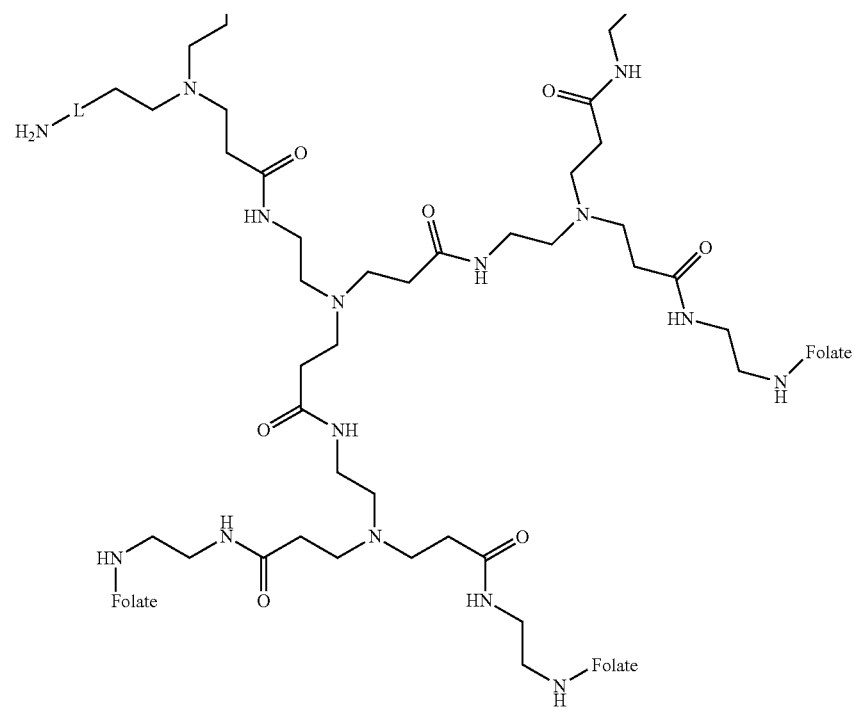
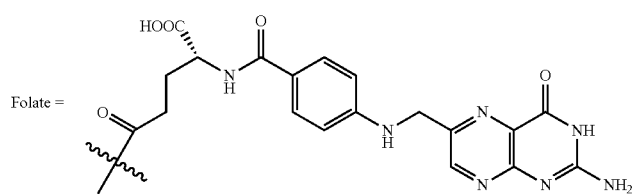

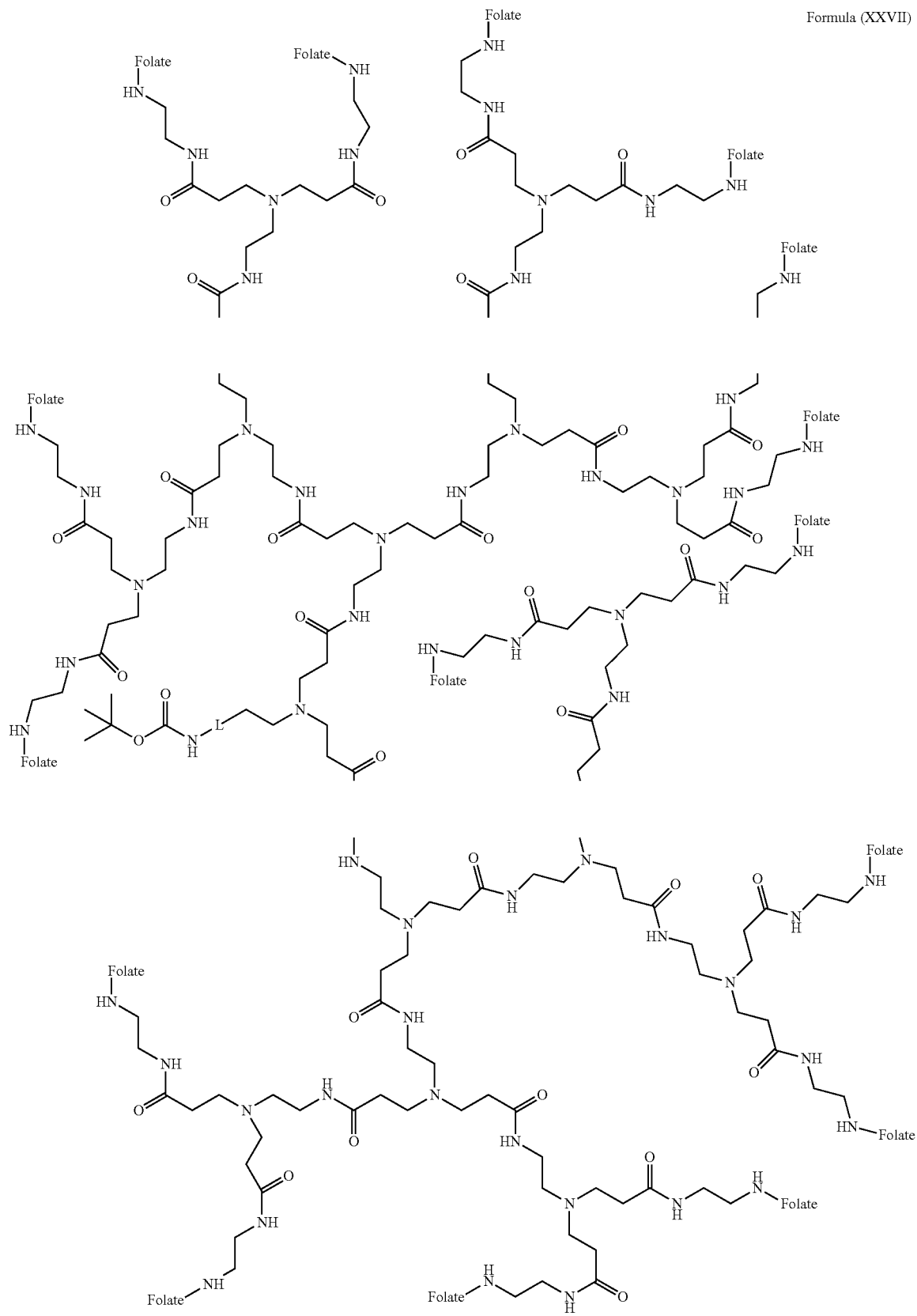
Formula (XXVII)

Formula (XXVIII)
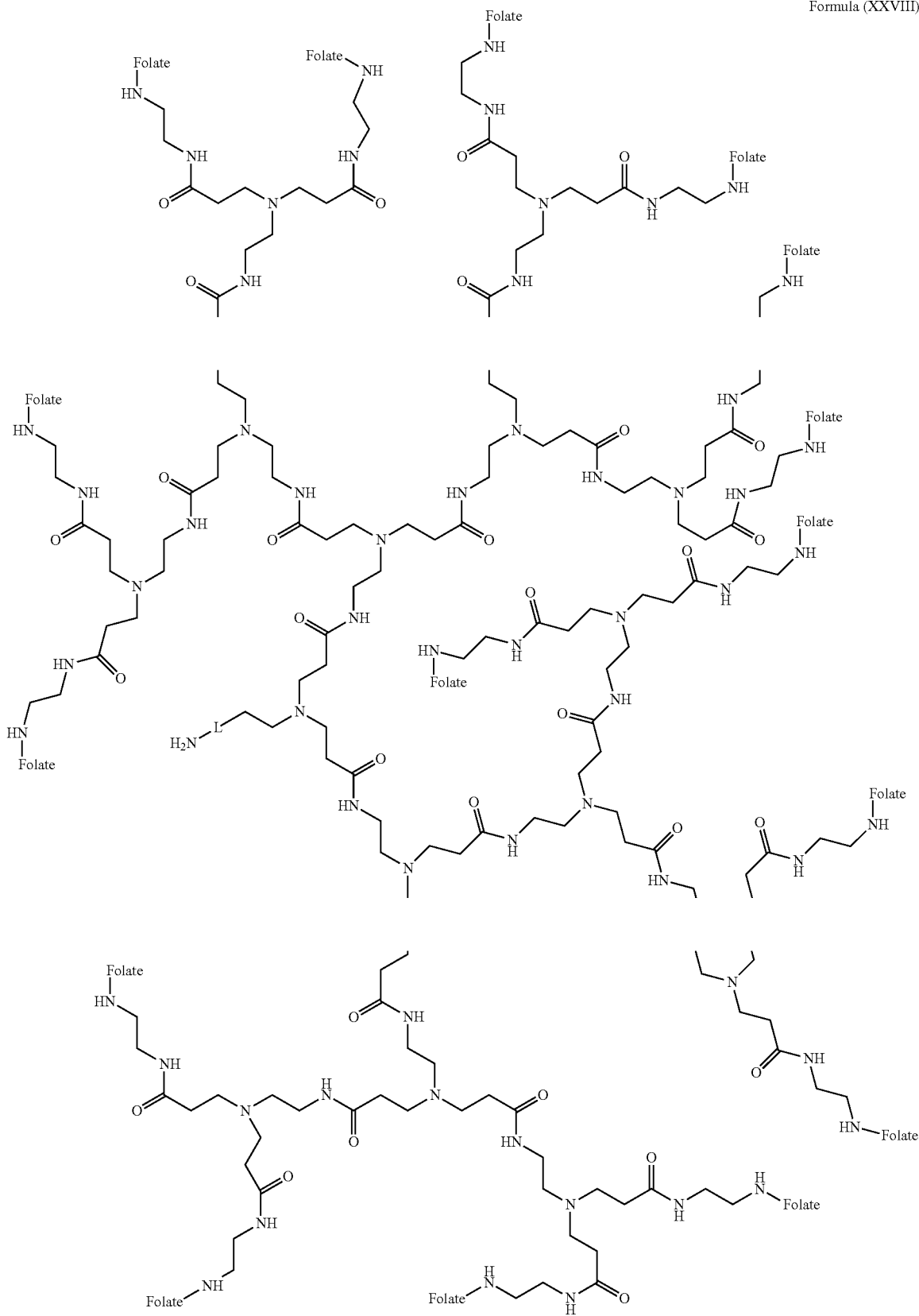

Those skilled in the art will recognize that asymmetrical dendritic compounds of the Formulae (XXI)-(XXVIII) may be represented by Formula (I) in which $R^1$ is $CO_2C(CH_3)_3$ (protected) or H (unprotected), $X^1$ and $X^2$ are absent; n is zero or an integer in the range of 1 to 3, and each $R^2$ is folic acid. In various embodiments, each L is independently absent or selected from $C_{1-4}$ alkylene and $C_{1-8}$ alkyleneoxide; e.g., L can be absent or selected from the group consisting of —$CH_2$—, —$CH_2CH_2$—, —$CH_2CH_2CH_2$—, —$CH_2CH_2CH_2CH_2$—, —$OCH_2CH_2OCH_2CH_2$—, and —$CH_2OCH_2CH_2OCH_2CH_2OCH_2CH_2$—.

Various embodiments described herein relate to therapeutic agents that include an asymmetrical dendritic compound that contains an imaging agent and/or a drug. In an embodiment, the therapeutic agent is represented by the Formula (I) wherein: Gn is a dendritic PAMAM group, having a core group and a shell group, for which n is zero or an integer in the range of 1 to 3 that specifies the generation of the dendritic PAMAM group; $R^1$—$X^1$—NH-L is a group attached to the core group, wherein $R^1$ is selected from a targeting ligand, a drug (e.g., an anticancer drug), and an imaging agent; $X^1$ is absent or selected from $C_{1-4}$ alkylene and $C_{1-8}$ alkyleneoxide; L is absent or selected from $C_{1-4}$ alkylene and $C_{1-4}$ alkyleneoxide; (NH—$X^2$—$R^2$)$_m$ is a terminal group attached to the shell group, wherein m is 2, 4, 8 or 16 and specifies the number of the attached NH—$X^2$—$R^2$ terminal groups; each $X^2$ is independently absent or selected from $C_{1-4}$ alkylene and $C_{1-8}$ alkyleneoxide; each $R^2$ is independently selected from a targeting ligand, a drug (e.g., an anticancer drug), and an imaging agent; and each $R^2$ is different from $R^1$. In some embodiments, one of $R^1$ and $R^2$ comprises a targeting ligand and the other of $R^1$ and $R^2$ comprises an anticancer drug or an imaging agent. For example, in some embodiments, $R^1$ comprises an anticancer drug and $R^2$ comprises a folic acid targeting ligand. In other embodiments, $R^1$ comprises an imaging agent.

Some embodiments of the compositions disclosed herein relate to asymmetrical dendritic compounds that can include an imaging agent or a drug and two folate ligands. Other embodiments of the compositions disclosed herein relate to dendrimers that can include an imaging agent or a drug and four folate ligands. Other embodiments of the compositions disclosed herein relate to dendrimers that can include an imaging agent or a drug and eight folate ligands. Other embodiments of the compositions disclosed herein relate to dendrimers that can include an imaging agent or a drug and sixteen folate ligands. For example, the dendrimers can have the following structures as shown in Formulae (XXIX)-(XXXVI):

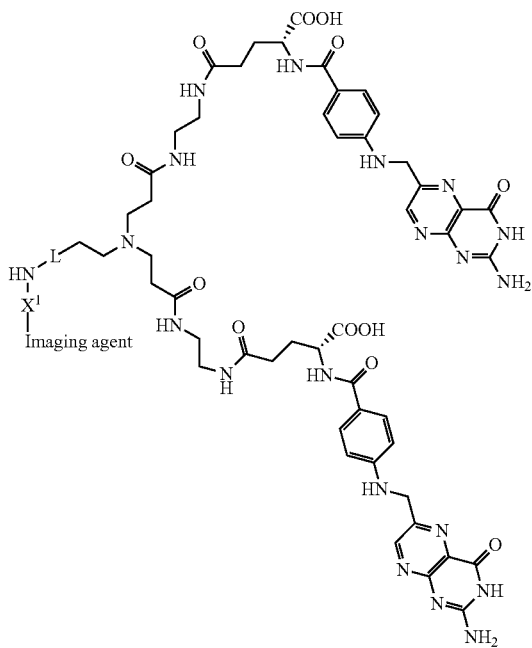

Formula (XXIX)

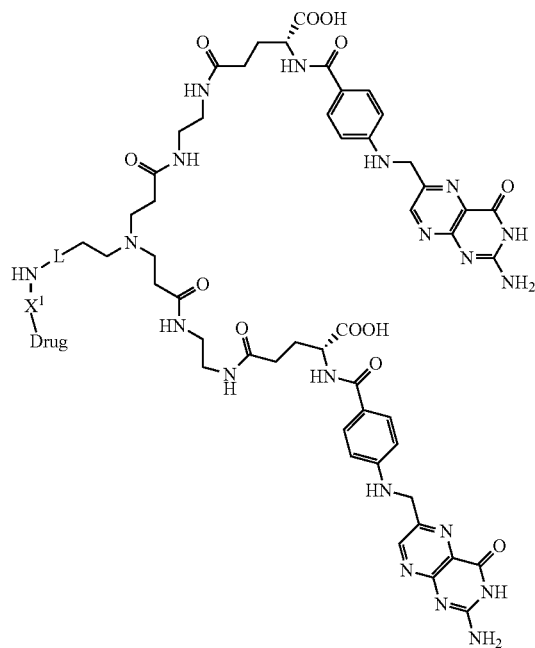

Formula (XXX)

Formula (XXXI)
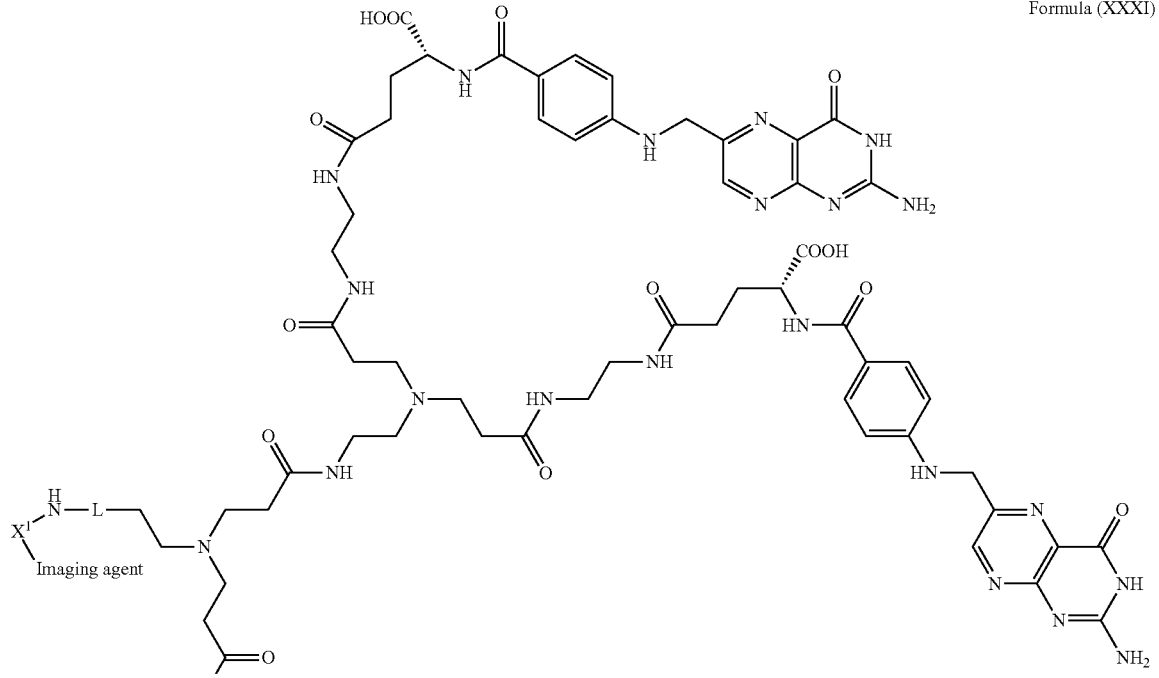
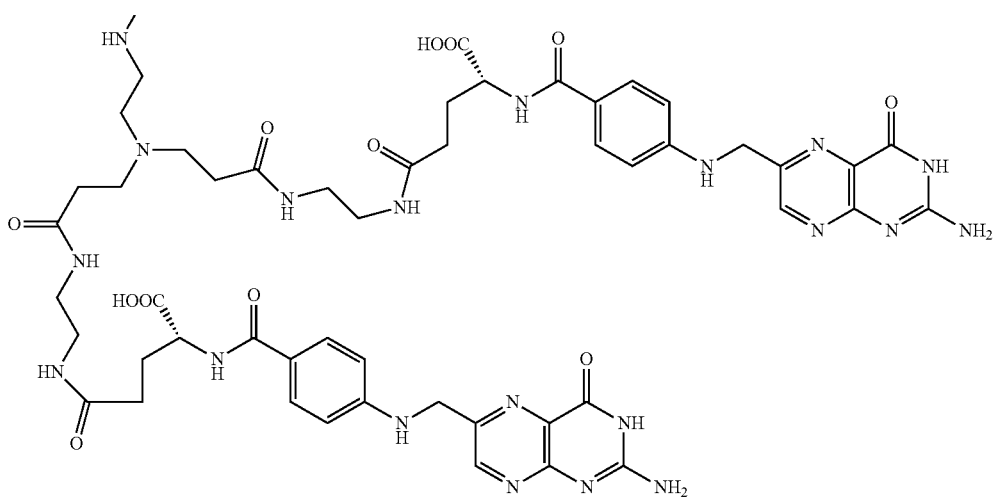

-continued
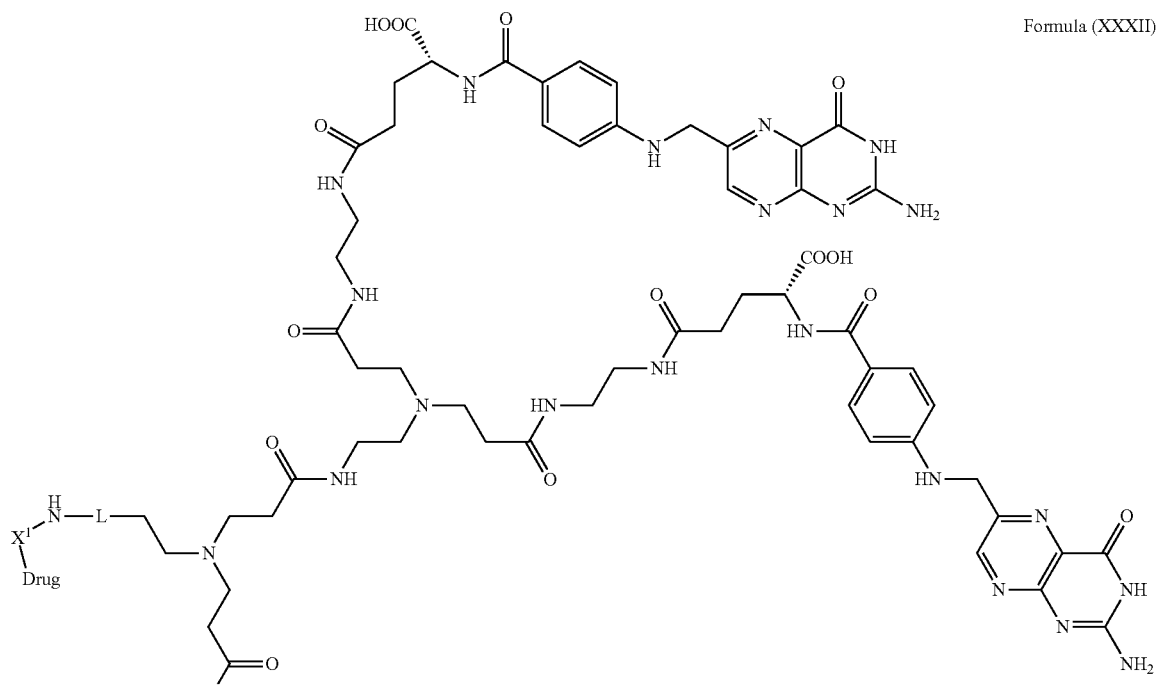
Formula (XXXII)
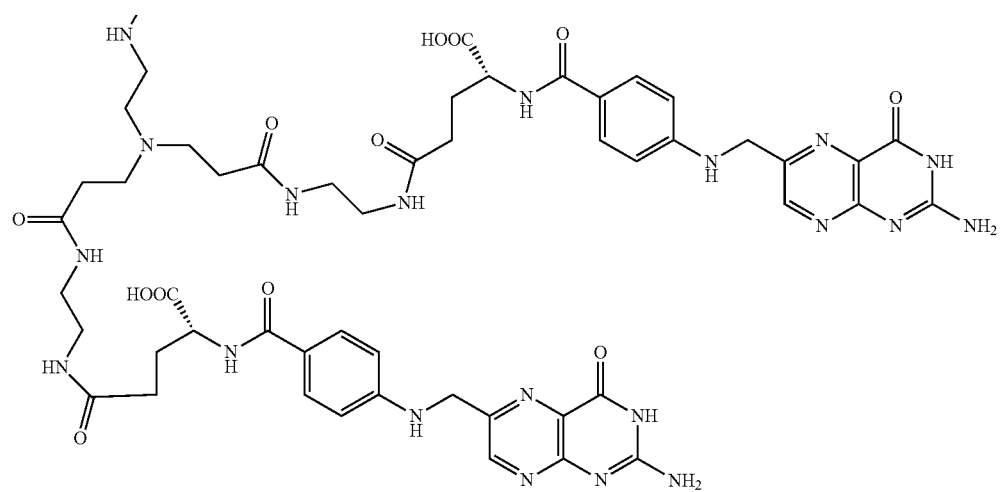

Formula (XXXIII)
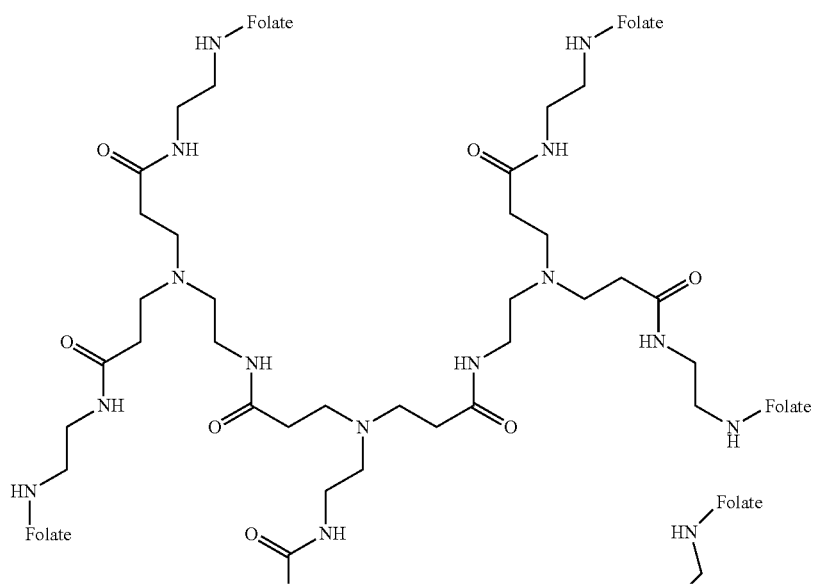
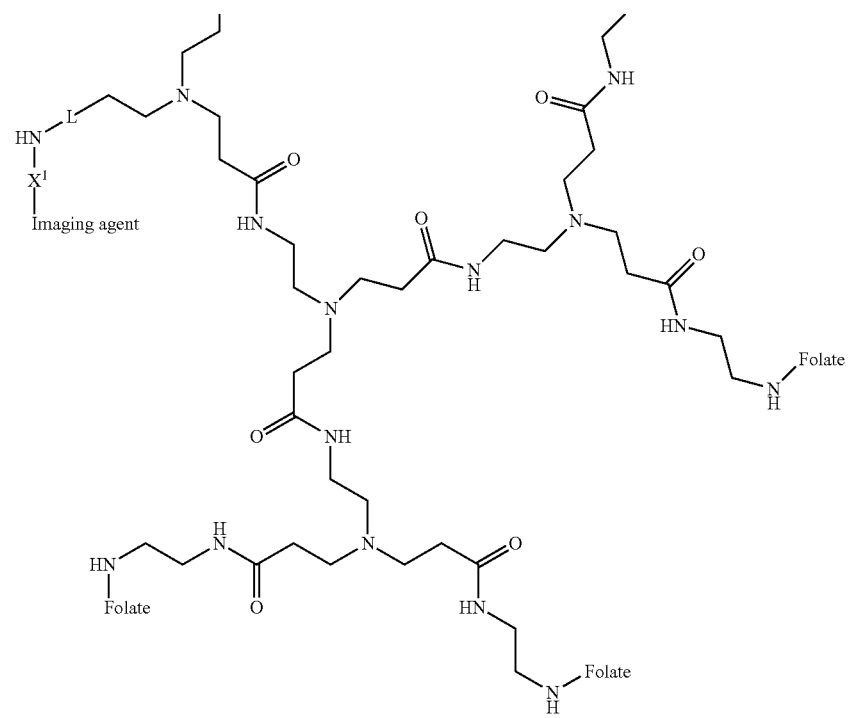
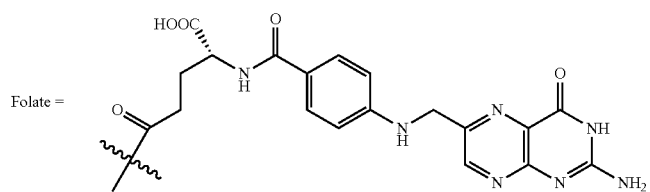

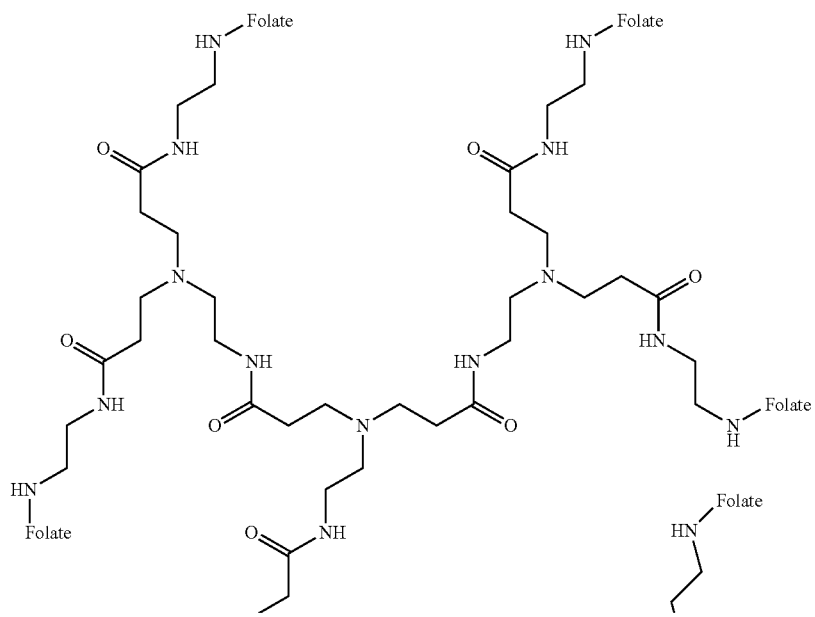
Formula (XXXIV)
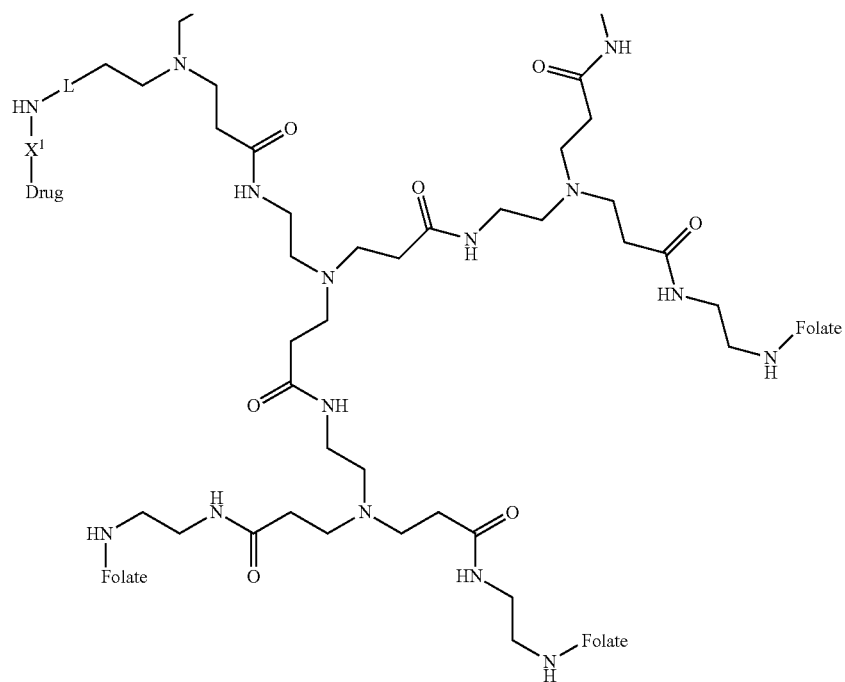
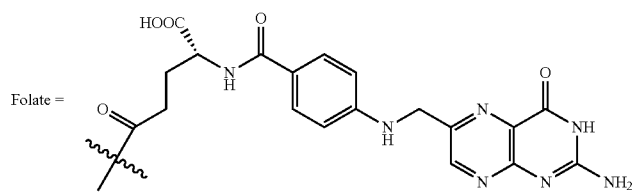

Formula (XXXV)
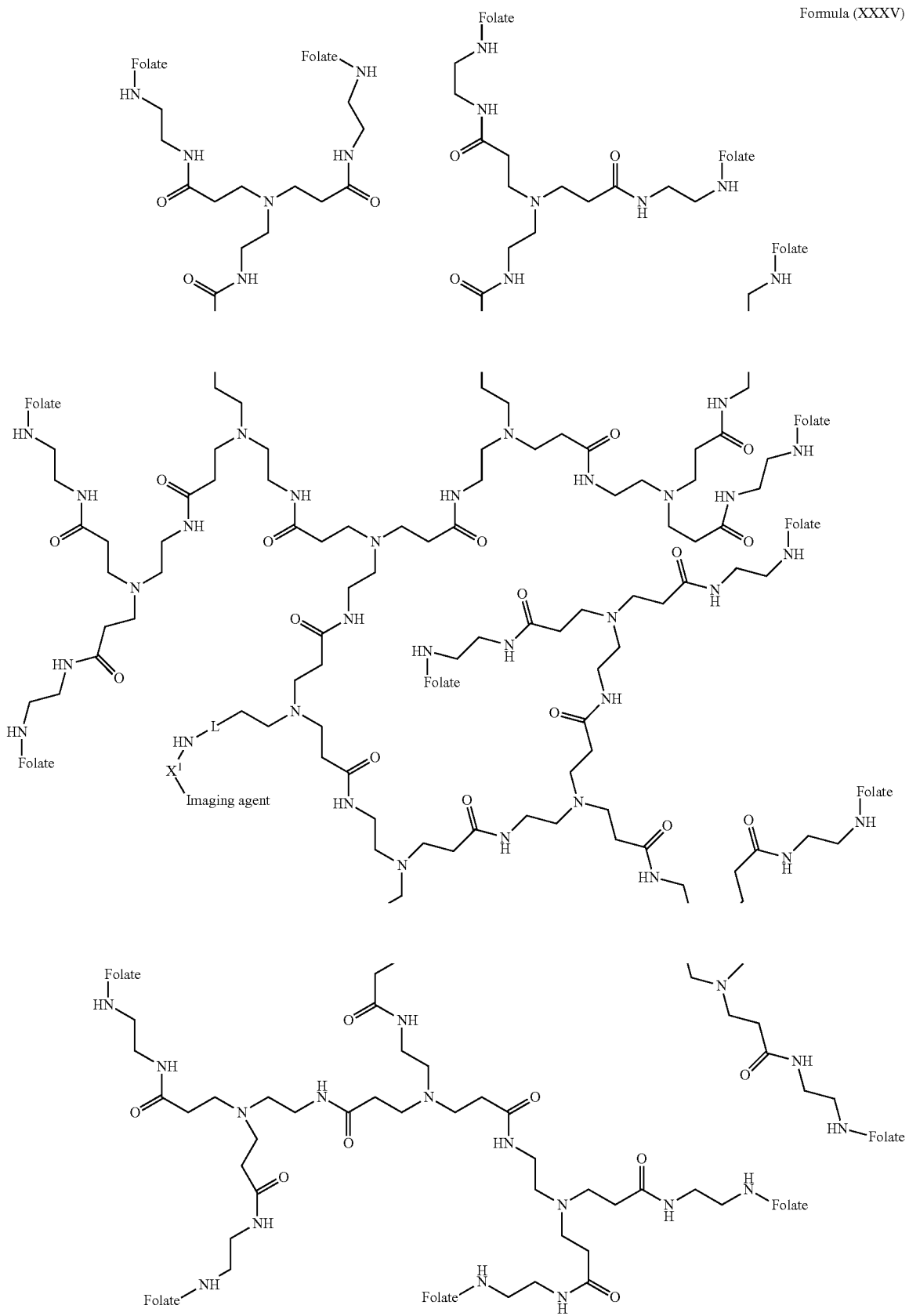

-continued

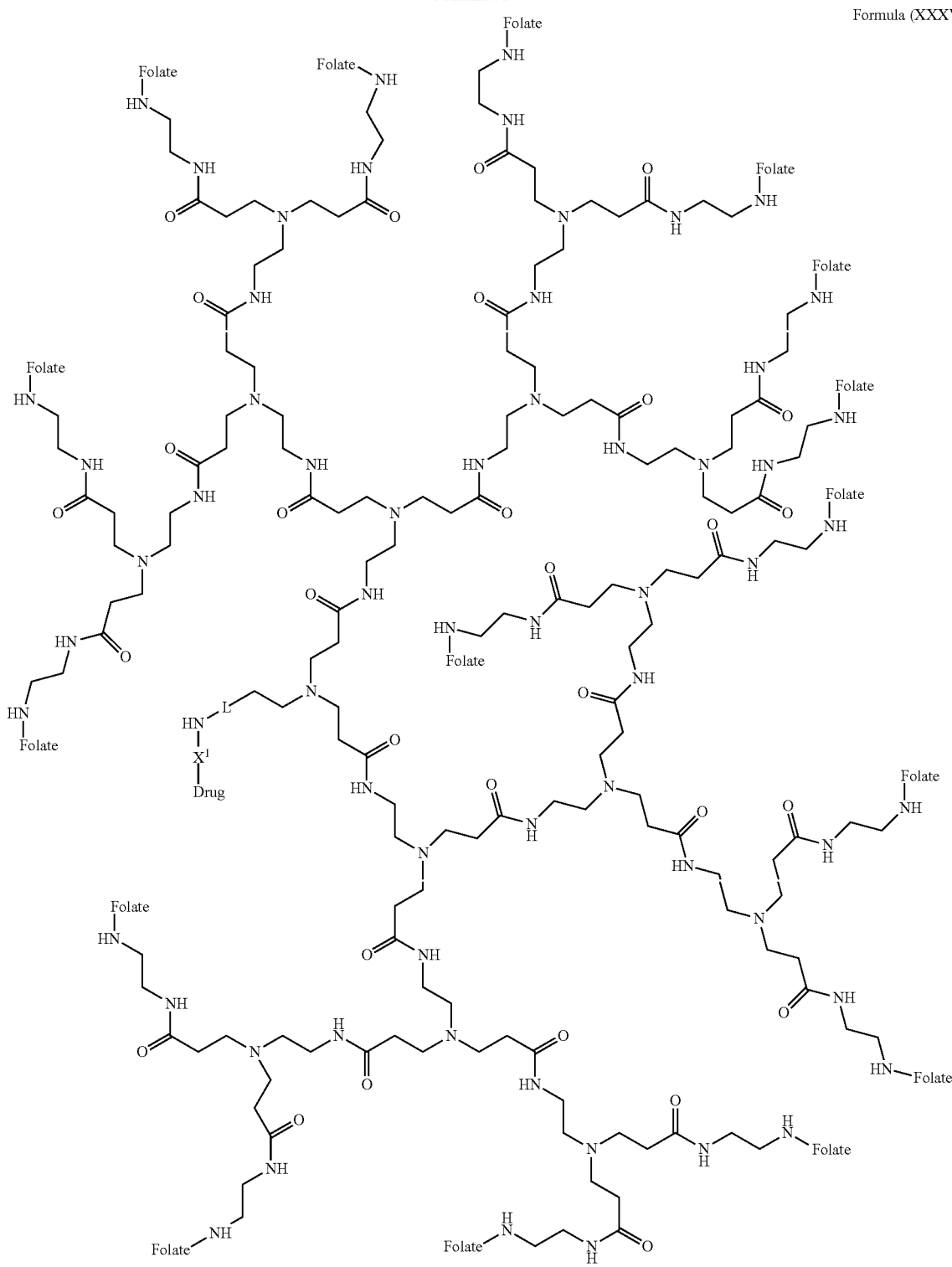

Formula (XXXVI)

Those skilled in the art will recognize that asymmetrical dendritic compounds of the Formulae (XXIX)-(XXXVI) may be represented by Formula (I) in which $R^1$ is a drug or imaging agent, $X^2$ is absent; n is zero or an integer in the range of 1 to 3, and each $R^2$ is folic acid (also referred to herein as folate). In various embodiments, L is independently absent or selected from $C_{1-4}$ alkylene and $C_{1-8}$ alkyleneoxide; e.g., each L can be independently absent or selected from the group consisting of $-CH_2-$, $-CH_2CH_2-$, $-CH_2CH_2CH_2-$, $-CH_2CH_2CH_2CH_2-$, $-OCH_2CH_2OCH_2CH_2-$, and $-CH_2OCH_2CH_2OCH_2CH_2OCH_2CH_2CH_2-$; the drug is an anticancer drug selected from the group consisting of doxorubicin, platinum, SN-38, paclitaxel, docetaxel, combretastin A-4, vinblastine, vincristine, vinorelbine, camptothecin, etoposide, teniposide, auristatin, calicheamicin, maytansinoid, and duocarmycin; and each imaging agent is independently selected from the group consisting of an optical imaging agent and a magnetic resonance imaging agent.

Some embodiments of the compositions disclosed herein relate to asymmetrical dendritic compounds that can include an imaging agent or a drug and multiple (e.g., 2, 4, 8 or 16) folate ligands. In these embodiments, the shell group of the dendritic PAMAM group is modified to include an $X^3$ linking group in place of the —$(CH_2)_2$— linkage between NH groups, e.g., as illustrated in Formulae (XXXVII)-(XLII). In various embodiments the dendrimers can include an imaging agent or a drug and four folate ligands. In other embodiments the dendrimers can include an imaging agent or a drug and eight folate ligands; or an imaging agent or a drug and sixteen folate ligands. For example, the dendrimers can have the following structures as shown in Formulae (XXXVII)-(XLII):

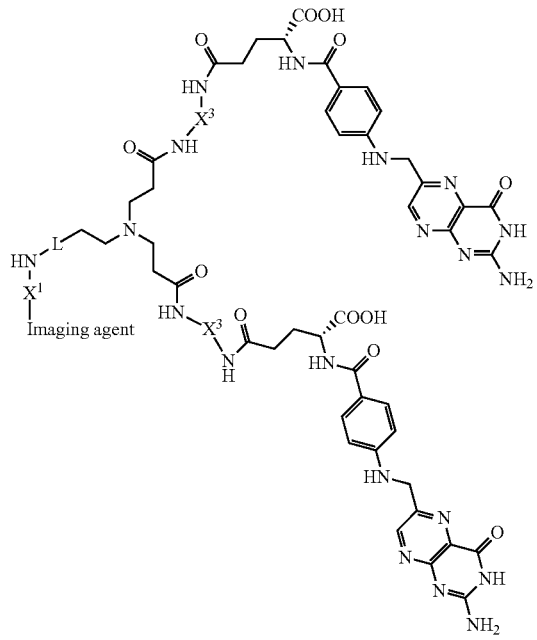

Formula (XXXVII)

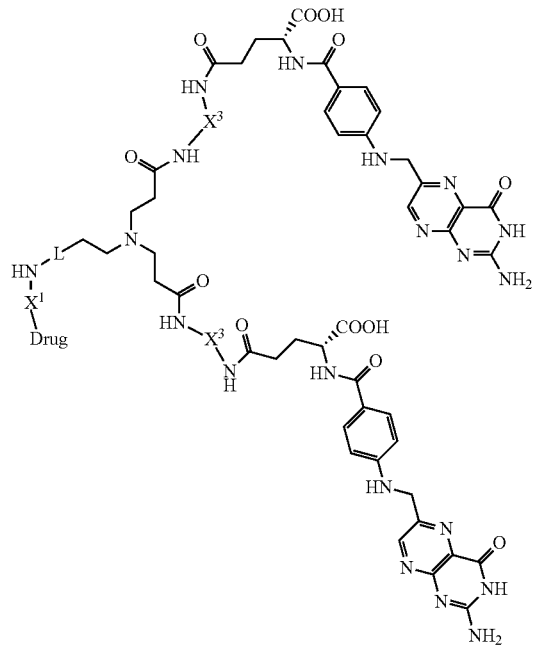

Formula (XXXVIII)

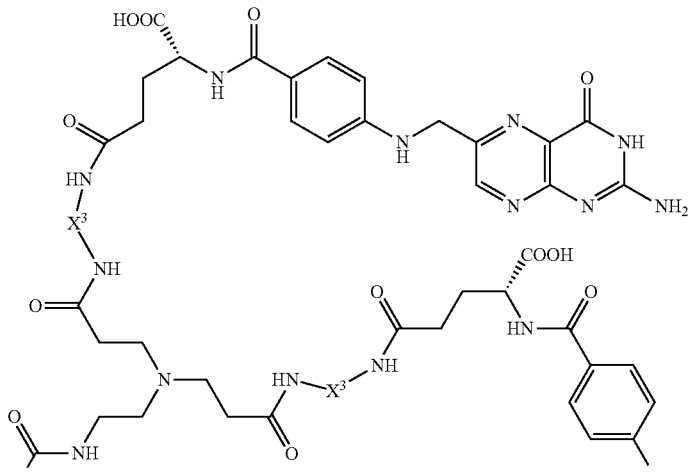

Formula (XXXIX)

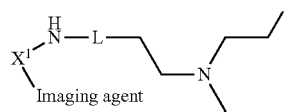
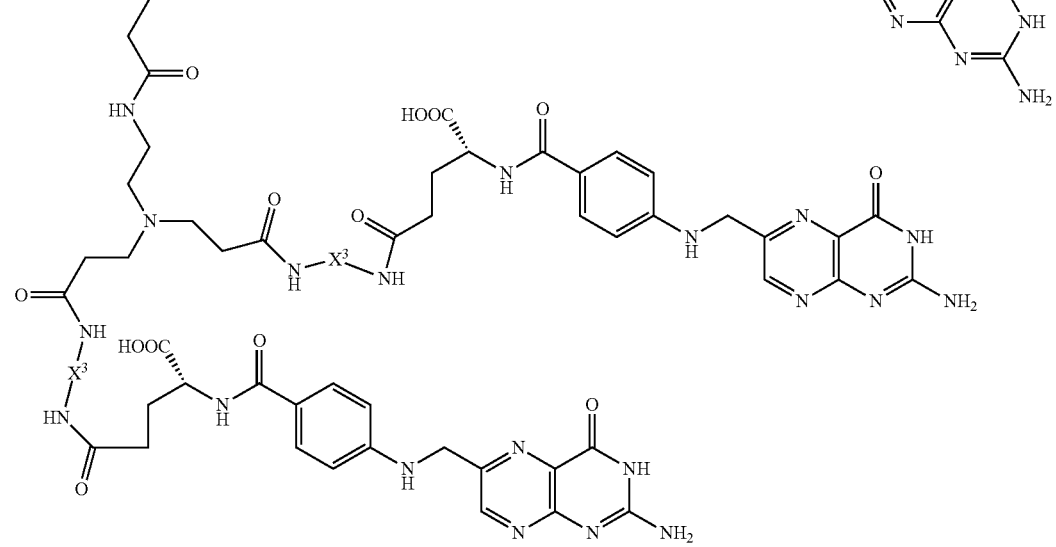
Formula (XL)
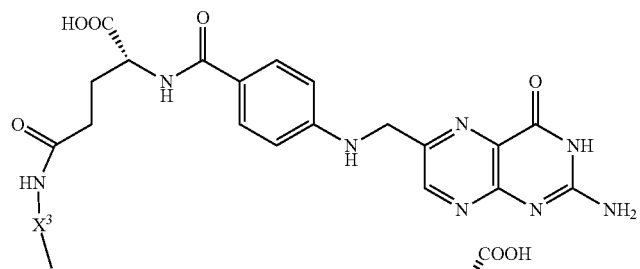
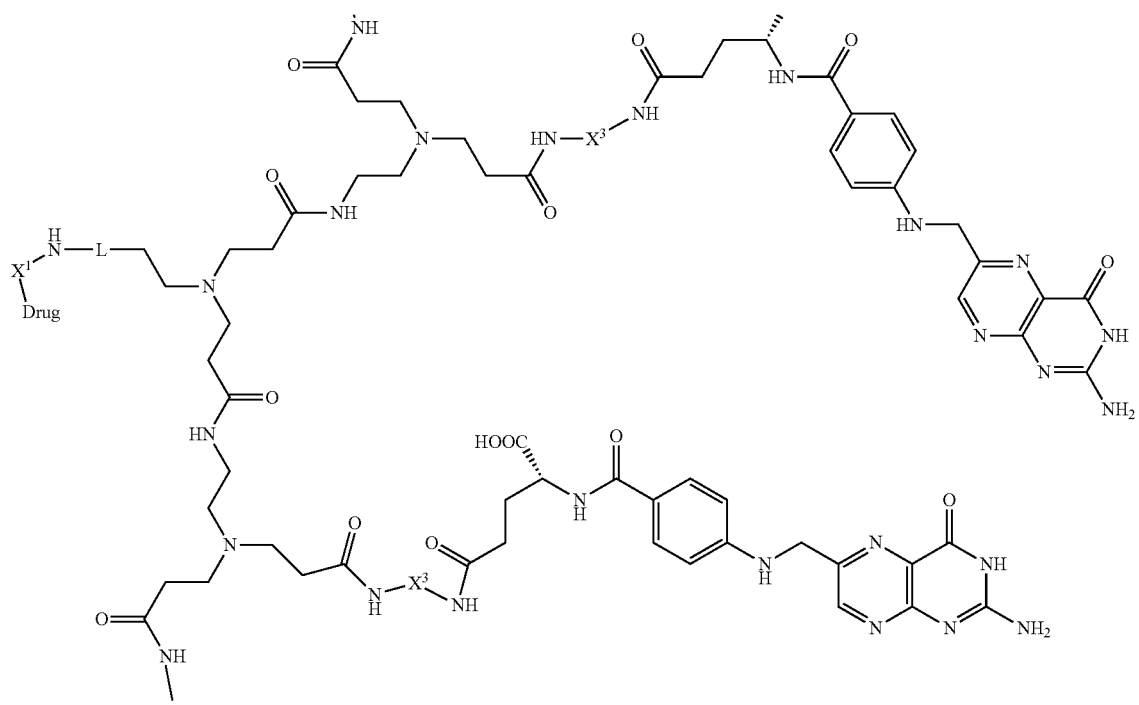

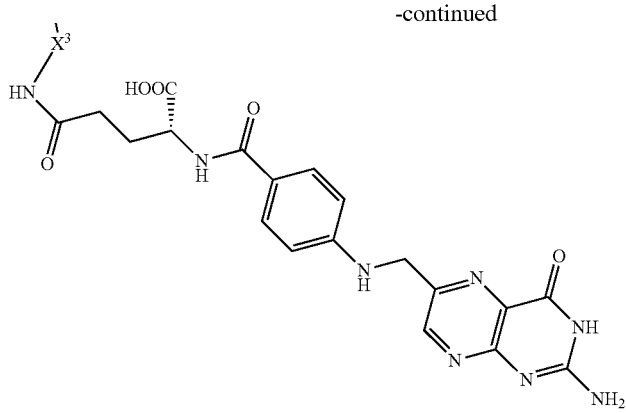
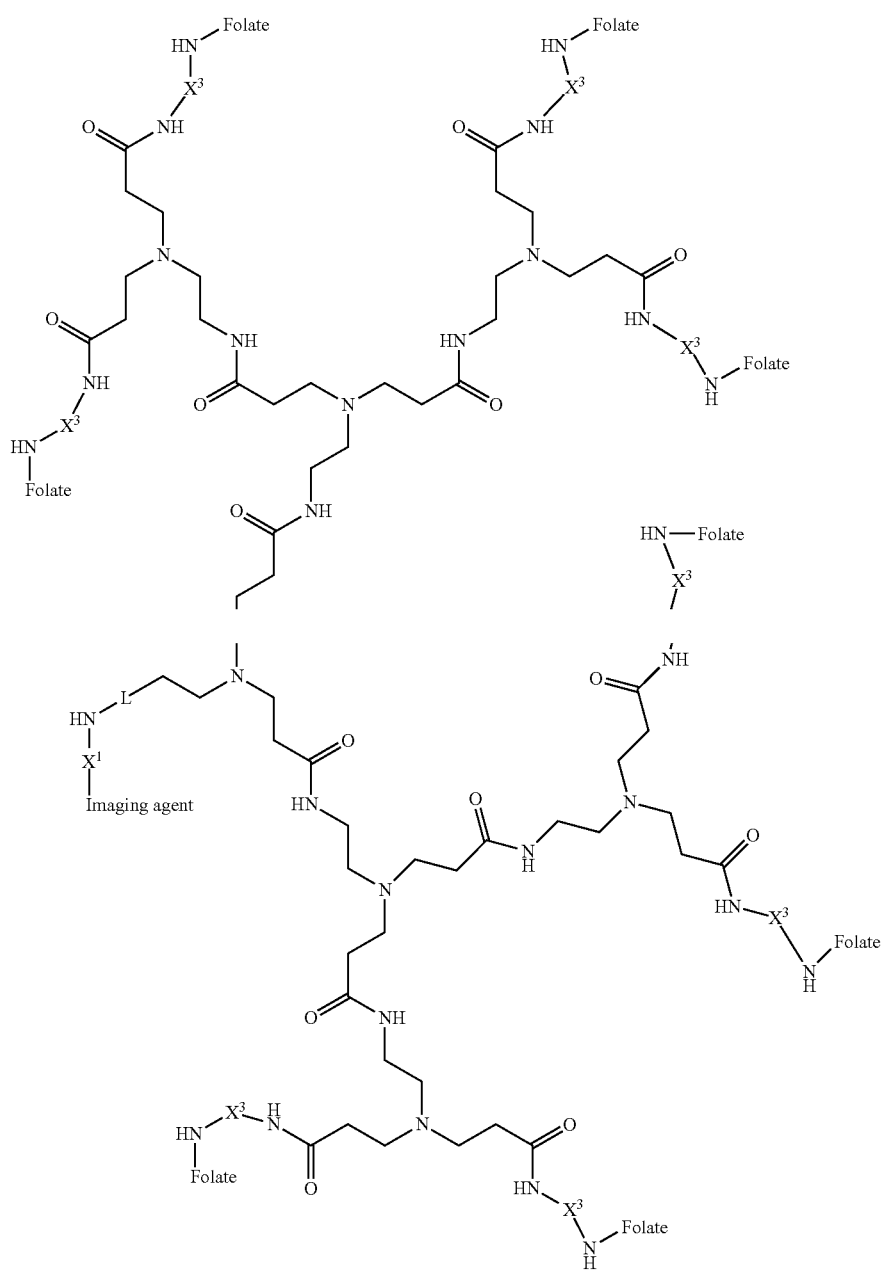
Formula (XLI)

-continued
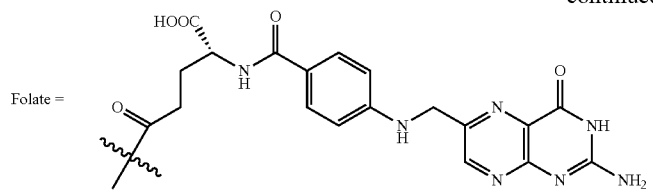
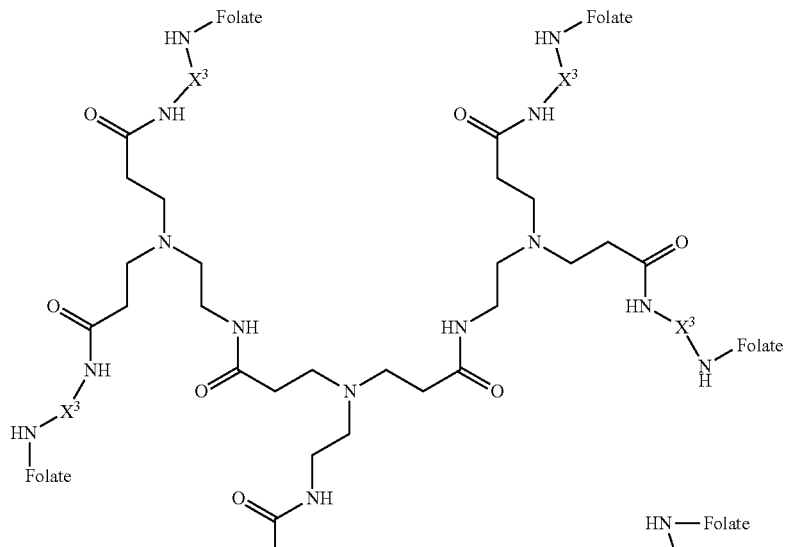
Formula (XLII)
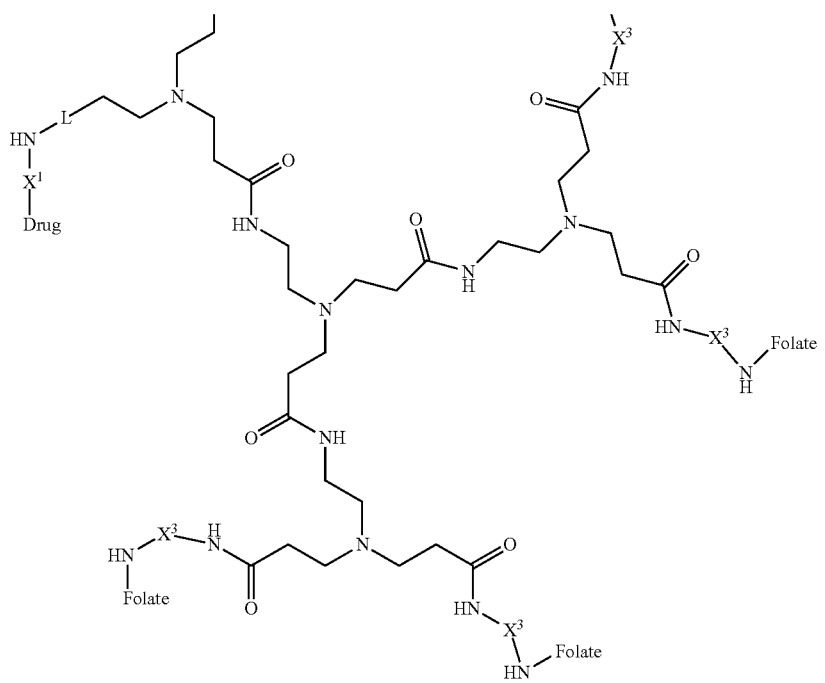
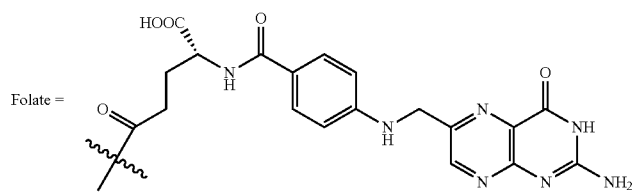

Formula (XLIII)
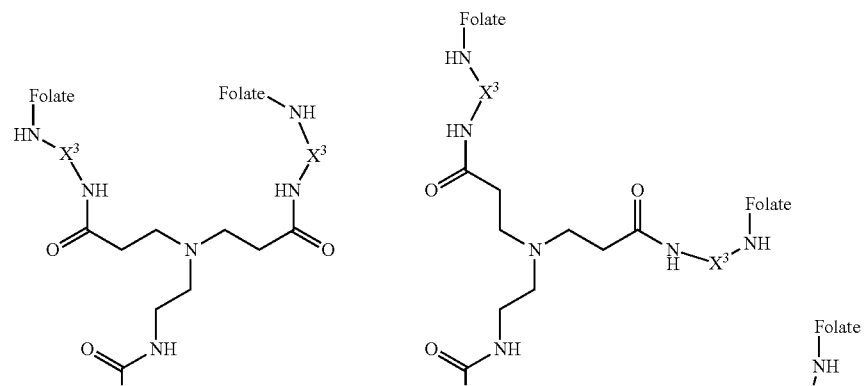
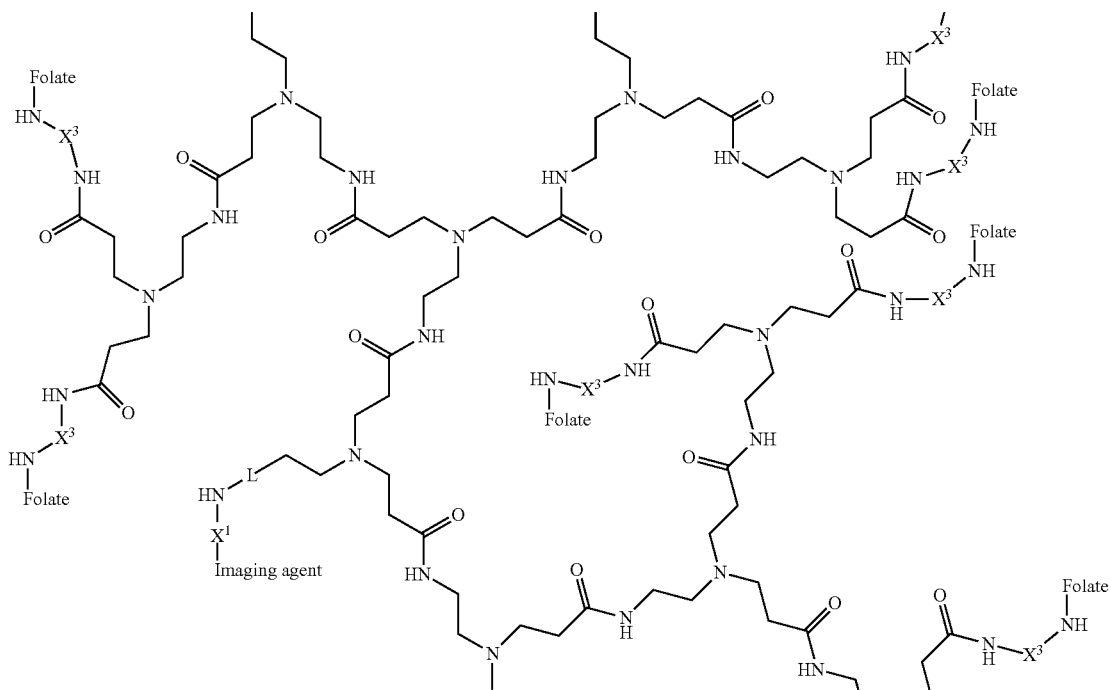
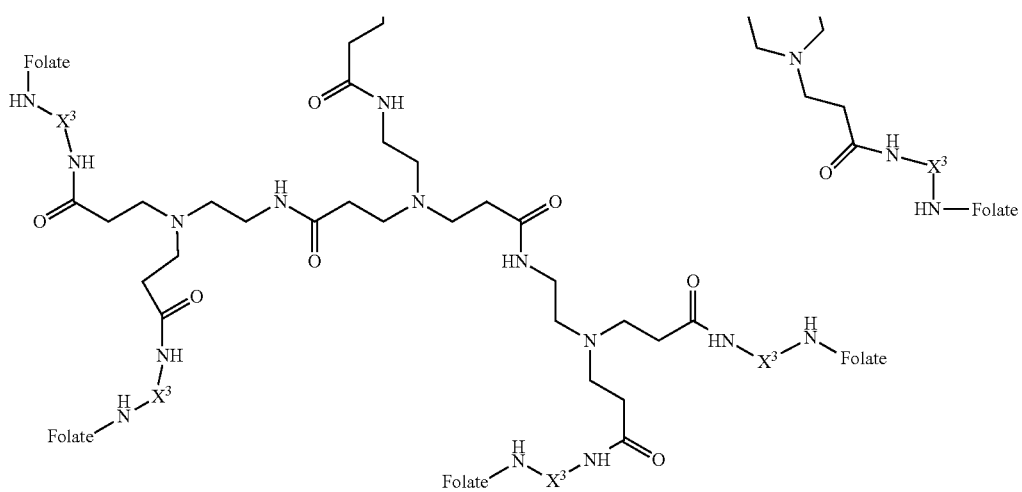

-continued

Formula (XLIV)

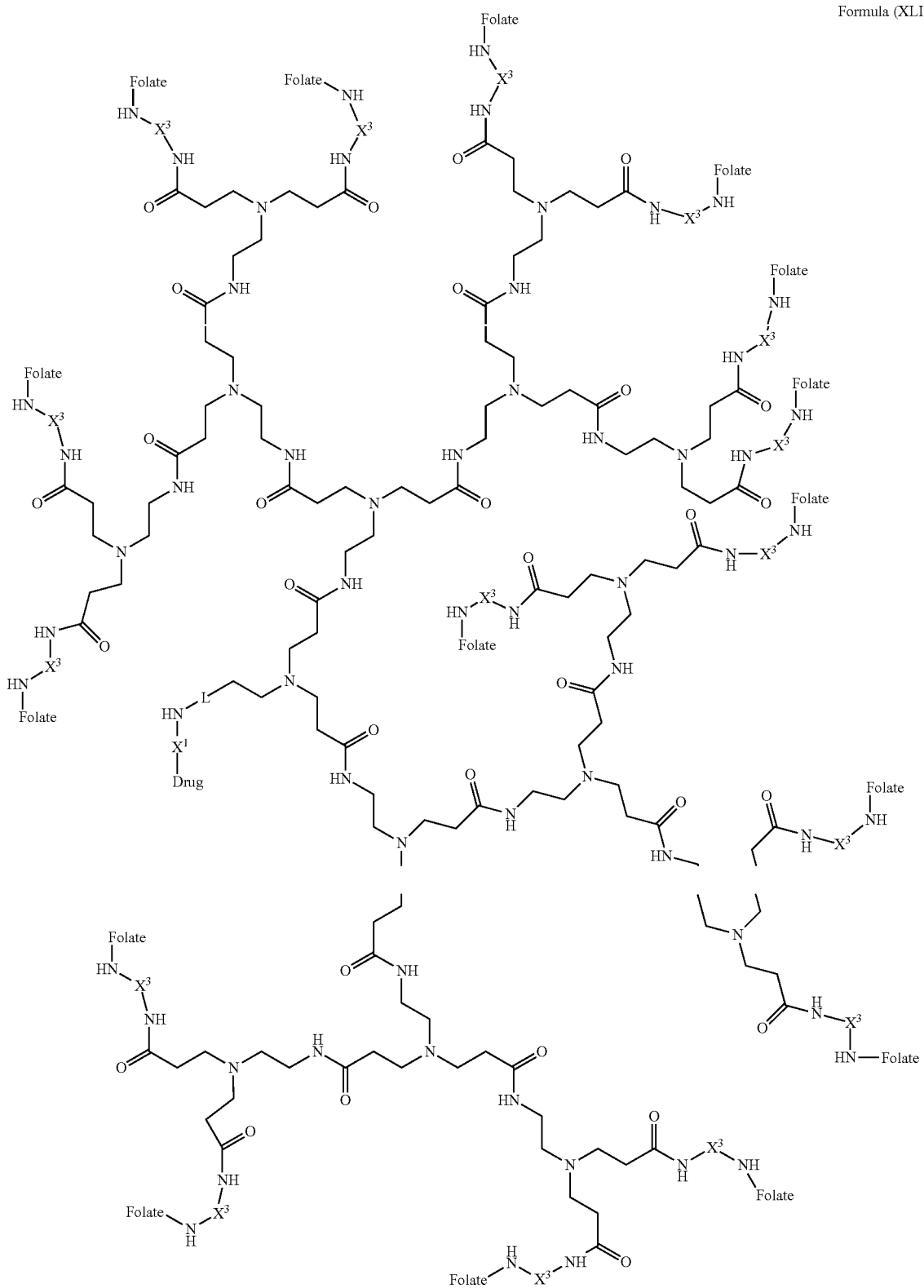

In the compounds of Formulae (XXXVII)-(XLII), L can be absent or selected from the group consisting of —CH$_2$—, —CH$_2$CH$_2$—, —CH$_2$CH$_2$CH$_2$—, —CH$_2$CH$_2$CH$_2$CH$_2$—, —OCH$_2$CH$_2$OCH$_2$CH$_2$—, and —CH$_2$OCH$_2$CH$_2$OCH$_2$CH$_2$OCH$_2$CH$_2$CH$_2$—; X$^1$ is absent or a linker, (e.g., C$_{1-4}$ alkylene and C$_{1-8}$ alkyleneoxide); and X$^3$ is a linker selected from the group consisting of —CH$_2$CH$_2$—OCH$_2$CH$_2$OCH$_2$CH$_2$, —CH₂OCH₂CH₂OCH₂CH₂OCH₂CH₂CH₂—,
CH₂CH₂NHC(=O)CH₂CH₂CH₂C(=O)NHCH₂CH₂—
CH₂OCH₂CH₂OCH₂CH₂OCH₂CH₂CH₂—, and
—CH₂CH₂NHC(=O)CH₂CH₂C(=O)NHCH₂CH₂—
CH₂OCH₂CH₂OCH₂CH₂OCH₂CH₂CH₂—. The drug can be an anticancer drug selected from the group consisting of doxorubicin, platinum, SN-38, paclitaxel, docetaxel, combretastin A-4, vinblastine, vincristine, vinorelbine, camptothecin, etoposide, teniposide, auristatin, calicheamicin, maytansinoid, and duocarmycin.

Various methods can be used to make the asymmetrical dendritic compounds described herein. Some embodiments described herein relate to a method of making N-Boc-dendrimer-targeting ligands, e.g., asymmetrical dendritic compounds of Formula (I) in which R¹—X¹—NH-L comprises N-Boc and in which NH—X²—R² comprises a targeting agent. For example, the following reaction scheme illustrates the coupling of an N-Boc-dendrimer-NH₂ and targeting agents to form N-Boc-dendrimer-targeting ligands:

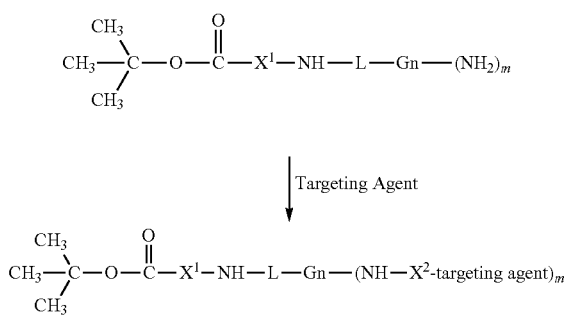

Targeting Agent

For example, an embodiment provides a method that comprises conducting a coupling reaction between N-Boc-dendrimer-NH₂ and targeting ligands in the presence of a coupling reagent at a temperature in the range of ambient temperature to about 100° C., e.g., in the range of 20° C. to 100° C., or at 30° C., 40° C., 50° C., 60° C., 70° C., 80° C., 90° C., or 100° C., to form the N-Boc-dendrimer-targeting ligands. Those skilled in the art will recognize that the N-Boc-dendrimer-NH₂ and N-Boc-dendrimer-targeting ligands illustrated in the above reaction scheme are examples of compounds of Formula (I), and thus that X¹, X², L, n, m and targeting agent can be selected as described elsewhere herein.

For example, some embodiments described herein relate to a method of making N-Boc-dendrimer-folate, e.g., asymmetrical dendritic compounds of Formula (I) in which R¹—X¹—NH-L comprises N-Boc and in which NH—X²—R² comprises a folate targeting agent. For example, the following reaction scheme illustrates the coupling of an N-Boc-dendrimer-NH₂ and folic acid to form N-Boc-dendrimer-folate:

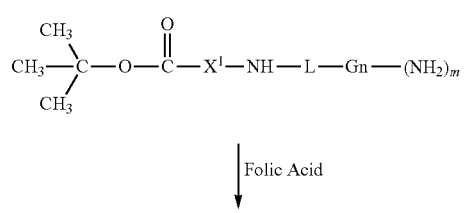

Folic Acid

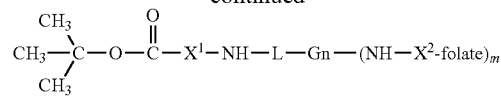

For example, an embodiment provides a method that comprises conducting a coupling reaction between N-Boc-dendrimer-NH₂ and folic acid in the presence of a coupling reagent at a temperature in the range of ambient temperature to about 100° C., e.g., in the range of 20° C. to 100° C., or at 30° C., 40° C., 50° C., 60° C., 70° C., 80° C., 90° C., or 100° C., to form the N-Boc-dendrimer-folate. Those skilled in the art will recognize that the N-Boc-dendrimer-NH₂ and N-Boc-dendrimer-folate illustrated in the above reaction scheme are examples of compounds of Formula (I), and thus that X¹, X², L, n, m and folate targeting agent can be selected as described elsewhere herein.

In some embodiments, the reactants can be intermixed with one or more solvents, such as an organic solvent. Examples of organic aprotic solvents include, but are not limited to, dimethylformamide (DMF) and dimethyl sulfoxide (DMSO). The reactants and/or solvents may be commercially available and/or may be synthesized according to methods known to those of ordinary skill in the art as guided by the teachings provided herein.

In some embodiments, the reactants can be intermixed in the presence of a suitable base. Suitable bases are known to those skilled in the art. Examples of bases include, but are not limited to, an amine base, such as an alkylamine (including mono-, di- and tri-alkylamines (e.g., triethylamine)). In some embodiments, the reactants can be intermixed in the presence of a coupling agent. Any suitable coupling agent may be used. In some embodiments, the coupling agent can be selected from 1-ethyl-3-(3-dimethylaminopropyl)-carbodiimide (EDC), 1,3-dicyclohexyl carbodiimide (DCC), 1,1'-carbonyl-diimidazole (CDI), N,N'-disuccinimidyl carbonate (DSC), N-[(dimethylamino)-1H-1,2,3-triazolo-[4,5-b]pyridine-1-yl-methylene]-N-methylmethanaminium hexafluorophosphate N-oxide (HATU), 2-[(1H-benzotriazol-1-yl)-1,1,3,3-tetramethylaminium hexafluorophosphate (HBTU), 2-[(6-chloro-1H-benzotriazol-1-yl)-1,1,3,3-tetramethylaminium hexafluorophosphate (HCTU), benzotriazole-1-yl-oxy-tris-pyrrolidino-phosphonium hexafluorophosphate (PyBOP), bromo-tris-pyrrolidino-phosphonium hexafluorophosphate (PyBroP), 2-[(1H-benzotriazol-1-yl)-1,1,3,3-tetramethylaminium tetrafluoroborate (TBTU), and benzotriazol-1-yl-oxy-tris-(dimethylamino)phosphonium hexafluorophosphate (BOP).

Some embodiments described herein relate to a method of making amino-dendrimer-targeting ligands, e.g., asymmetrical dendritic compounds of Formula (I) in which R¹—X¹—NH-L comprises NH₂ and in which NH—X²—R² comprises a targeting agent. For example, the following reaction scheme illustrates the deprotection of N-Boc-dendrimer-targeting ligands by treatment with acid to form amino-dendrimer-targeting ligands:

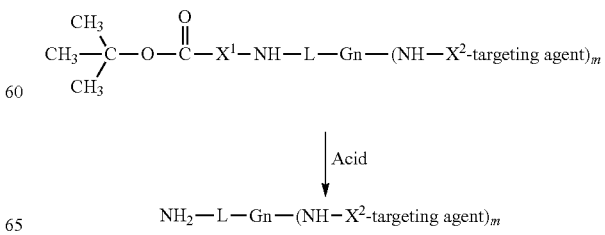

Acid

For example, an embodiment provides a method that comprises treating N-Boc-dendrimer-targeting ligands with an acid (e.g., trifluoroacetic acid (TFA)) at a temperature in the range of ambient temperature to about 100° C., e.g., in the range of 20° C. to 100° C., or at 30° C., 40° C., 50° C., 60° C., 70° C., 80° C., 90° C., or 100° C., to form the amino-dendrimer-targeting ligands. Those skilled in the art will recognize that the N-Boc-dendrimer-targeting ligands and amino-dendrimer-targeting ligands illustrated in the above reaction scheme are examples of compounds of Formula (I), and thus that $X^1$, $X^2$, L, n, m and targeting agent can be selected as described elsewhere herein.

For example, some embodiments described herein relate to a method of making amino-dendrimer-folate, e.g., asymmetrical dendritic compounds of Formula (I) in which $R^1$—$X^1$—NH-L comprises $NH_2$ and in which NH—$X^2$—$R^2$ comprises a folate targeting agent. For example, the following reaction scheme illustrates the deprotection of N-Boc-dendrimer-folate by treatment with acid to form amino-dendrimer-folate:

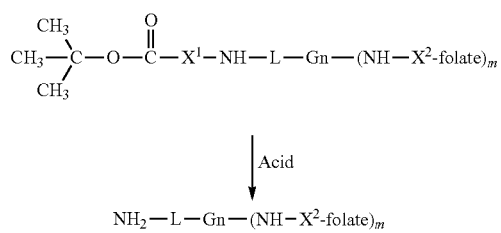

For example, an embodiment provides a method that comprises treating N-Boc-dendrimer-folate with an acid (e.g., trifluoroacetic acid (TFA)) at a temperature in the range of ambient temperature to about 100° C., e.g., in the range of 20° C. to 100° C., or at 30° C., 40° C., 50° C., 60° C., 70° C., 80° C., 90° C., or 100° C., to form the amino-dendrimer-folate. Those skilled in the art will recognize that the N-Boc-dendrimer-folate and amino-dendrimer-folate illustrated in the above reaction scheme are examples of compounds of Formula (I), and thus that $X^1$, $X^2$, L, n, m and folate can be selected as described elsewhere herein. For example, the dendrimers can have the structures shown in Formulae (XXI)-(XXVIII) above.

Some embodiments described herein relate to a method of making imaging agent-dendrimer-targeting ligands, e.g., asymmetrical dendritic compounds of Formula (I) in which $R^1$—$X^1$—NH-L comprises an imaging agent and in which NH—$X^2$—$R^2$ comprises a targeting agent. For example, the following reaction scheme illustrates the coupling of an amino-dendrimer-targeting ligand and an imaging agent to form imaging agent-dendrimer-targeting ligands:

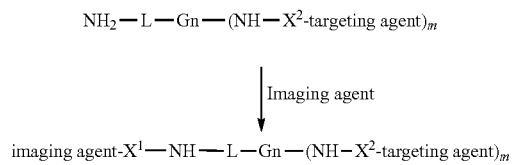

For example, an embodiment provides a method that comprises conducting a coupling reaction between amino-dendrimer-targeting ligands and imaging agent in the presence of a coupling reagent at a temperature in the range of ambient temperature to about 100° C., e.g., in the range of 20° C. to 100° C., or at 30° C., 40° C., 50° C., 60° C., 70° C., 80° C., 90° C., or 100° C., to form the imaging agent-dendrimer-targeting ligands. Those skilled in the art will recognize that the amino-dendrimer-targeting ligands and imaging agent-dendrimer-targeting ligands illustrated in the above reaction scheme are examples of compounds of Formula (I), and thus that $X^1$, $X^2$, L, n, m, targeting agent and imaging agent can be selected as described elsewhere herein.

For example, some embodiments described herein relate to a method of making imaging agent-dendrimer-folates, e.g., asymmetrical dendritic compounds of Formula (I) in which $R^1$—$X^1$—NH-L comprises an imaging agent and in which NH—$X^2$—$R^2$ comprises a folate targeting agent. For example, the following reaction scheme illustrates the coupling of an amino-dendrimer-folate and an imaging agent to form imaging agent-dendrimer-folates:

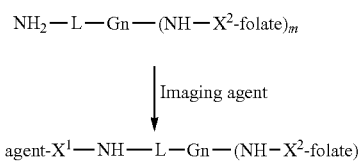

For example, an embodiment provides a method that comprises conducting a coupling reaction between amino-dendrimer-folate and imaging agent in the presence of a coupling reagent at a temperature in the range of ambient temperature to about 100° C., e.g., in the range of 20° C. to 100° C., or at 30° C., 40° C., 50° C., 60° C., 70° C., 80° C., 90° C., or 100° C., to form the imaging agent-dendrimer-folate. Those skilled in the art will recognize that the amino-dendrimer-folates and imaging agent-dendrimer-folates illustrated in the above reaction scheme are examples of compounds of Formula (I), and thus that $X^1$, $X^2$, L, n, m and folate can be selected as described elsewhere herein. For example, the dendrimers can have the structures shown in Formulae (XXII), (XXIV), (XXVI), (XXVIII), (XXIX), (XXXI), (XXXIII), and (XXXV) above.

Some embodiments described herein relate to a method of making drug-dendrimer-targeting ligands, e.g., asymmetrical dendritic compounds of Formula (I) in which $R^1$—$X^1$—NH-L comprises a drug and in which NH—$X^2$—$R^2$ comprises a targeting agent. For example, the following reaction scheme illustrates the coupling of an amino-dendrimer-targeting ligand and a drug to form drug-dendrimer-targeting ligands:

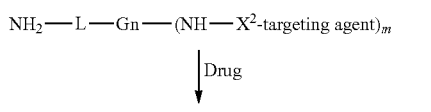

For example, an embodiment provides a method that comprises conducting a coupling reaction between amino-dendrimer-targeting ligands and drug in the presence of a coupling reagent at a temperature in the range of ambient temperature to about 100° C., e.g., in the range of 20° C. to 100° C., or at 30° C., 40° C., 50° C., 60° C., 70° C., 80° C., 90° C., or 100° C., to form the imaging agent-dendrimertargeting ligands. Those skilled in the art will recognize that the amino-dendrimer-targeting ligands and drug-dendrimer-targeting ligands illustrated in the above reaction scheme are examples of compounds of Formula (I), and thus that $X^1$, $X^2$, L, n, m, targeting agent and drug can be selected as described elsewhere herein.

For example, some embodiments described herein relate to a method of making drug-dendrimer-folates, e.g., asymmetrical dendritic compounds of Formula (I) in which $R^1$—$X^1$—NH-L comprises a drug and in which NH—$X^2$—$R^2$ comprises a folate targeting agent. For example, the following reaction scheme illustrates the coupling of an amino-dendrimer-folate and a drug to form drug-dendrimer-folates:

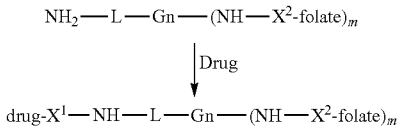

For example, an embodiment provides a method that comprises conducting a coupling reaction between amino-dendrimer-folate and drug in the presence of a coupling reagent at a temperature in the range of ambient temperature to about 100° C., e.g., in the range of 20° C. to 100° C., or at 30° C., 40° C., 50° C., 60° C., 70° C., 80° C., 90° C., or 100° C., to form the drug-dendrimer-folate. Those skilled in the art will recognize that the amino-dendrimer-folates and drug-dendrimer-folates illustrated in the above reaction scheme are examples of compounds of Formula (I), and thus that $X^1$, $X^2$, L, n, m, folate and drug can be selected as described elsewhere herein. For example, the dendrimers can have the structures shown in Formulae (XXII), (XXIV), (XXVI), (XXVIII), (XXX), (XXXII), (XXXIV), and (XXXVI) above.

The preparation of the various asymmetrical dendritic compounds described herein can be conducted using routine synthetic techniques generally known to those skilled in the art as informed by the guidance provided herein, including the coupling and deprotection reaction schemes discussed above. For example, in some embodiments, the reactions may be carried out at room temperature. In some embodiments, the reaction mixtures may be stirred for several hours. The reaction products may be isolated by any means known in the art including chromatographic techniques. In some embodiments, the solvent may be evaporated to recover the reaction product (e.g., via rotary evaporation). In other embodiments, the reaction product may be removed by precipitation followed by centrifugation.

The term "pharmaceutical composition" refers to a mixture of a therapeutic agent as described herein along with one or more other pharmaceutically acceptable chemical components, such as diluents or additional pharmaceutical carriers. The pharmaceutical composition facilitates administration of the amphiphilic polyamino acid and/or the hydrophobic drug to an organism.

Multiple techniques of administering a pharmaceutical composition exist in the art and maybe be used to administer the therapeutic agents described herein. Suitable routes of administration may include, for example, parenteral delivery, including intramuscular, subcutaneous, intravenous, intramedullary injections, as well as intrathecal, direct intraventricular, intraperitoneal, intranasal, or intraocular injections. therapeutic agent can also be administered in sustained or controlled release dosage forms, including depot injections, osmotic pumps, and the like, for prolonged and/or timed, pulsed administration at a predetermined rate. Additionally, the route of administration may be local or systemic.

The term "pharmaceutical carrier" refers to a chemical compound that facilitates the incorporation of a therapeutic agent into cells or tissues.

The term "diluent" refers to chemical compounds diluted in water to form a solution that dissolves therapeutic agent as well as stabilize the biologically active form of the therapeutic agent. Salts dissolved in buffered solutions can be utilized as diluents in a manner generally known in the art. As used herein, an "excipient" refers to an inert substance that is added to a therapeutic agent to provide, without limitation, bulk, consistency, stability, binding ability, lubrication, disintegrating ability, etc., to the composition. A "diluent" is a type of excipient.

The term "physiologically acceptable" refers to a pharmaceutical carrier or diluent that does not abrogate the biological activity and properties of the therapeutic agent.

Some embodiments herein are directed to a method of delivering a therapeutic agent to a cell, by a method that includes contacting the cell with the therapeutic agent. In some embodiments, the cells can be tumor cells, such as animal (e.g., mammalian and/or human) tumor cells. Cells lines which are model systems for tumors may be used. In some embodiments these methods can be performed in vitro, while in other embodiments they can be performed in vivo.

Other embodiments are directed to a method of treating a mammal. For example, an embodiment provides a method of treating cancer, comprising identifying a patient in need of cancer treatment and administering a therapeutically effective amount of a therapeutic agent as described herein to the patient.

Pharmaceutical compositions suitable for administration include therapeutic agents where the active ingredients (e.g., attached imaging agent and/or drug) are contained in an amount effective to achieve its intended purpose. The effective amount of active ingredient required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of therapeutic agent effective to prevent, alleviate or ameliorate symptoms of disease or prolong the survival of the subject being treated. Determination of a therapeutically effective amount is well within the capability of those skilled in the art, as informed by the guidance contained in the detailed disclosure provided herein.

The therapeutic agents described herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The efficacy of a particular compound may be established using several recognized methods, such as in vitro methods, animal models, and/or human clinical trials. Recognized in vitro models exist for nearly every class of condition, including various types of cancer. When selecting a model to determine efficacy, the skilled artisan can be guided by the state of the art to choose an appropriate model, dose, and route of administration, and regime.

Some embodiments herein are directed to a method of delivering a therapeutic agent as described herein containing an imaging agent and a targeting agent, to a cell. In an embodiment, the imaging agent is a cancer-specific imaging agent. The targeting ligand can be selected based on the type of cell to be targeted. In various embodiment, the targeting agents is selected from the group consisting of folic acid, mannose, anisamide, RGD peptide, NGR peptide, galactosamine, antibody, antibody fragments, and protein. Many imaging studies such as MRI, PET, CT and x-ray, involve the use of imaging agents to obtain better resolution of tissues, particularly cancer tissues. Cancer-specific imaging agents are designed to provide more information about internal organs, cellular processes and tumors, as well as normal tissue. They can be used to diagnose disease as well as monitor treatment effects.

Therapeutic agents containing cancer-specific imaging agents may be administered by mouth, enema, or injection into a vein, artery, or body cavity. The agents are typically absorbed by the body or passed out of the body in the urine or bowel movement.

Gadolinium is a contrast agent that may be given during MRI scans; it highlights areas of tumor or inflammation. Sometimes the gadolinium is given midway through the MRI scan by injection into a vein.

Nuclear imaging (e.g., PET and Nuclear Medicine Imaging Agents or scintigraphy) involves the use of imaging agents that contain radioactive contrast agents (called radiopharmaceuticals) to obtain images. Some agents used for PET imaging provide information about tissue metabolism or some other specific molecular activity. The following are radioactive contrast agents that can be included in the therapeutic agents described herein:

$^{64}$Cu diacetyl-bis(N$^4$-methylthiosemicarbazone), also called ATSM or Copper 64, is an imaging agent used in PET or PET/CT for its ability to identify hypoxic tissue (tissue with low oxygen).

$^{18}$F-fluorodeoxyglucose (FDG) is a radioactive sugar molecule, that, when used with PET imaging, produces images that show the metabolic activity of tissues. In FDG-PET scanning, the high consumption of the sugar by tumor cells, as compared to the lower consumption by normal surrounding tissues, identifies these cells as cancer cells. FDG is also used to study tumor response to treatment.

$^{18}$F-fluoride is an imaging agent for PET imaging of new bone formation. It can assess changes both in normal bone as well as bone tumors. As a result, it can be used to measure response to treatment.

3'-deoxy-3'-($^{18}$F)fluorothymidine (FLT) is a radiolabeled imaging agent that is being investigated in PET imaging for its ability to detect growth in a primary tumor. Studies may also measure the ability of FLT with PET to detect tumor response to treatment.

$^{18}$F-fluoromisonidazole (FMISO) is an imaging agent used with PET imaging that can identify hypoxia (low oxygen) in tissues. Tumors with low oxygen have been shown to be resistant to radiation and chemotherapy.

Gallium attaches to areas of inflammation, such as infection. It also attaches to areas of rapid cell division, such as cancer cells. It can take gallium a few days to accumulate in the affected tissue, so the scan may be done 2-3 days after the gallium is administered.

Technetium-99m is used to radiolabel many different common radiopharmaceuticals. It is used most often in bone and heart scans.

Thallium is a radioactive tracer typically used to examine heart blood flow. The thallium scan is often combined with an exercise test to determine how well the heart functions under stress. A thallium scan may also be used to measure tumor response.

X-ray imaging agents (contrast agents) work with x-ray and CT imaging by increasing the density of tissues (and thus blocking x-ray transmission). They can be administered by mouth, enema, or injection.

Barium is the most common oral contrast agent used in CT. It enhances images of the abdomen and pelvis, by filling of the stomach and intestines. Barium contrast looks like, and has a similar consistency to a milk shake. It may be offered in different flavors.

Gastrografin contrast agent contains iodine and is a water-based drink with a tinted yellow color. When given orally, gastrografin may taste bitter. It is used in the same general way as barium.

Several different agents containing iodine are used as imaging agents for x-ray and CT. Once injected into the blood stream these agents highlight blood vessels as well as the tissues of various organs. Iodine contrast agents are often classified as being ionic and nonionic. They both work similarly, but nonionic agents have less frequent side effects than ionic agents.

All the contrast imaging agents described above can be conjugated onto asymmetrical dendritic compounds described herein to provide better imaging resolution of cancer tissues.

EXAMPLES

Additional embodiments are disclosed in further detail in the following examples, which are not in any way intended to limit the scope of the claims. Methyl acrylate, ethylene diamine, folic acid, and other reagents were purchased from Sigma-Aldrich and TCI America. N-Boc-ethylenediamine, N-Boc-propanediamine, N-Boc-hexanediamine, N-Boc-PEG$_2$-amine, and N-Boc-PEG$_3$-amine, and maleimide were purchased from AnamChem, LLC (San Diego, Calif.).

The examples described herein are provided for the purposes of further describing the embodiments, and do not limit the scope of the invention.

Example 1

Synthesis of N-Boc-ED-dendron methyl ester 2

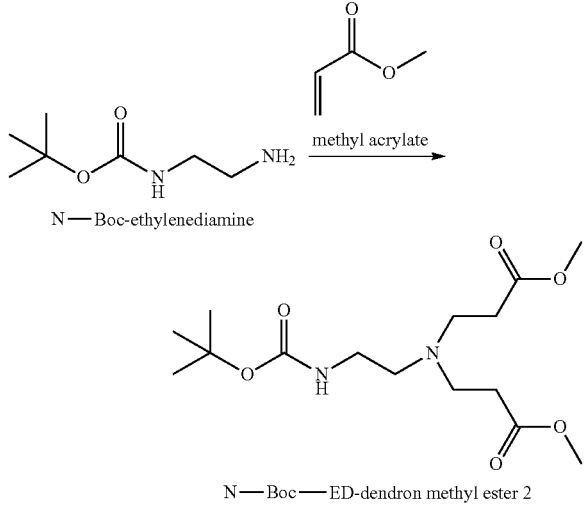

N-Boc-ethylenediamine (155 g) was added to a flask and purged with argon. Methyl acrylate (195 g) was added and the resulting mixture was stirred for 15 hours at ambient temperature. The reaction was then heated at 70° C., for 1 hour. Excess methyl acrylate was removed by high vacuum rotary evaporation at 70° C. The resulting N-Boc-ED-dendron methyl ester 2 product was obtained (310 g) and the structure confirmed by $^1$H-NMR analysis.

Example 2

Synthesis of N-Boc-dendrimer G0

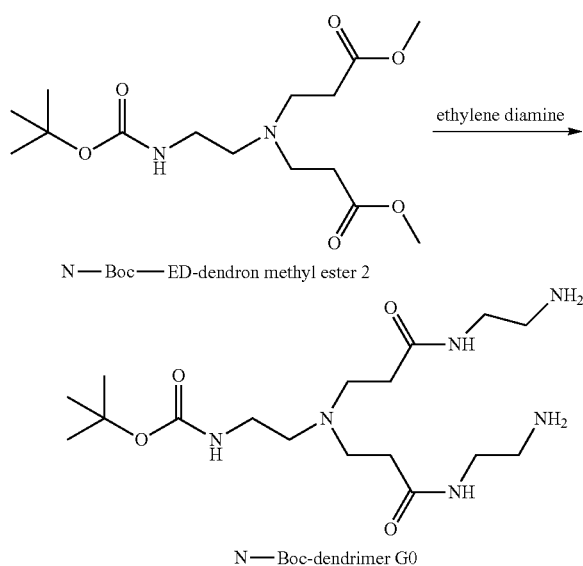

N-Boc-ED-dendron methyl ester 2 (100 g) was added to a flask and purged with argon. Ethylene diamine (500 g) was added and stirred for 2 days at ambient temperature. Then, the reaction was heated at 70° C., for 2 hours. Excess ethylene diamine was removed by high vacuum rotary evaporation at 85° C. The resulting product N-Boc-dendrimer G0 was obtained (116 g) and the structure confirmed by $^1$H-NMR analysis.

Example 3

Synthesis of N-Boc-dendrimer G1

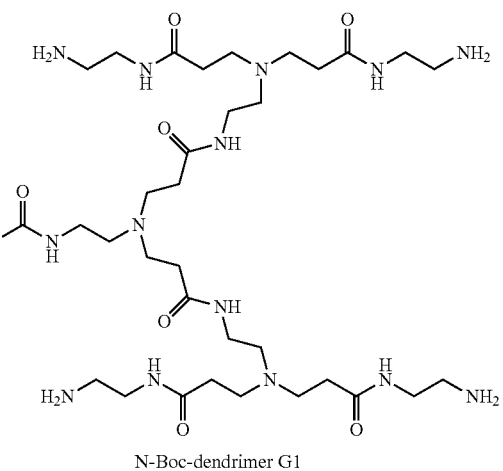

N-Boc-dendrimer G0 (50 g) was added to a flask and purged with argon. Methyl acrylate (150 g) was added, and the reaction was stirred for 15 hours at ambient temperature. Then, the reaction was heated at 70° C., for 1 hour. Excess methyl acrylate was removed by high vacuum rotary evaporation at 70° C. Ethylene diamine (250 g) was added and stirred for 2 days at ambient temperature. Then, the reaction was heated at 70° C., for 2 hours. Excess ethylene diamine was removed by high vacuum rotary evaporation at 85° C. The resulting product N-Boc-dendrimer G1 was obtained (108 g) and the structure confirmed by $^1$H-NMR analysis.

Example 4

Synthesis of N-Boc-dendrimer G2

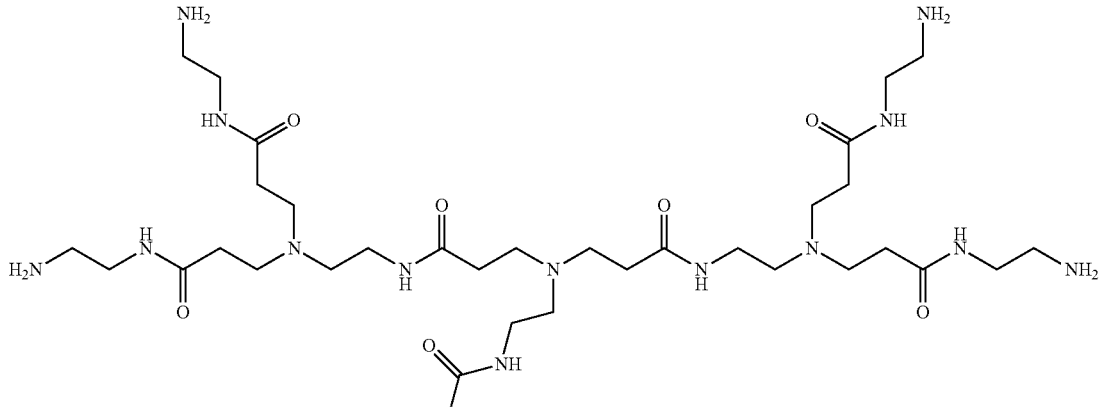

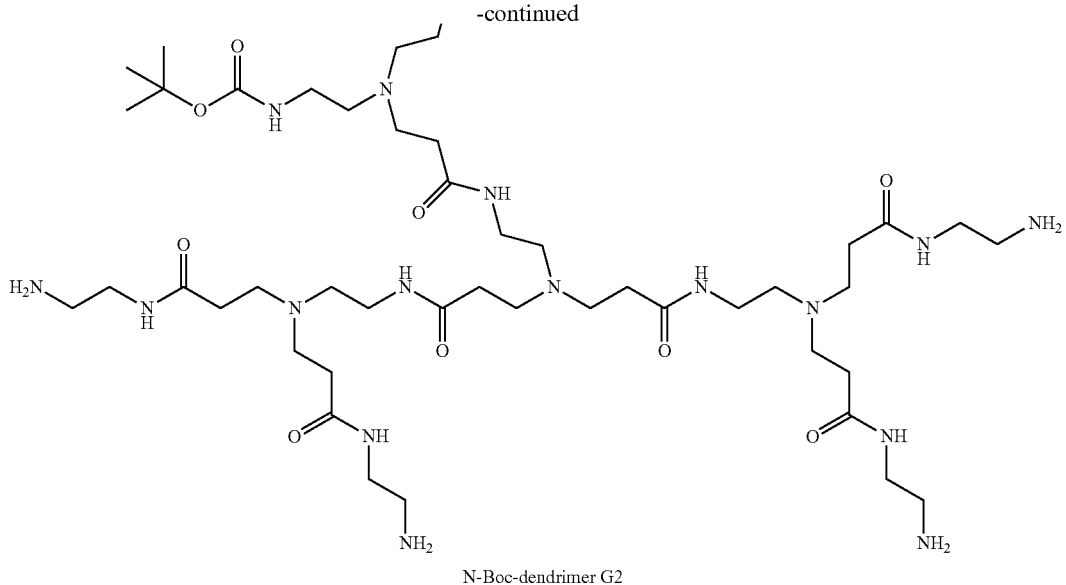

N-Boc-dendrimer G2

N-Boc-dendrimer G1 (50 g) was added to a flask and purged with argon. Methyl acrylate (150 g) was added, and the reaction was stirred for 15 hours at ambient temperature. The reaction was heated at 70° C., for 1 hour. Excess methyl acrylate was removed by high vacuum rotary evaporation at 70° C. Ethylene diamine (250 g) was added and stirred for 2 days at ambient temperature. Excess ethylene diamine was removed by high vacuum rotary evaporation at 85° C. The resulting product N-Boc-dendrimer G2 was obtained (104 g) and the structure confirmed by $^1$H-NMR analysis.

Example 5

Synthesis of N-Boc-dendrimer G3

N-Boc-dendrimer G2 (50 g) was added in a flask and purged with argon. Methyl acrylate (150 g) was added, and the reaction was stirred for 15 hours at ambient temperature. The reaction was heated at 70° C., for 1 hour. Excess methyl acrylate was removed by high vacuum rotary evaporation at 70° C. Ethylene diamine (250 g) was added and stirred for 2 days at ambient temperature. Excess ethylene diamine was removed by high vacuum rotary evaporation at 85° C. The resulting product N-Boc-dendrimer G3 was obtained (102 g) and the structure confirmed by $^1$H-NMR analysis.

Example 6

Synthesis of N-Boc-PEG$_3$-dendrimer G0

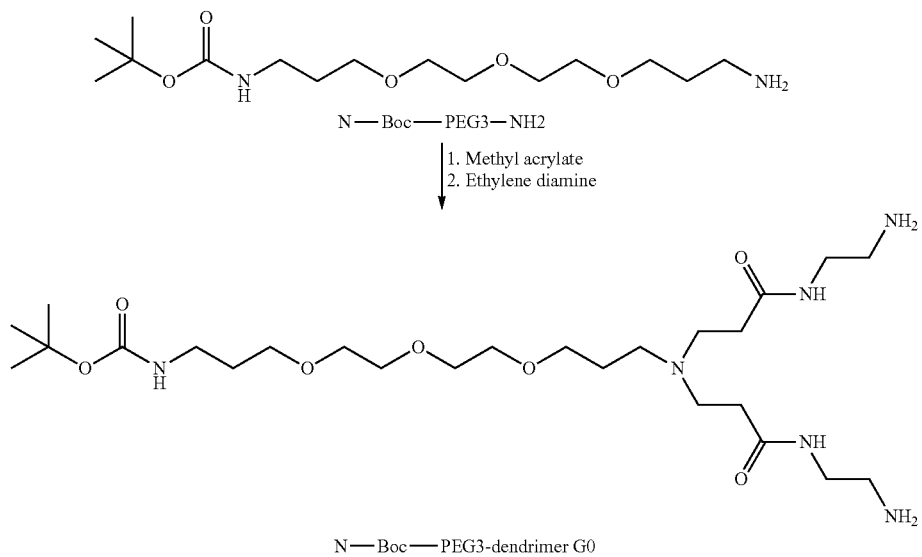

N—Boc—PEG3-dendrimer G0

N-Boc-PEG3-NH$_2$ (50 g) was added to a flask and purged with argon. Methyl acrylate (150 g) was added, and the reaction was stirred for 15 hours at ambient temperature. Then, the reaction was heated at 70° C., for 1 hour. Excess methyl acrylate was removed by high vacuum rotary evaporation at 70° C. Ethylene diamine (250 g) was added and stirred for 2 days at ambient temperature. Then, the reaction was heated at 70° C., for 2 hours. Excess ethylene diamine was removed by high vacuum rotary evaporation at 85° C. The resulting product N-Boc-PEG3-dendrimer G0 was obtained (85 g) and the structure confirmed by $^1$H-NMR analysis.

Example 7

Synthesis of N-Boc-PEG3-dendrimer G1

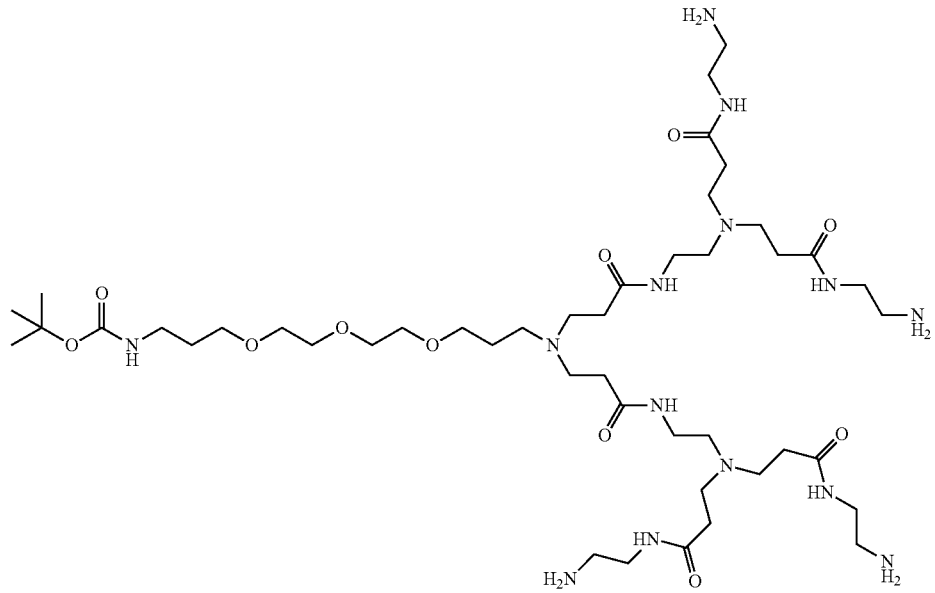

N-Boc-PEG3-dendrimer G1

N-Boc-PEG$_3$-dendrimer G0 (50 g) was added to a flask and purged with argon. Methyl acrylate (150 g) was added, and the reaction was stirred for 15 hours at ambient temperature. Then, the reaction was heated at 70° C., for 1 hour. Excess methyl acrylate was removed by high vacuum rotary evaporation at 70° C. Ethylene diamine (250 g) was added and stirred for 2 days hours at ambient temperature. Then, the reaction was heated at 70° C., for 2 hours. Excess ethylene diamine was removed by high vacuum rotary evaporation at 85° C. The resulting product N-Boc-PEG$_3$-dendrimer G1 was obtained (91 g) and the structure confirmed by $^1$H-NMR analysis.

Example 8

Synthesis of N-Boc-PEG$_3$-dendrimer G2

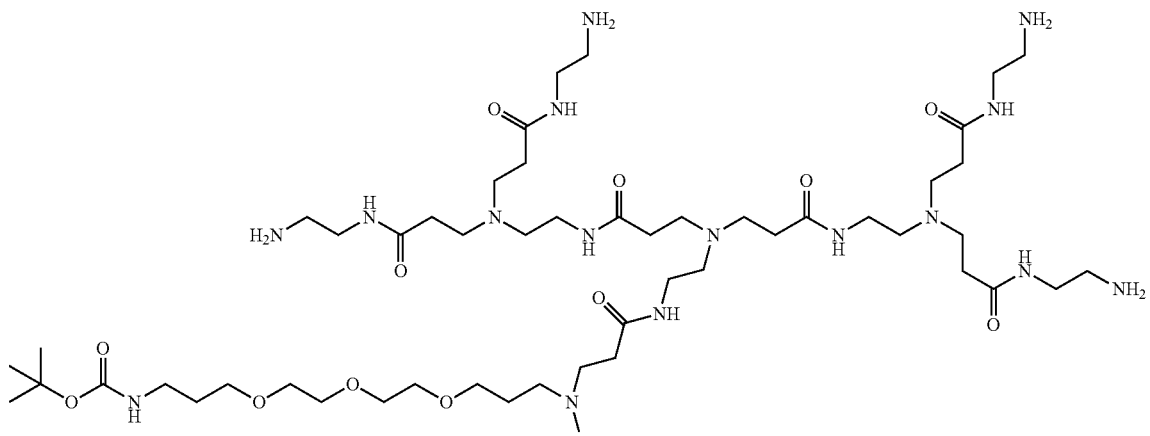

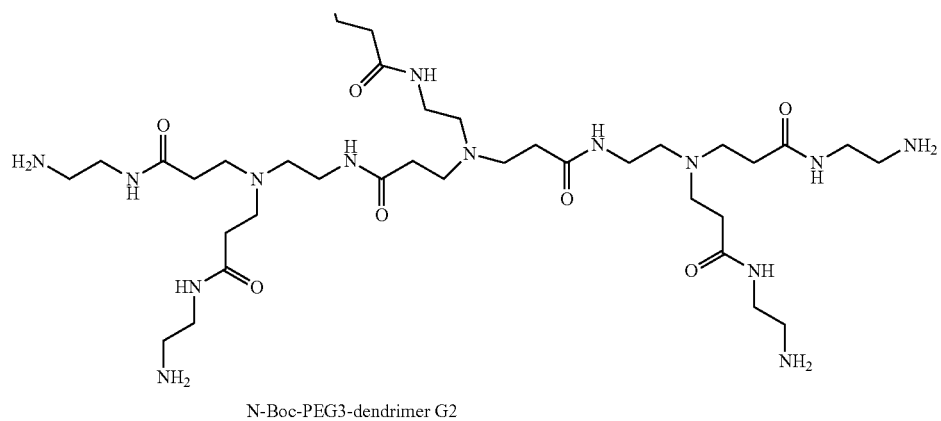
N-Boc-PEG3-dendrimer G2

N-Boc-PEG$_3$-dendrimer G1 (50 g) was added to a flask and purged with argon. Methyl acrylate (150 g) was added, and the reaction was stirred for 15 hours at ambient temperature. The reaction was heated at 70° C., for 1 hour. Excess methyl acrylate was removed by high vacuum rotary evaporation at 70° C. Ethylene diamine (250 g) was added and stirred for 2 days hours at ambient temperature. Excess ethylene diamine was removed by high vacuum rotary evaporation at 85° C. The resulting product N-Boc-PEG$_3$-dendrimer G2 was obtained 95 g and the structure confirmed by $^1$H-NMR analysis.

Example 9

Synthesis of N-Boc-PEG$_3$-dendrimer G3

N-Boc-PEG$_3$-dendrimer G2 (50 g) was added to a flask and purged with argon. Methyl acrylate (150 g) was added, and the reaction was stirred for 15 hours at ambient temperature. The reaction was heated at 70° C., for 1 hour. Excess methyl acrylate was removed by high vacuum rotary evaporation at 70° C. Ethylene diamine (250 g) was added and stirred for 2 days hours at ambient temperature. Excess ethylene diamine was removed by high vacuum rotary evaporation at 85° C. The resulting product N-Boc-PEG$_3$-dendrimer G3 was obtained (97 g) and the structure confirmed by $^1$H-NMR analysis.

Example 10

Synthesis of TFA Amino-PEG$_3$-Folate

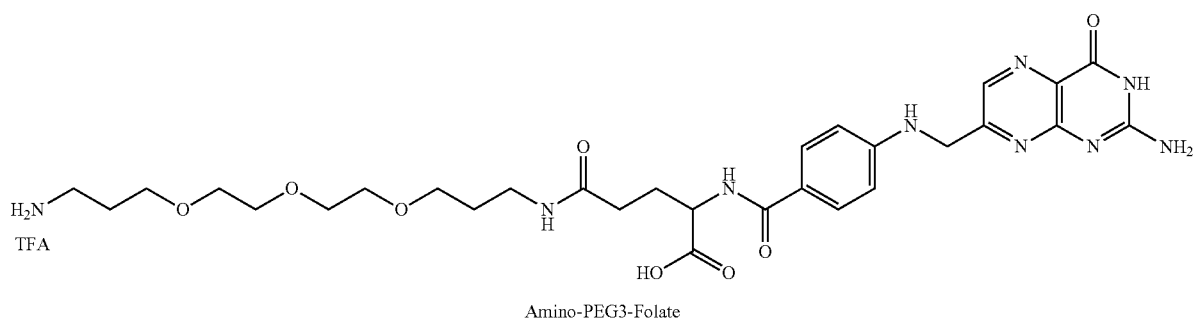 [SMILES: NCCCOCCOCCOCCCNC(=O)CCC(NC(=O)c1ccc(NCc2cnc3c(=O)[nH]c(N)nc3n2)cc1)C(=O)O]
Amino-PEG3-Folate

TFA Amino-PEG$_3$-folate was synthesized according to the procedure published in the literature (Guaragna A, Chiaviello A, Paolella C, D'Alonzo D, Palumbo G, Palumbo G. "Synthesis and evaluation of folate-based chlorambucil delivery systems for tumor-targeted chemotherapy." *Bioconjug Chem.* 2012, 23, 84-96).

Example 11

Synthesis of TFA.Amino-PEG$_3$-dendrimer-2-folates, TFA.Amino-PEG$_3$-dendrimer-4-folates, and TFA Amino-PEG$_3$-dendrimer-8-folates

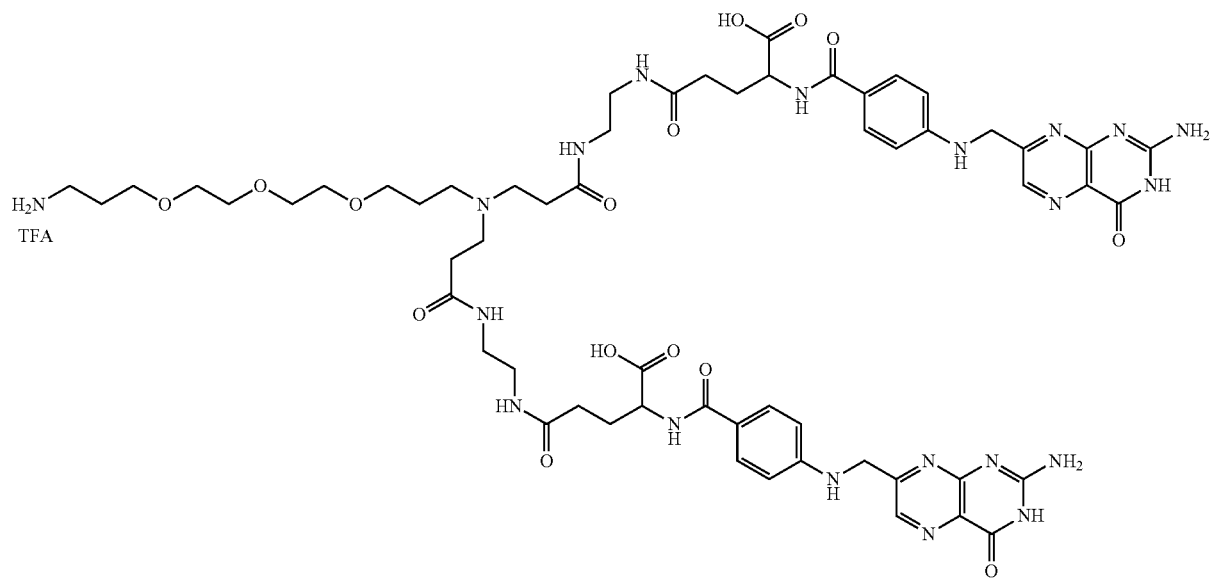

Amino-PEG3-dendrimer-2-folates

TFA Amino-EG$_3$-dendrimer-2-folates was synthesized according to a modified version of the procedure published in the literature (Guaragna A, Chiaviello A, Paolella C, D'Alonzo D, Palumbo G, Palumbo G. "Synthesis and evaluation of folate-based chlorambucil delivery systems for tumor-targeted chemotherapy." *Bioconjug Chem.* 2012, 23, 84-96) in which N-Boc-PEG$_3$-dendrimer G0 was used in place of the N-Boc-PEG$_3$-NH$_2$ used in the literature.

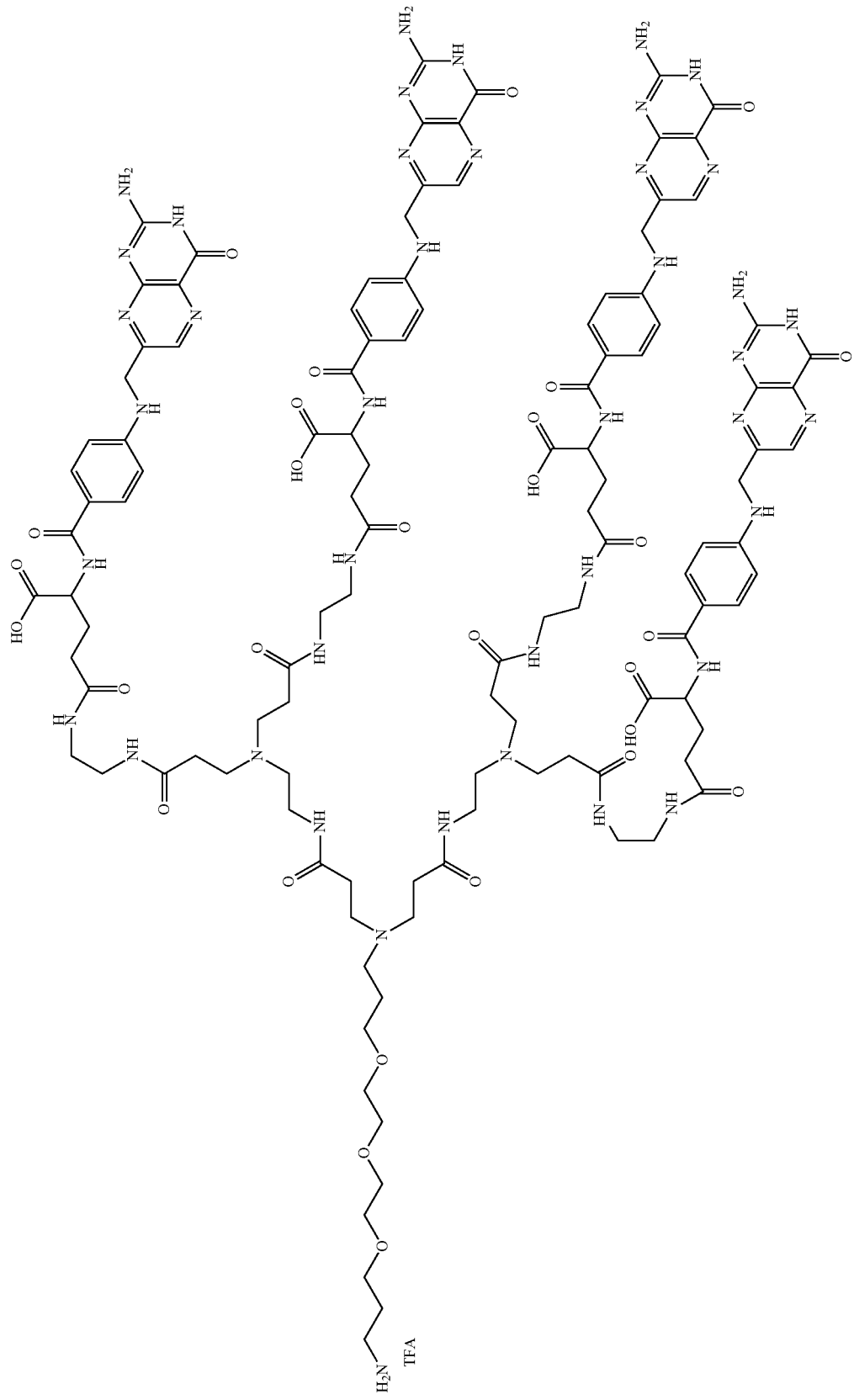

-continued
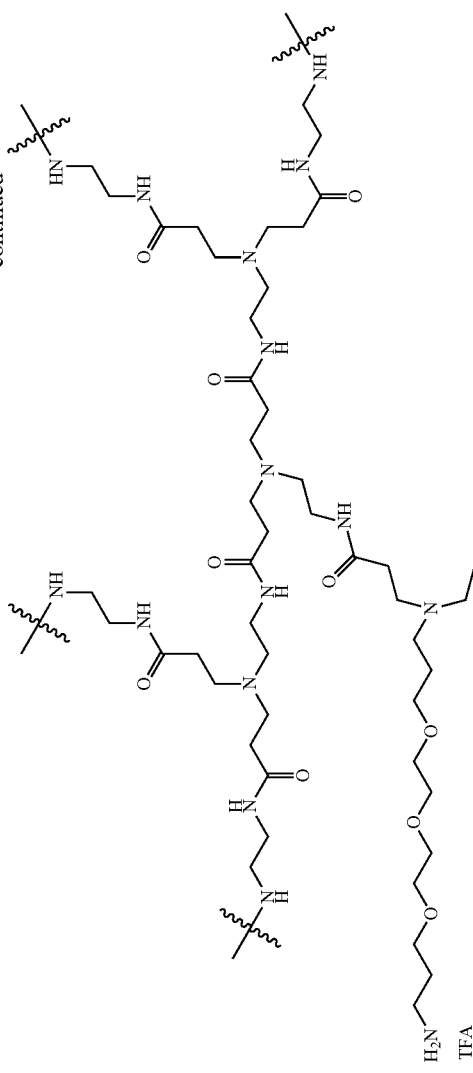
Amino-PEG3-dendrimer-8-folates
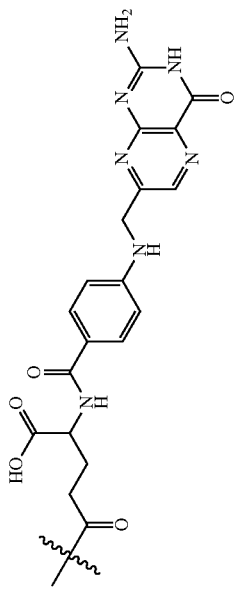
Folate

Similar procedures were used to prepare amino-PEG$_3$-dendrimer-4-folates and amino-PEG$_3$-dendrimer-8-folates, by substituting N-Boc-PEG$_3$-dendrimer G0 with N-Boc-PEG$_3$-dendrimer G1 and N-Boc-PEG$_3$-dendrimer G2, respectively.

Example 12

Synthesis of N-Boc-PEG3-dendrimer-2-glutaric acids

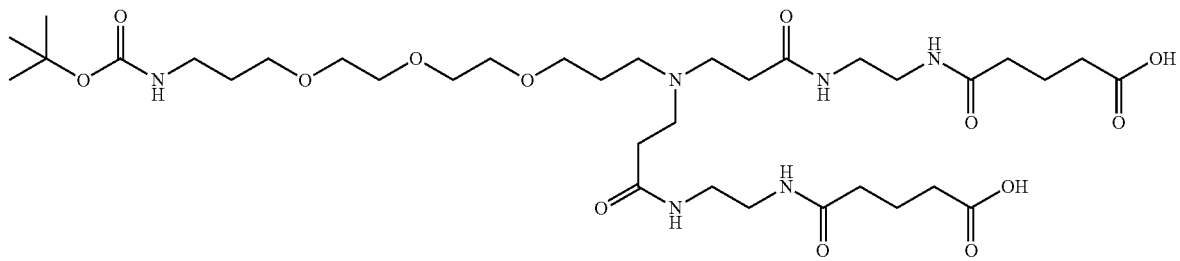

N-Boc-dendrimer-2-glutaric acids

N-Boc-PEG$_3$-dendrimer G0 (50 g) was dissolved in dichloromethane (DCM) (150 mL). Glutaric anhydride (50 g) was added and the reaction mixture was stirred for 15 hours at ambient temperature. The reaction was quenched with sodium hydroxide solution (1 M) until it tested basic by pH paper. The mixture was stirred for 1 hour at ambient temperature and acidified with 3 M HCl until pH about 3-4. The N-Boc-PEG$_3$-dendrimer-2-glutaric acids was extracted in DCM solution, dried with anhydrous sodium sulfate, and DCM was removed by rotary evaporation. The resulting N-Boc-dendrimer-PEG$_3$-2-glutaric acids was obtained (36 g). The product was characterized by $^1$H-NMR analysis.

Example 13

Synthesis of N-Boc-PEG$_3$-dendrimer-2-acids

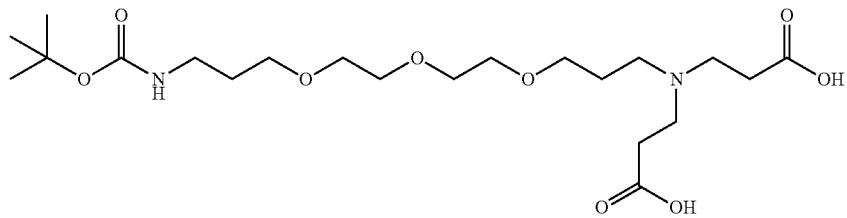

N-Boc-PEG3-dendrimer-2-acids

N-Boc-PEG$_3$-dendrimer-2-methyl ester was prepared in a manner similar to that described in Example 1, hydrolyzed with sodium hydroxide in methanol and converted to N-Boc-PEG$_3$-dendrimer-2-acids with treatment of HCl solution. N-Boc-PEG$_3$-dendrimer-2-acids was extracted in dichloromethane (DCM), dried with anhydrous sodium sulfate, and the DCM was removed by rotary evaporation. The resulting N-Boc-PEG$_3$-dendrimer-2-acids was obtained and was characterized by $^1$H-NMR analysis.

Example 14

Synthesis of N-Boc-PEG$_3$-dendrimer-2-glutaric acid NHS linkers

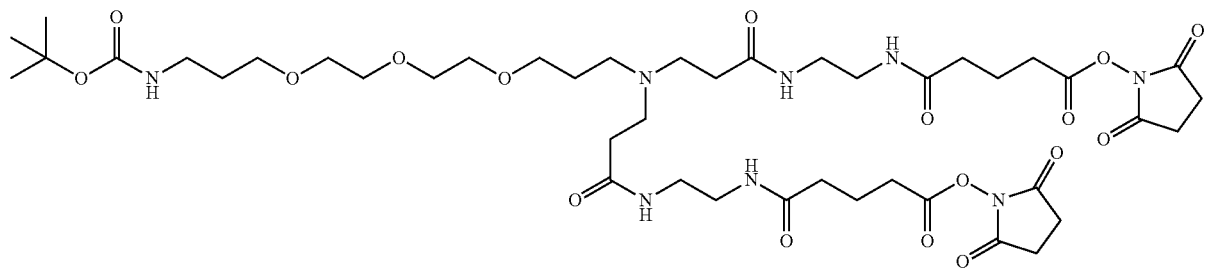

N-Boc-dendrimer-2-glutaric acids NHS

N-Boc-dendrimer-PEG$_3$-2-glutaric acids (36 g) (prepared in a manner similar to that described in Example 12) was dissolved in dichloromethane (DCM) (150 mL). N-hydroxysuccinimide (NHS) (20 g) and EDC (20 g) were added and the reaction mixture was stirred for 15 hours at ambient temperature. The reaction was quenched with water. N-Boc-dendrimer-2-glutaric acid NHS was extracted in DCM solution, dried with anhydrous sodium sulfate, and DCM was removed by rotary evaporation to obtain N-Boc-dendrimer-2-glutaric acid NHS (16 g). The product was characterized by $^1$H-NMR analysis. Those skilled in the art will recognize that the obtained N-Boc-dendrimer-2-glutaric acid NHS is an asymmetrical dendritic compound of Formula (I) in which n is 2, m is 2, $R^1$ is $CO_2C(CH_3)_3$, $X^1$ is absent, L is $C_8$ alkyleneoxide, $X^2$ is $C(=O)(CH_2)_3CO_2$ and $R^2$ is a succinimide group.

Example 15

Synthesis of TFA Amino-dendrimer-linker-2-folates

N-Boc-PEG$_3$-dendrimer-2-glutaric acid NHS (2.0 g) (prepared in a manner similar to that described in Example 12) was dissolved in dichloromethane (DCM) (20 mL). TFA.Amino-PEG$_3$-Folate (3.5 g) (prepared in a manner similar to that described in Example 11) and triethylamine (10 g) were added and the reaction mixture was stirred for 15 hours at ambient temperature. The reaction was quenched with water (30). N-Boc-dendrimer-2 glutaric acid-PEG$_3$-folates was separated from DCM, extracted in water, precipitated upon addition of HCl solution and was filtered, washed with water, and air-dried. The resulting N-Boc-dendrimer-2-glutaric acid-PEG3-folates was further treated with trifluoroacetic acid and the reaction was stirred for 15 hours at ambient temperature. Excess TFA was removed by rotary evaporation to obtain TFA.Amino-PEG$_3$-dendrimer-2-glutaric acid-PEG$_3$-folates (1.8 g). The product was characterized by $^1$H-NMR analysis.

Those skilled in the art will recognize that the obtained TFA Amino-PEG$_3$-dendrimer-2-glutaric acid-PEG$_3$-folates is a TFA salt of an asymmetrical dendritic compound of Formula (I) in which n is 2, m is 2, $R^1$ is H, $X^1$ is absent, L is $C_8$ alkyleneoxide, $X^2$ is a $C(=O)(CH_2)_3C(=O)$—NH—$C_8$alkyleneoxide-NH linker and $R^2$ is a folate targeting ligand.

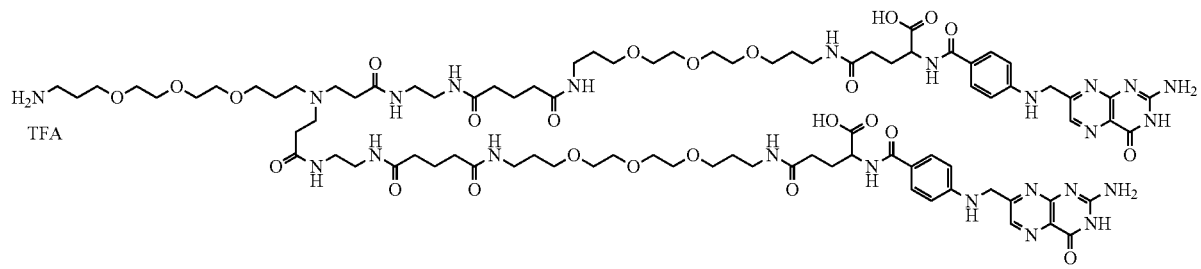

Amino-dendrimer-2-glutaric acid-PEG3-folates

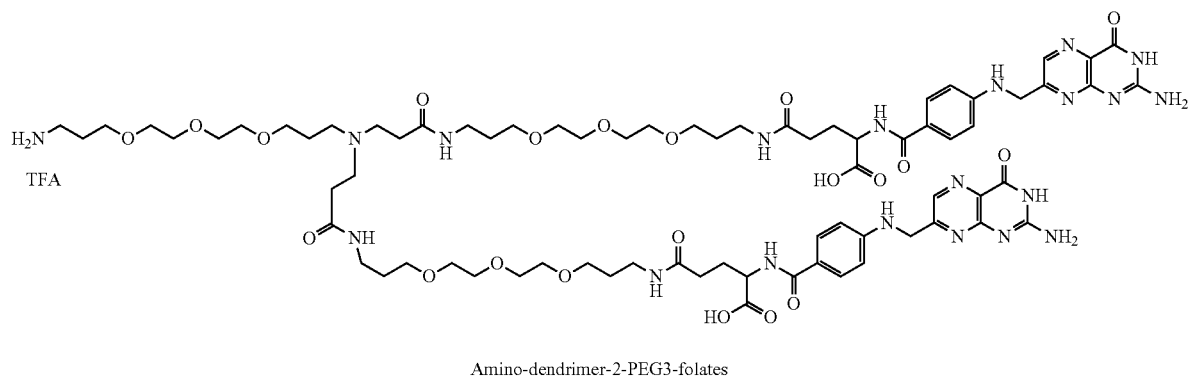 [SMILES: NCCCOCCOCCOCCCN(CCC(=O)NCCCOCCOCCOCCCNC(=O)CCC(NC(=O)c1ccc(NCc2cnc3c(=O)[nH]c(N)nc3n2)cc1)C(=O)O)CCC(=O)NCCCOCCOCCOCCCNC(=O)CCC(NC(=O)c1ccc(NCc2cnc3c(=O)[nH]c(N)nc3n2)cc1)C(=O)O]

Amino-dendrimer-2-PEG3-folates

N-Boc-PEG$_3$-dendrimer-2-methyl ester was hydrolyzed with sodium hydroxide and converted to N-Boc-PEG$_3$-dendrimer-2-carboxylic acid by treatment with HCl. The N-Boc-PEG$_3$-dendrimer-2-carboxylic acid was treated with NHS and EDC and was stirred in dichloromethane (DCM) for 15 hours at ambient temperature. TFA Amino-PEG$_3$-Folate and triethylamine were added and the reaction mixture was stirred for 15 hours at ambient temperature. The reaction was quenched with water (30). N-Boc-dendrimer-2-PEG$_3$-folates was separated from DCM and extracted in water. N-Boc-dendrimer-2-PEG$_3$-folates was precipitated upon addition of HCl solution and was filtered, washed with water, and air-dried. N-Boc-dendrimer-2-PEG$_3$-folates was further treated with trifluoroacetic acid and the reaction was stirred for 15 hours. Excess TFA was removed by rotary evaporation to obtain TFA.Amino-PEG$_3$-dendrimer-2-PEG$_3$-folates. The product was characterized by $^1$H-NMR analysis.

Example 16

Synthesis of hydrazine-glutaric acid-PEG$_3$-dendrimer-2-folates, hydrazine-glutaric acid-PEG3-dendrimer-4-folates, and hydrazine-glutaric acid-PEG$_3$-dendrimer-8-folates N-Boc-hydrazine-glutaric acid NHS (1.0 g) was dissolved in dichloromethane (DCM) (20 mL). TFA.Amino-PEG$_3$-dendrimer-2 folates (4.0 g) and triethylamine (10 g) were added and the reaction mixture was stirred for 15 hours. The reaction was quenched with water (30). The N-Boc-hydrazine-glutaric acid-PEG$_3$-dendrimer-2 folates in the resulting reaction mixture was separated from DCM and extracted in water, precipitated upon addition of HCl solution, filtered, washed with water, and air-dried. N-Boc-hydrazine-glutaric acid-PEG3-dendrimer-2 folates was further treated with trifluoroacetic acid (TFA) and the reaction was stirred for 15 hours. Excess TFA was removed by rotary evaporation. Hydrazine-glutaric acid-dendrimer-2 folates was obtained (2.3 g). The product was characterized by $^1$H-NMR analysis.

Those skilled in the art will recognize that the obtained hydrazine-glutaric acid-dendrimer-2 folates is an asymmetrical dendritic compound of Formula (I) in which n is 2, m is 2, R$^1$ is NH$_2$NH, X$^1$ is C(=O)(CH$_2$)$_3$C(=O), L is C$_8$ alkyleneoxide, X$^2$ is absent and R$^2$ is a folate targeting ligand.

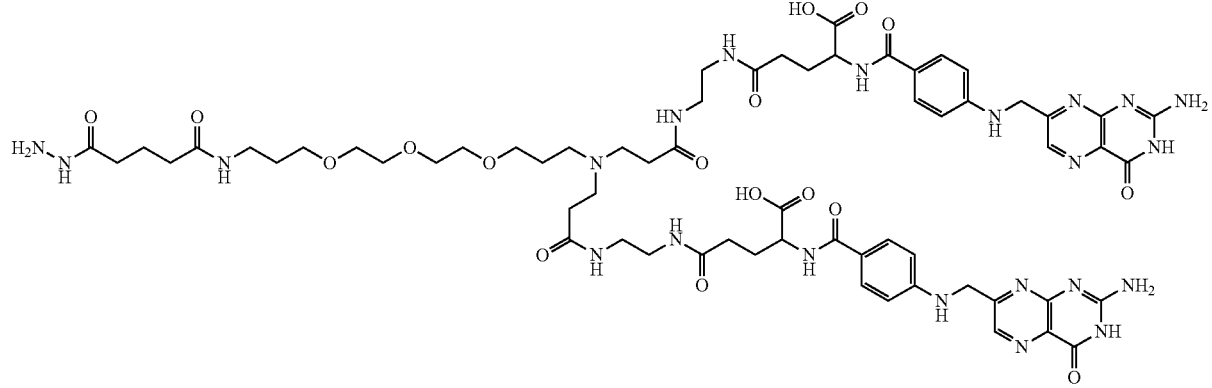

Hydrazine-glutaric acid-PEG3-dendrimer-2-folates

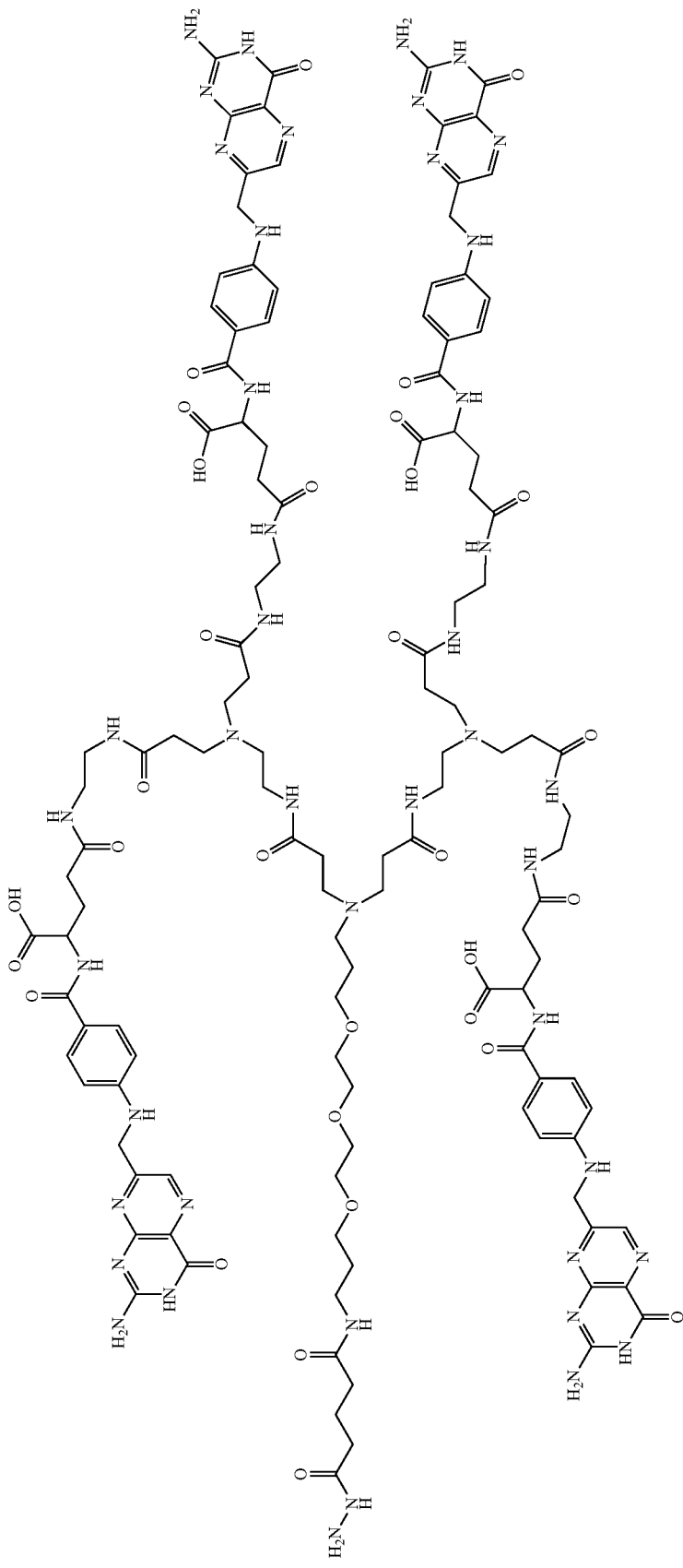
Hydrazine-glutaric acid-PEG3-dendrimer-4-folates

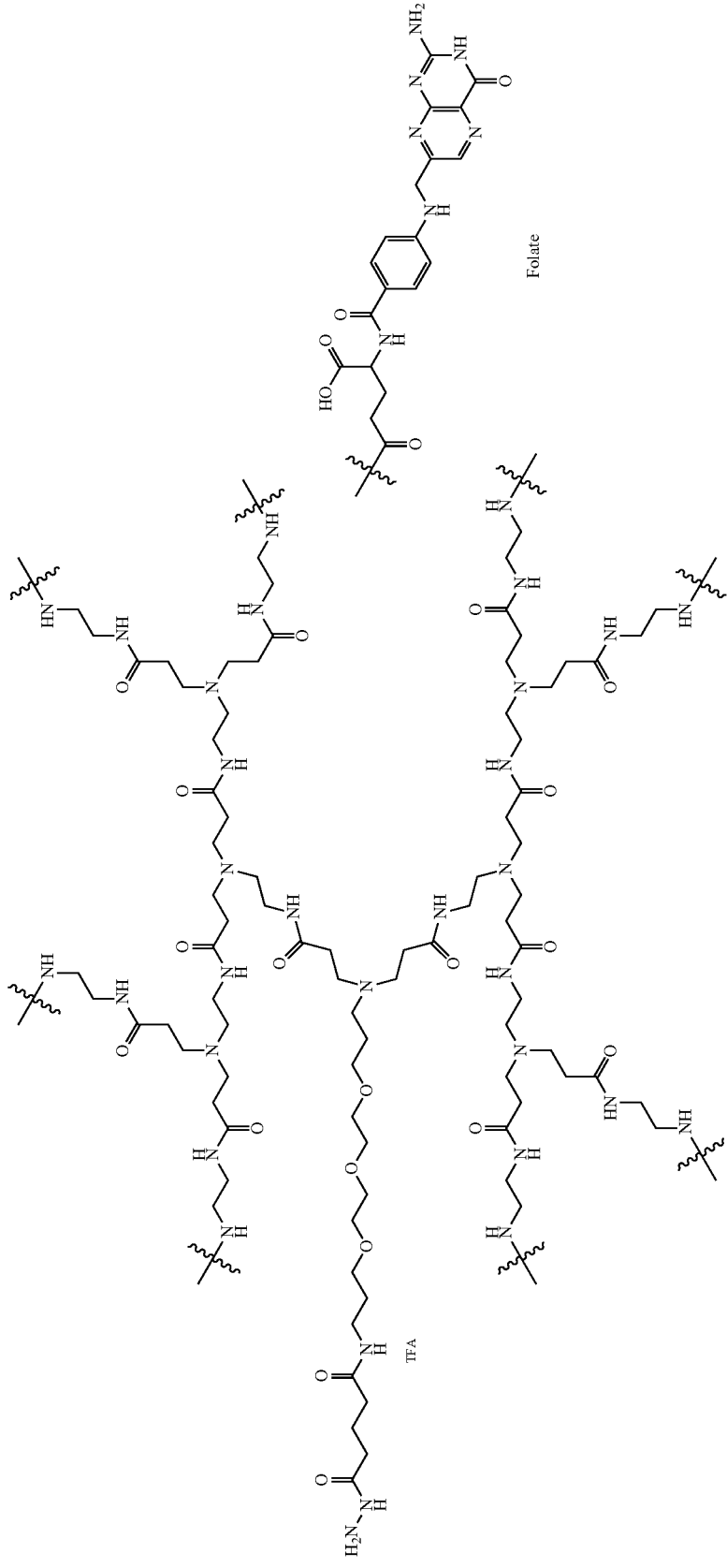

Hydrazine-glutaric acid-PEG$_3$-dendrimer-4-folates and hydrazine-glutaric acid-PEG$_3$-dendrimer-8-folates were prepared using similar procedures with a modification of substituting TFA.Amino-PEG$_3$-dendrimer-2 folates with TFA Amino-PEG3-dendrimer-4 folates and TFA.Amino-PEG$_3$-dendrimer-8 folates, respectively.

Example 17

Synthesis of hydrazine-glutaric acid-PEG$_3$-dendrimer-2-linker-folates

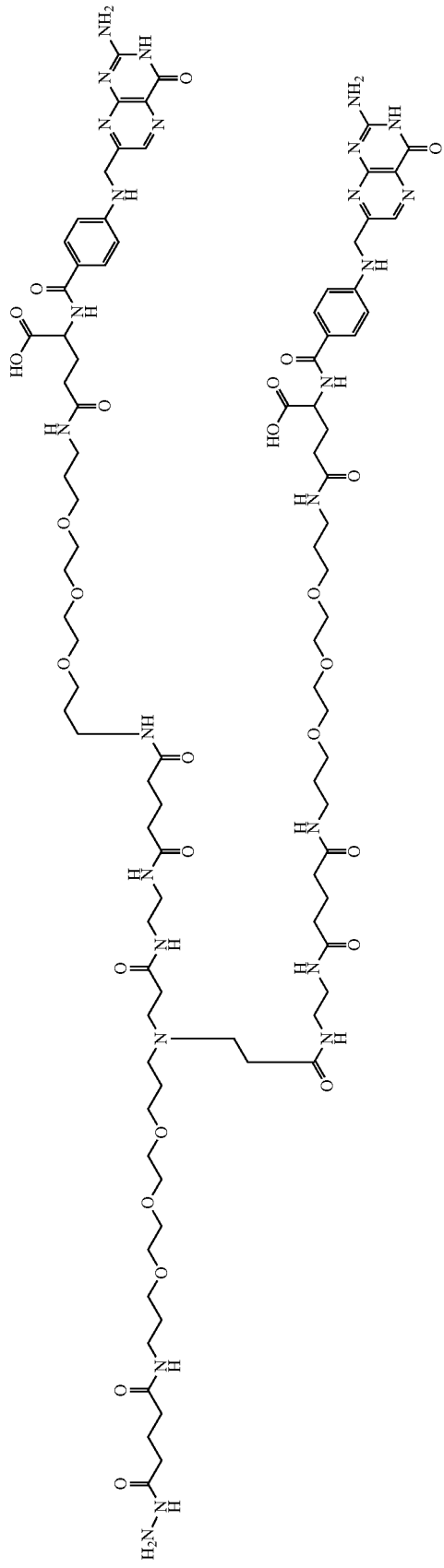

N-Boc-hydrazine-glutaric acid NHS (1.0 g) was dissolved in dichloromethane (DCM) (20 mL). TFA.Amino-PEG3-dendrimer-2-glutaric acid-$PEG_3$-folates (5.0 g) and triethylamine (10 g) were added and the reaction mixture was stirred for 15 hours at ambient temperature. The reaction was quenched with water (30 mL). N-Boc-hydrazine-glutaric acid-PEG3-dendrimer-2-glutaric acid-$PEG_3$-folates was separated from DCM, extracted in water, precipitated upon addition of HCl solution, filtered, washed with water, and air-dried. N-Boc-hydrazine-glutaric acid-PEG3-dendrimer-2-glutaric acid-$PEG_3$-folates was further treated with trifluoroacetic acid (TFA) and the reaction was stirred for 15 hours at ambient temperature. Excess TFA was removed by rotary evaporation. Hydrazine-glutaric acid-PEG3-dendrimer-2-glutaric acid-$PEG_3$-folates was obtained (2.2 g). The product was characterized by $^1$H-NMR analysis.

Those skilled in the art will recognize that the obtained hydrazine-glutaric acid-$PEG_3$-dendrimer-2-glutaric acid-$PEG_3$-folates is an asymmetrical dendritic compound of Formula (I) in which n is 2, m is 2, $R^1$ is $NH_2NH$, $X^1$ is $C(=O)(CH_2)_3C(=O)$, L is $C_8$ alkyleneoxide, $X^2$ is $C(=O)(CH_2)_3C(=O)$—NH—$C_8$alkyleneoxide-NH and $R^2$ is a folate targeting ligand.

Example 18

Synthesis of doxorubicin-hydrazine-glutaric acid-$PEG_3$-dendrimer-2-folates, doxorubicin-hydrazine-glutaric acid-$PEG_3$-dendrimer-4-folates, and doxorubicin-hydrazine-glutaric acid-$PEG_3$-dendrimer-8-folates

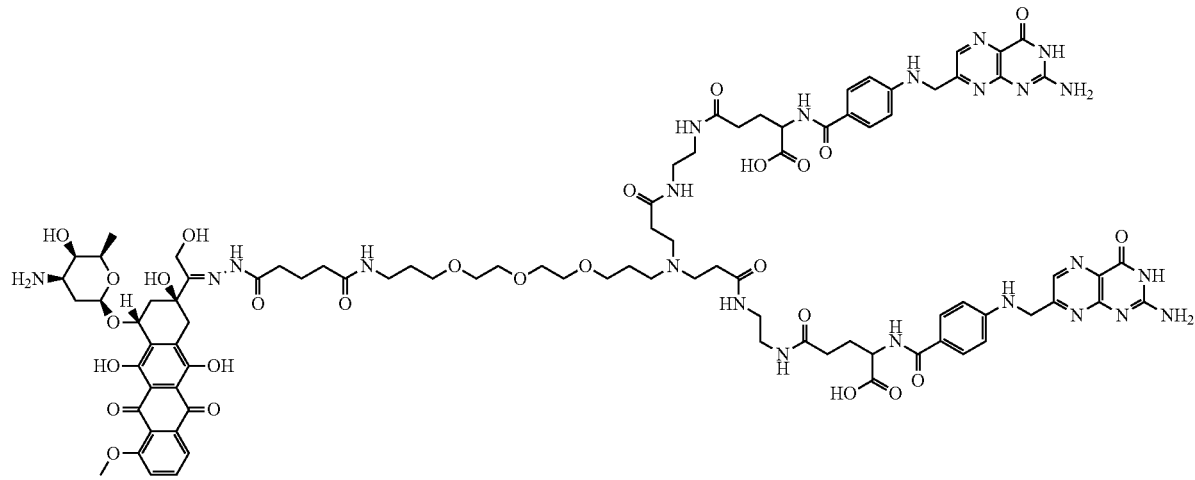

Doxorubicin-hydrazone-glutaric acid-PEG3-dendrimer-2-folates

Hydrazine-glutaric acid-$PEG_3$-dendrimer-2-folates (460 mg) was dissolved in dichloromethane (DCM) (20 mL). Doxorubicin (200 mg), TFA (1 mL), and sodium sulfate (2 g) were added. The reaction mixture was stirred for 2 days. Doxorubicin-hydrazine-glutaric acid-$PEG_3$-dendrimer-2-folates was precipitated out the solution, filtered, washed with DCM, water, and acetone. The resulting doxorubicin-hydrazine-glutaric acid-$PEG_3$-dendrimer-2-folates product was obtained after being air-dried (150 mg). The product was characterized by $^1$H-NMR analysis.

Those skilled in the art will recognize that the obtained doxorubicin-hydrazine-glutaric acid-$PEG_3$-dendrimer-2-folates is an asymmetrical dendritic compound of Formula (I) in which n is 2, m is 2, $R^1$ is doxorubicin, $X^1$ is $C(=O)(CH_2)_3C(=O)$, L is $C_8$ alkyleneoxide, $X^2$ is absent and $R^2$ is a folate targeting ligand.

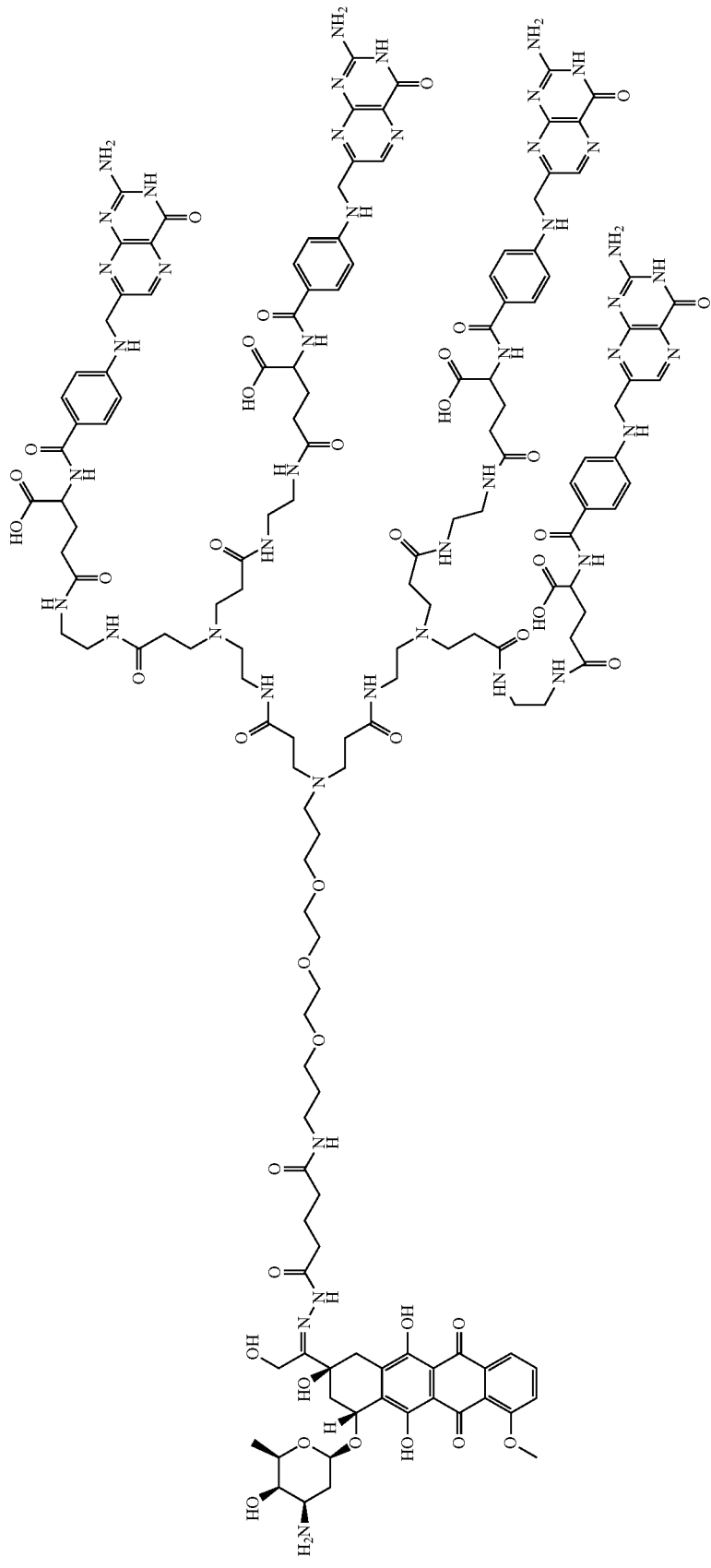
Doxorubicin-hydrazone-glutaric acid-PEG3-dendrimer-4-folates

-continued
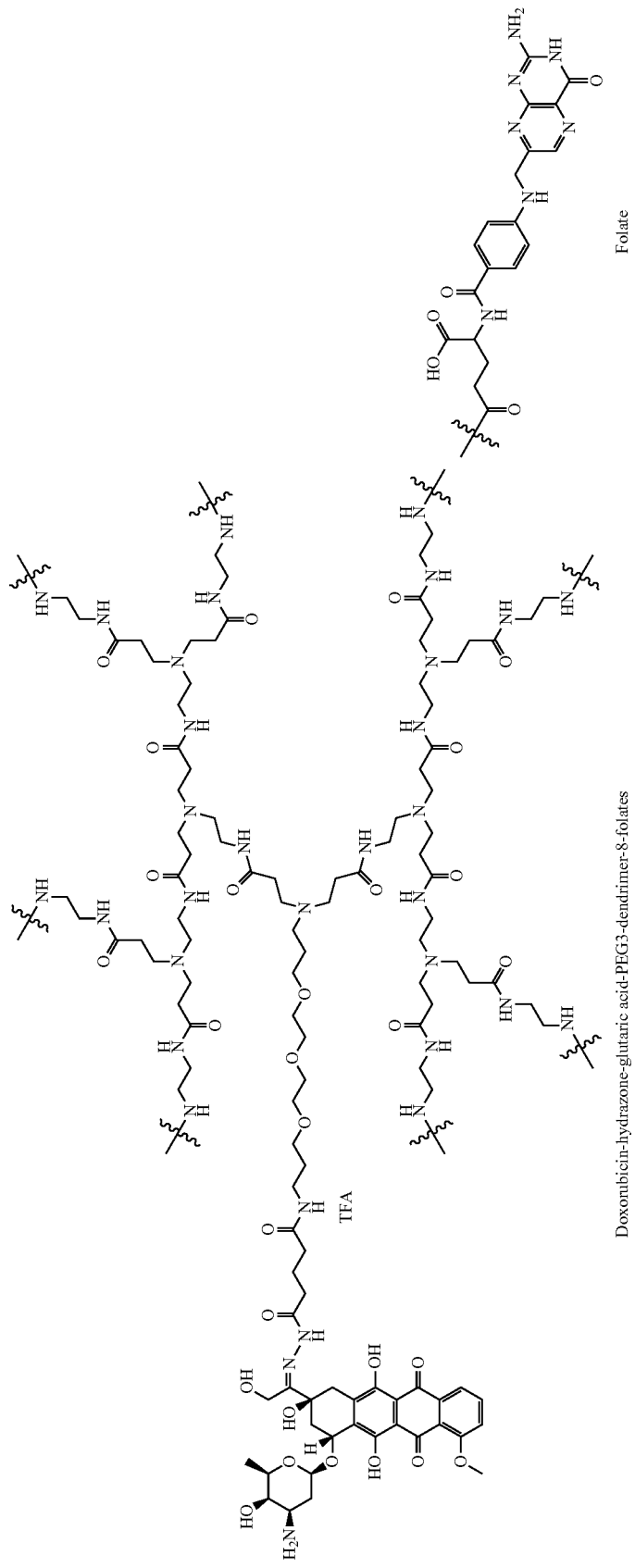
Doxorubicin-hydrazone-glutaric acid-PEG3-dendrimer-8-folates Doxorubicin-hydrazone-glutaric acid-PEG$_3$-dendrimer-4-folates and doxorubicin-hydrazone-glutaric acid-PEG$_3$-dendrimer-8-folates were prepared in a manner similar to the procedure used to make doxorubicin-hydrazone-glutaric acid-PEG$_3$-dendrimer-2-folates with a modification of substituting hydrazine-glutaric acid-PEG$_3$-dendrimer-2 folates with hydrazine-glutaric acid-PEG$_3$-dendrimer-4 folates and hydrazine-glutaric acid-PEG$_3$-dendrimer-8 folates, respectively.

Example 19

Synthesis of doxorubicin-hydrazine-glutaric acid-PEG$_3$-dendrimer-2-glutaric acid-PEG$_3$-folates

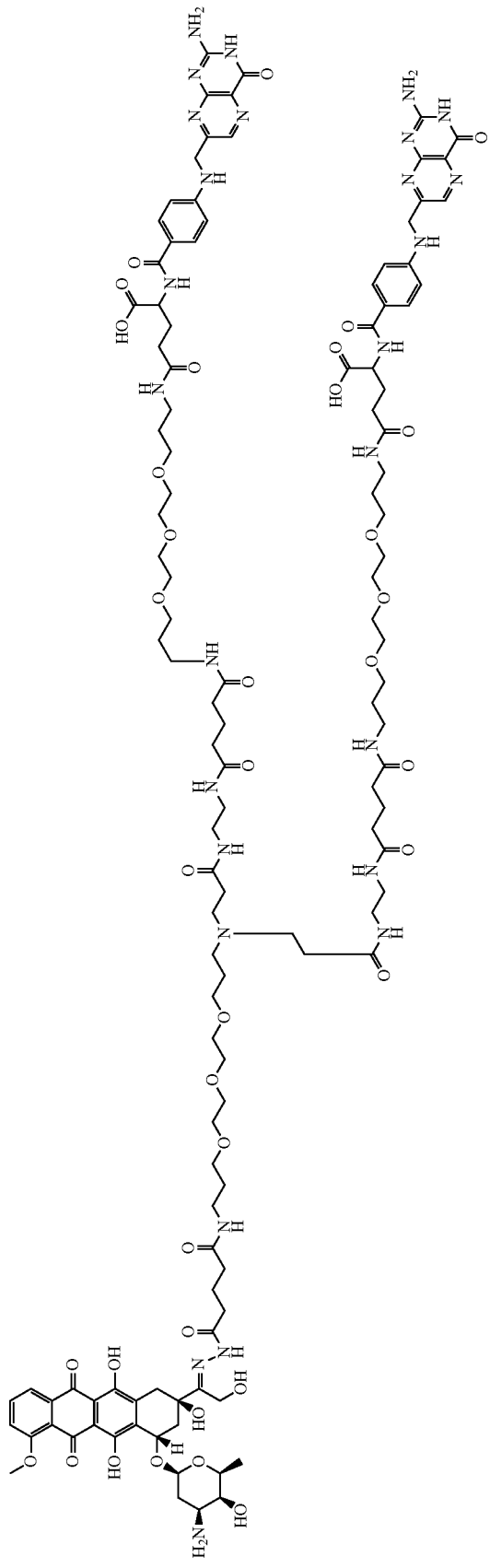

Doxorubicin-hydrazone-glutaric acid-PEG$_3$-dendrimer-2-glutaric acid-PEG$_3$-folates was prepared in a manner similar to the procedure used to make doxorubicin-hydrazone-glutaric acid-PEG$_3$-dendrimer-2-folates with a modification of substituting hydrazine-glutaric acid-PEG$_3$-dendrimer-2 folates with hydrazine-glutaric acid-PEG$_3$-dendrimer-2-glutaric acid-PEG$_3$-folates.

Example 20

Synthesis of other drug derivatives

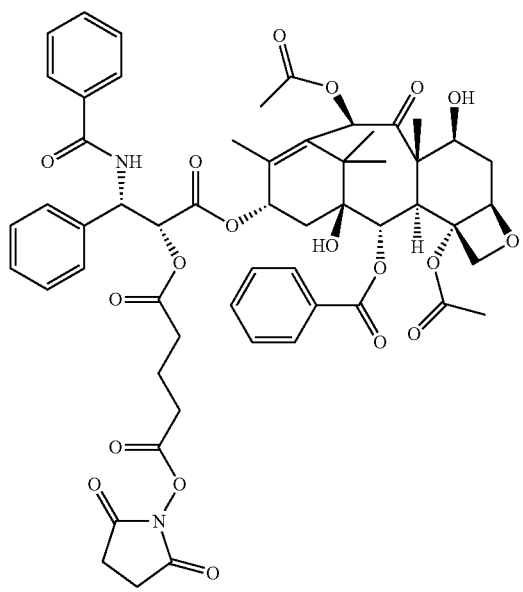

Paclitaxel-glutaric acid-NHS

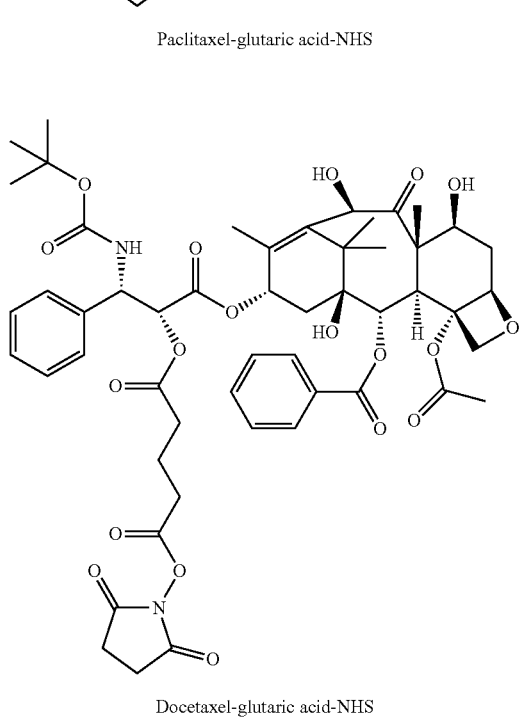

Docetaxel-glutaric acid-NHS

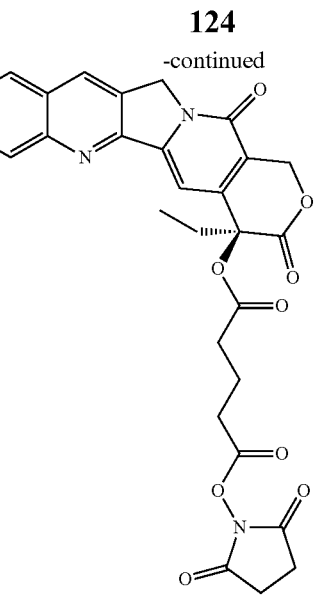

Campthothecin-glutaric acid-NHS

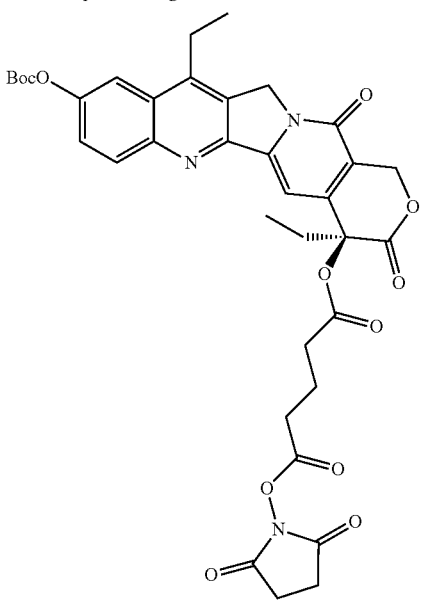

SN-38-glutaric acid-NHS

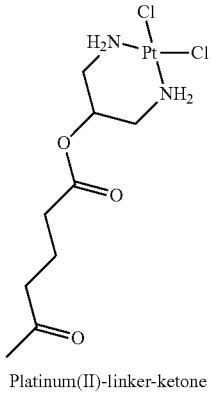

Platinum(II)-linker-ketone

Other drug derivatives can be synthesized according to procedures published in the literature.

Synthesis of paclitaxel-glutaric acid-NHS and docetaxel-glutaric acid-NHS can be carried out according to procedures published in Auzenne et al. (Auzenne E, Ghosh S C, Khodadadian M, Rivera B, Farquhar D, Price R E, Ravoori M, Kundra V, Freedman R S, Klostergaard J. Hyaluronic acid-paclitaxel: antitumor efficacy against CD44(+) human ovarian carcinoma xenografts. Neoplasia. 2007; 9(6):479-86).

Synthesis of camptothecin-glutaric acid-NHS and SN-38-glutaric acid-NHS can be carried out according to procedures published in Yao et. al. (Yao Y, Su X, Xie Y, Wang Y, Kang T, Gou L, Yi C, Yang J. Synthesis, characterization, and antitumor evaluation of the albumin-SN38 conjugate. Anticancer Drugs. 2013, 24, 270-7).

Platinum(II)-linker-ketone can be prepared according to procedures published in Binauld et al. (Binauld S, Scarano W, Stenzel M H. pH-Triggered Release of Platinum Drugs Conjugated to Micelles via an Acid-Cleavable Linker. Macromolecules, 2012, 45 (17):6989-6999).

Vinblastine, vincristine, and vinorelbine derivatives can be prepared according to procedures published in Barnett et al. (Barnett, C. J.; Cullinan, G. J.; Gerzon, K.; Hoying, R. C.; Jones, W. E.; Newlon, W. M.; Poore, G. A.; Robison, R. L.; Sweeney, M. J.; Todd, G. C. Structure-activity relationships of dimeric Catharanthus alkaloids. 1. Deacetylvinblastine amide (vindesine) sulfate. J. Med. Chem. 1978, 21, 88).

Other drug derivatives generated from drugs such as combretastin A-4, etoposide, teniposide, auristatin, calicheamicin, maytansinoid, and duocarmycin can be synthesized according to procedures published in the literature ((1) Schobert R, Biersack B, Dietrich A, Knauer S, Zoldakova M, Fruehauf A, Mueller T. Pt(II) complexes of a combretastatin A-4 analogous chalcone: effects of conjugation on cytotoxicity, tumor specificity, and long-term tumor growth suppression. J Med Chem. 2009 Jan. 22; 52(2):241-6; (2) Zheng N, Pang S, Oe T, Felix C A, Wehrli S, Blair I A. Characterization of an etoposide-glutathione conjugate derived from metabolic activation by human cytochrome p 450. Curr Drug Metab. 2006 December; 7(8):897-911; (3) Francisco J A, Cerveny C G, Meyer D L, Mixan B J, Klussman K, Chace D F, Rejniak S X, Gordon K A, DeBlanc R, Toki B E, Law C L, Doronina S O, Siegall C B, Senter P D, Wahl A F. cAC10-vcMMAE, an anti-CD30-monomethyl auristatin E conjugate with potent and selective antitumor activity. Blood. 2003 Aug. 15; 102(4):1458-65; (4) Boghaert E R, Sridharan L, Armellino D C, Khandke K M, DiJoseph J F, Kunz A, Dougher M M, Jiang F, Kalyandrug L B, Hamann P R, Frost P, Damle N K. Antibody-targeted chemotherapy with the calicheamicin conjugate hu3S193-N-acetyl gamma calicheamicin dimethyl hydrazide targets Lewisy and eliminates Lewisy-positive human carcinoma cells and xenografts. Clin Cancer Res. 2004 Jul. 1; 10(13): 4538-49; (5) Erickson H K, Park P U, Widdison W C, Kovtun Y V, Garrett L M, Hoffman K, Lutz R J, Goldmacher V S, Blattler W A. Antibody-maytansinoid conjugates are activated in targeted cancer cells by lysosomal degradation and linker-dependent intracellular processing. Cancer Res. 2006 Apr. 15; 66(8):4426-33; (6) Suzawa T, Nagamura S, Saito H, Ohta S, Hanai N, Yamasaki M. Synthesis of a novel duocarmycin derivative DU-257 and its application to immunoconjugate using poly(ethylene glycol)-dipeptidyl linker capable of tumor specific activation. Bioorg Med Chem. 2000 August; 8(8):2175-84).

Example 21

The drug derivatives described in Example 20 can be used to make drug- and targeting ligand-containing asymmetrical dendritic compounds as described herein. For example, the drug derivatives can be conjugated onto $PEG_3$-dendrimer-2-folates, $PEG_3$-dendrimer-4-folates, $PEG_3$-dendrimer-8-folates, $PEG_3$-dendrimer-16-folates, $PEG_3$-dendrimer-2-linker-folates, $PEG_3$-dendrimer-4-linker-folates, $PEG_3$-dendrimer-8-linker-folates, and $PEG_3$-dendrimer-16-linker-folates, as illustrated below:

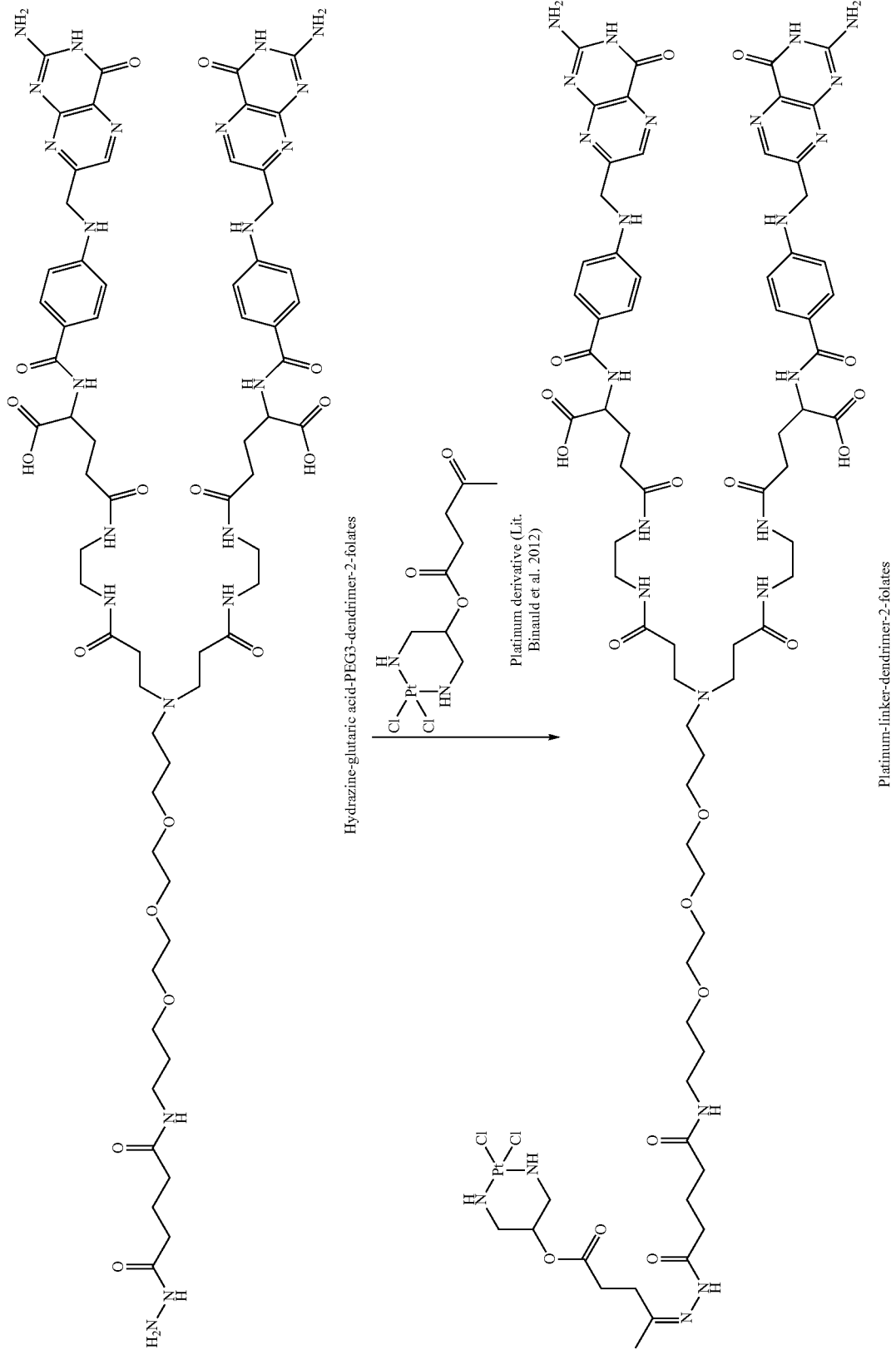

Example 22

The drug derivatives described in Example 20 can be used to make other drug- and targeting ligand-containing asymmetrical dendritic compounds as described herein. For example, the drug derivatives can be conjugated onto $PEG_3$-dendrimer-2-linker-cyclic RGD peptides, $PEG_3$-dendrimer-4-linker-cyclic RGD peptides, $PEG_3$-dendrimer-8-linker-cyclic RGD peptides, and $PEG_3$-dendrimer-16-linker-cyclic RGD peptides, as illustrated below:

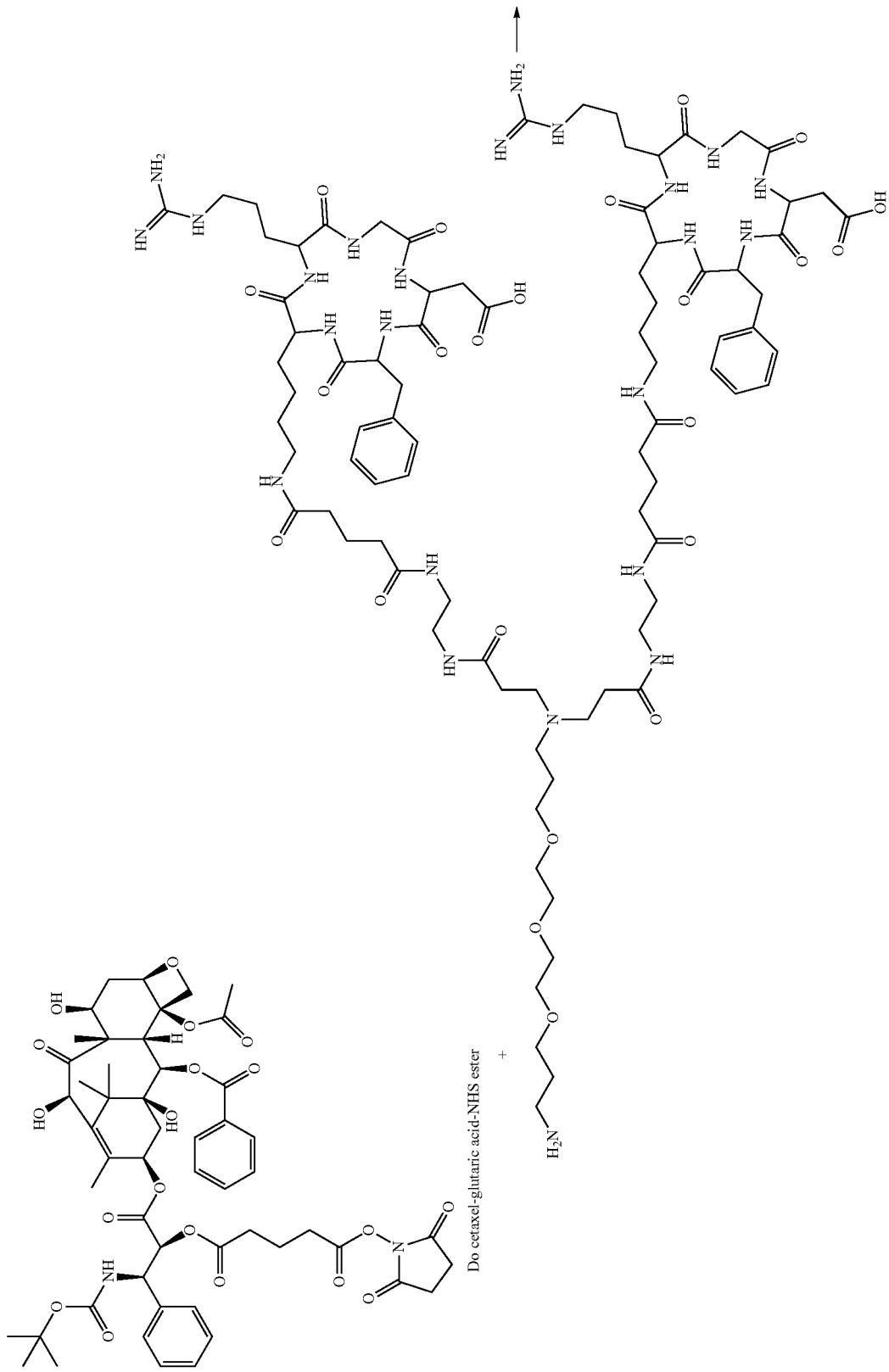

-continued
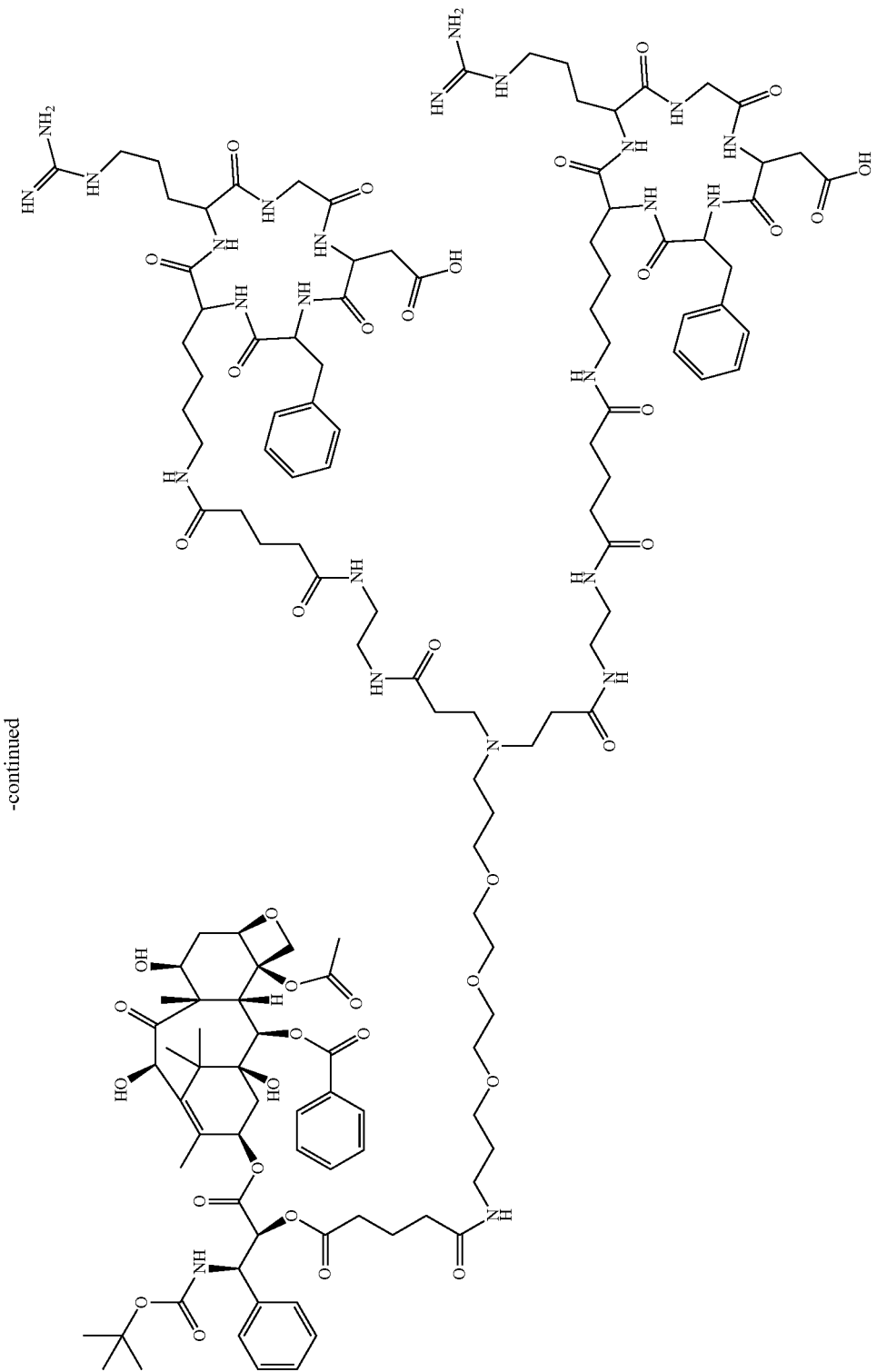
Docetaxel-linker-dendrimer-2-linker-cyclic RGD peptides

The drug derivatives described in Example 20 and doxorubicin derivatives can be used to make maleimide-dendrimer-drug derivatives. For example, the drug derivatives can be conjugated onto maleimide-dendrimers to become maleimide-PEG$_3$-dendrimer-2-drug derivatives, maleimide-PEG$_3$-dendrimer-4-drug derivatives, maleimide-PEG$_3$-dendrimer-8-drug derivatives, maleimide-PEG$_3$-dendrimer-16-drug derivatives, maleimide-PEG$_3$-dendrimer-2-linker-drug derivatives, maleimide-PEG$_3$-dendrimer-4-linker-drug derivatives, maleimide-PEG$_3$-dendrimer-8-linker-drug derivatives, and maleimide-PEGS-dendrimer-16-linker drug derivatives, as illustrated below:

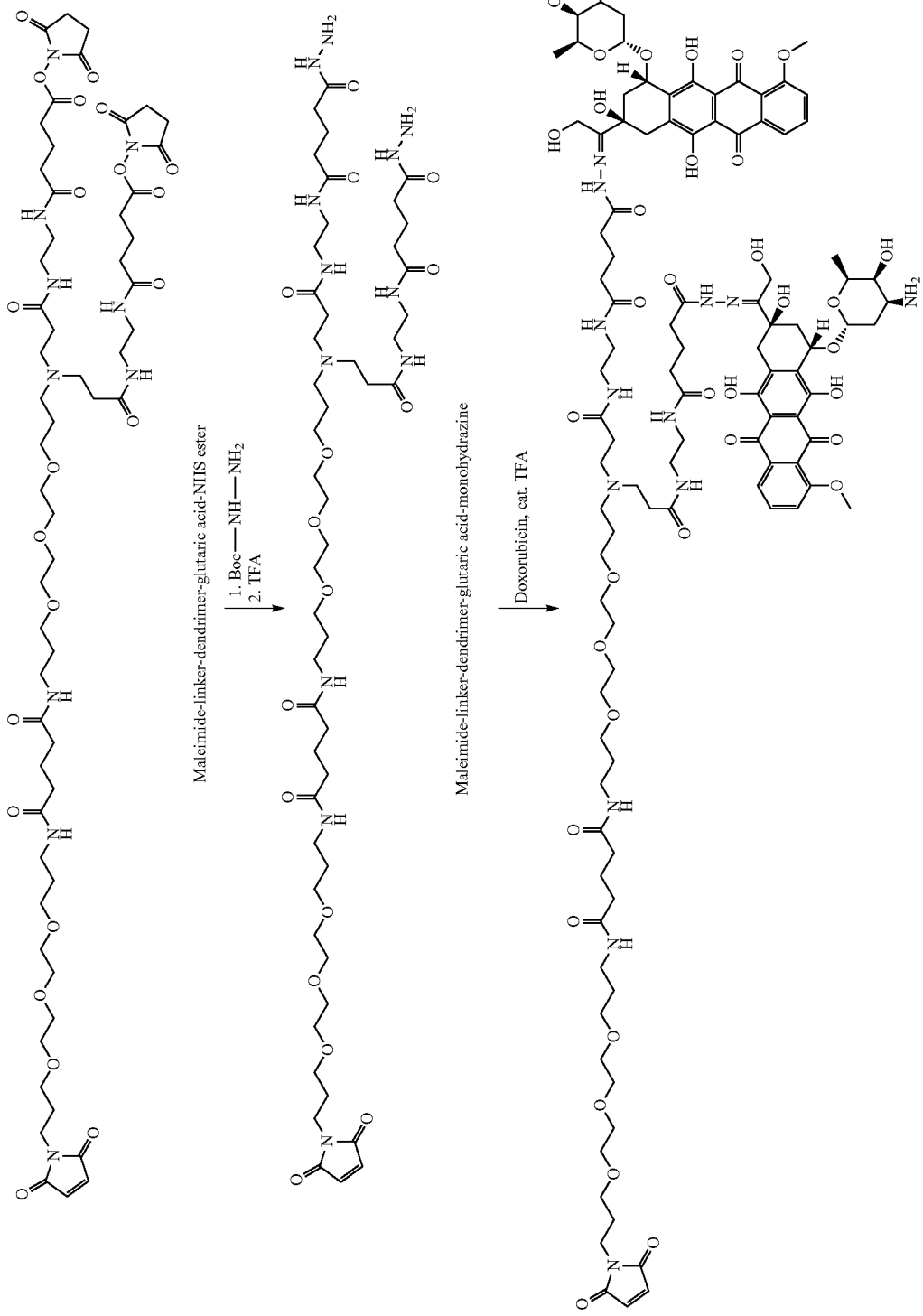

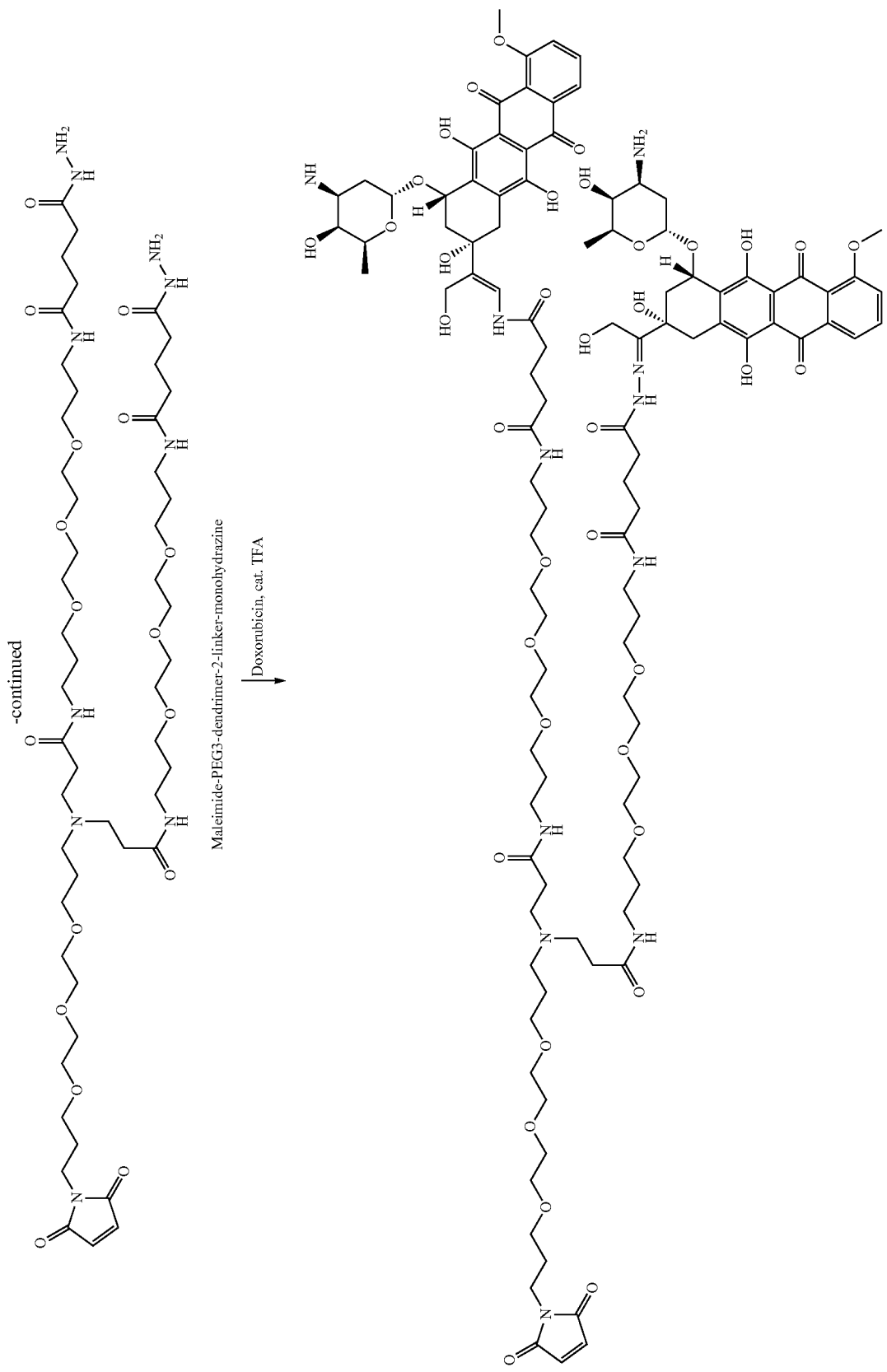

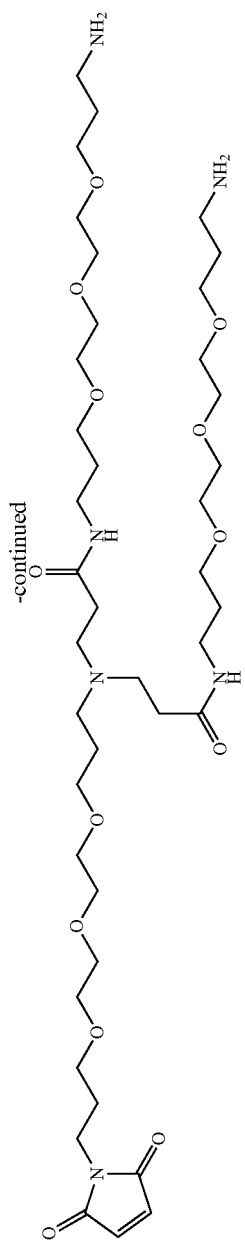
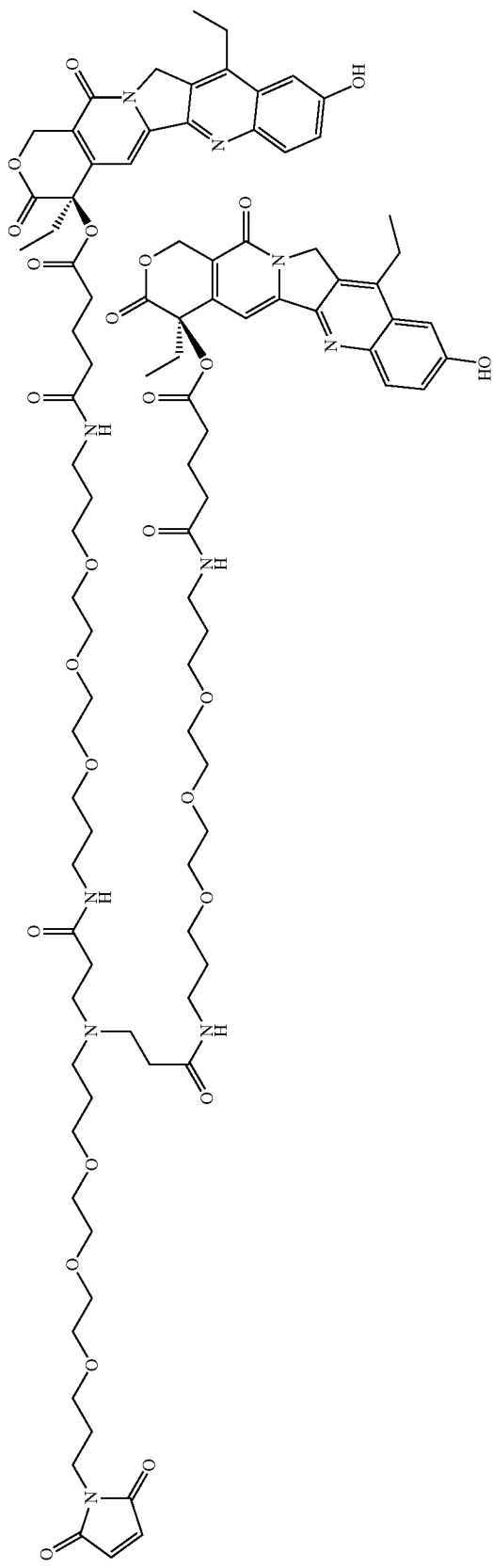

Example 23

Cell Culture and Preparation

Ovarian cancer cells were purchased from ATCC (CRL-6322, ATCC American Type Culture Collection, Rockville, Md.) and were grown in Dulbecco's modified Eagle's medium (DMEM) with 10% fetal bovine serum and 100 units/mL penicillin. The cells were grown at 37° C. in 5% $CO_2$ environment. The culture medium was removed and discarded. The cells were rinsed with Dulbecco Phosphate Buffer Solution (DPBS), Trypsin-ethylenediaminetetra-acetic acid (EDTA) solution (0.5 ml) was added, and the cells were observed under an inverted microscope to make sure that they were dispersed. Complete growth medium (6.0 to 8.0 ml) was added, and the cells were aspirated by gently pipetting. The cell suspension in appropriate aliquots was transferred to new culture plates. The cells were allowed to grow at 37° C. in 5% $CO_2$ for 24 hours before further experiments. Breast, prostate, lung, colon, pancreas cancer cells can be obtained from ATCC and prepared similarly.

Example 24

In Vitro Cytotoxicity MTT and Drug Uptake Studies

Drug-dendrimer-folates as described herein are evaluated for their effect on the proliferation of cancer cells at several different concentrations of the drug. Cytotoxic MTT assay is carried out as reported in Monks et al. JNCI 1991, 83, 757-766, which is hereby incorporated by reference in its entirety.

Example 25

Figure 8:
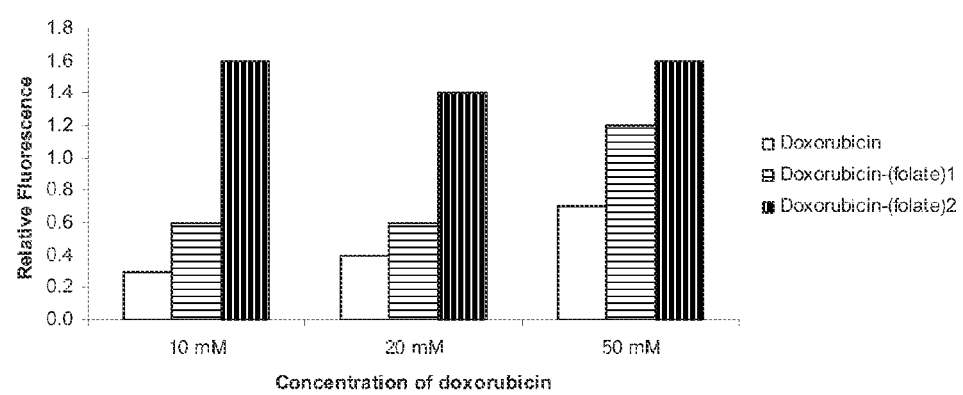
FIG. 8 is a bar graph showing the uptake of doxorubicin and conjugates of doxorubicin-(folate)$_1$ and doxorubicin-dendrimer-(folate)$_2$ in ovarian cancer cell lines. The results show that doxorubicin with 2 folic acids conjugated had superior uptake by ovarian cancer cell lines.

The evaluation of doxorubicin-dendrimer-folate uptake is conducted by using a literature procedure (Kim D, Lee E S, Oh K T, Gao Z G, Bae Y H. Doxorubicin-loaded polymeric micelle overcomes multidrug resistance of cancer by double-targeting folate receptor and early endosomal pH. Small. 2008 November; 4(11):2043-50) and folate-quenching correction was adjusted based on a literature procedure (Husseini G. A., 2012. Folic Acid Quenches Doxorubicin Fluorescence. Advanced Science Letters. 7:726). The results are summarized in FIG. 8. The results show that the presence of the folate significantly enhanced uptake.

Example 26

Animals and Tumor Models

Nude mice (6-7 week old, body weight 25-30 g, male) are purchased from Charles River Lab (Willington, Mass.). The cancer cells harvested from tissue culture are counted and re-suspended to a concentration of $5 \times 10^6$ per mL. Using a TB syringe, 0.2 mL (a total of about $1 \times 10^6$ cells) is administered via subcutaneous injection into each mouse. One tumor is inoculated per animal at the right hip. The site of tumor inoculation is shaved prior to inoculation to make it easier to measure the tumor as it grows.

Example 27

Magnetic Resonance Imaging for Tumor Accumulation

Images of mice are acquired on a GE 3T MR scanner using a knee coil pre- and post-contrast. The following imaging parameters are used: minful, TR=250 ms, FOV: 8 and 24 slices/slab, and 1.0 mm coronal slice thickness. The control material is Omniscan-Gd(III)-(DTPA-BMA (0.1 mmol Gd(III)/kg). The dose of injection of the imaging-dendrimer-folate and Omniscan control material is 0.1 mmol Gd(III)/kg. The two compounds are injected via a tail vein into anesthetized mice and images are acquired at pre-injection and at 6 minutes to 4 hours post-injection of the contrast agents.

Example 28

Synthesis of paclitaxel-$PEG_3$-(folate)$_1$

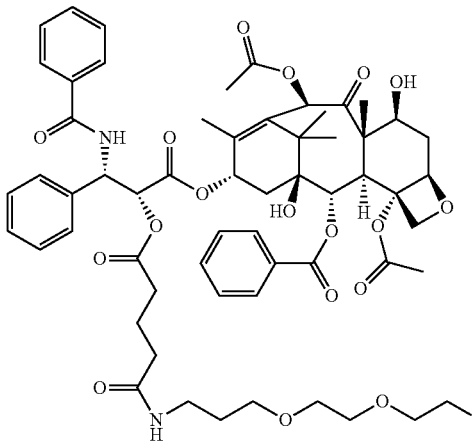
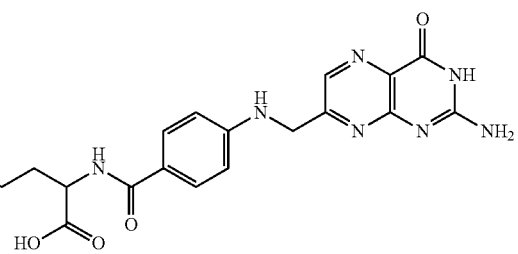

A solution of TFA Amino-$PEG_3$-folate (250 mg) in DMF (10 mL) was added with triethylamine (1 mL) and the mixture reaction was stirred for 20 minutes. Paclitaxel-glutaric acid-N-hydroxysuccinimide (made in a manner similar to that described in Thierry B, Kujawa P, Tkaczyk C, Winnik F M, Bilodeau L, Tabrizian M. Delivery platform for hydrophobic drugs: prodrug approach combined with self-assembled multilayers. J Am Chem Soc. 2005, 127, 1626-7) (300 mg) was added into the reaction mixture, and the reaction mixture was continued to stir for 15 hours. After 15 hours, precipitate was formed when acetone (150 mL) was added. Paclitaxel-PEG$_3$-(folate)$_1$ was filtered off and redissolved in a basic solution (pH 8). Precipitate of paclitaxel-PEG$_3$-(folate)$_1$ was formed by adding a solution of diluted hydrochloric acid until pH around 3. The product was filtered, washed with water, and acetone, and air-dried, and collected to be 90 mg. The compound was characterized by $^1$H-NMR.

Example 29

Synthesis of paclitaxel-dendrimer-(folate)$_1$

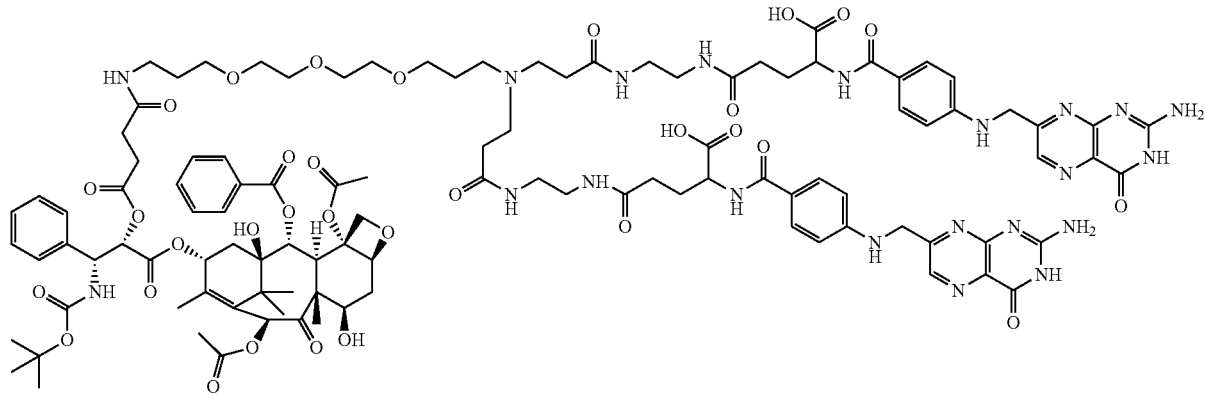 [SMILES: CC(=O)O[C@@H]1C(=O)[C@@]2(C)[C@H](O)C[C@@H]3OC[C@]3(OC(C)=O)[C@@H]2[C@@H](OC(=O)c2ccccc2)[C@@]2(O)C[C@@H](OC(=O)[C@@H](OC(=O)CCC(=O)NCCCOCCOCCOCCCN(CCC(=O)NCCNC(=O)CCC(NC(=O)c3ccc(NCc4cnc5c(=O)[nH]c(N)nc5n4)cc3)C(=O)O)CCC(=O)NCCNC(=O)CCC(NC(=O)c3ccc(NCc4cnc5c(=O)[nH]c(N)nc5n4)cc3)C(=O)O)[C@H](NC(=O)OC(C)(C)C)c3ccccc3)C(C)=C1C2(C)C]

A solution of TFA.Amino-PEG$_3$-dendrimer-2 folates (350 mg) in DMF (10 mL) was added with triethylamine (1 mL) and the mixture reaction was stirred for 20 minutes. Paclitaxel-glutaric acid-N-hydroxysuccinimide (made in a manner similar to that described in Thierry B, Kujawa P, Tkaczyk C, Winnik F M, Bilodeau L, Tabrizian M. Delivery platform for hydrophobic drugs: prodrug approach combined with self-assembled multilayers. J Am Chem Soc. 2005, 127, 1626-7) (160 mg) was added into the reaction mixture, and the reaction mixture was continued to stir for 15 hours. After 15 hours, precipitate was formed when acetone (150 mL) was added. Paclitaxel-dendrimer-(folate)$_2$ was filtered off and redissolved in a basic solution (pH 8). Precipitate of paclitaxel-dendrimer-(folate)$_2$ was formed by adding a solution of diluted hydrochloric acid until pH 3. The product was filtered, washed with water, and acetone, and air-dried, and collected to be 120 mg. The compound was characterized by $^1$H-NMR.

Example 30

Synthesis of docetaxel-PEG$_3$-(folate)$_1$

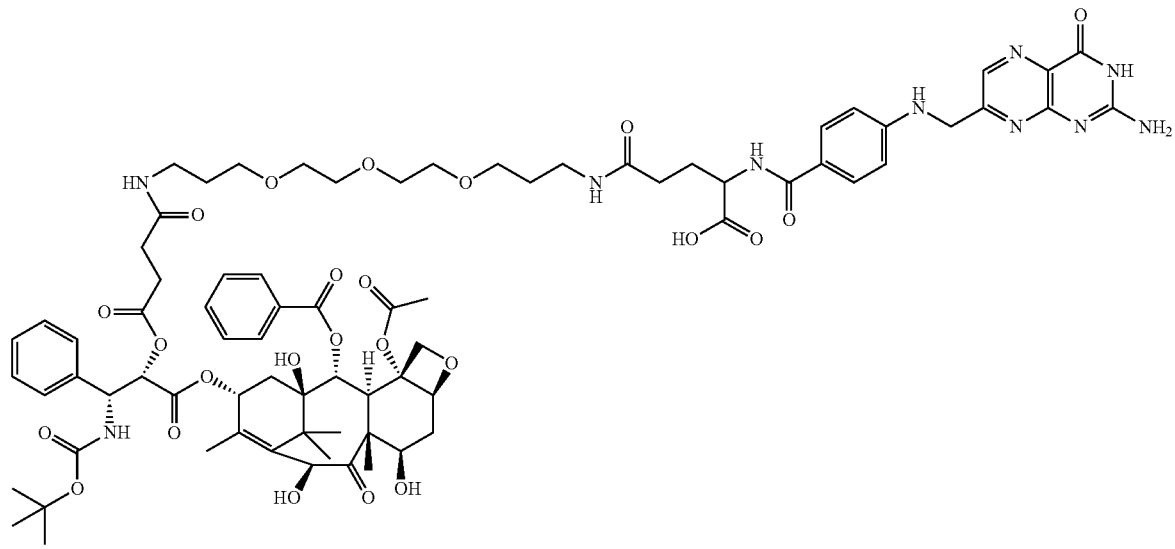 [SMILES: CC(=O)O[C@]12CO[C@H]1C[C@@H](O)[C@]1(C)C(=O)[C@@H](O)C3=C(C)[C@H](OC(=O)[C@@H](OC(=O)CCC(=O)NCCCOCCOCCOCCCNC(=O)CCC(NC(=O)c4ccc(NCc5cnc6c(=O)[nH]c(N)nc6n5)cc4)C(=O)O)[C@H](NC(=O)OC(C)(C)C)c4ccccc4)C[C@](O)([C@H](OC(=O)c4ccccc4)[C@@H]21)C3(C)C]

A solution of TFA Amino-PEG$_3$-folate (250 mg) in DMF (10 mL) was added with triethylamine (1 mL) and the mixture reaction was stirred for 20 minutes. Docetaxel-succinic acid-N-hydroxysuccinimide (made in a manner similar to that described in Thierry B, Kujawa P, Tkaczyk C, Winnik F M, Bilodeau L, Tabrizian M. Delivery platform for hydrophobic drugs: prodrug approach combined with self-assembled multilayers. J Am Chem Soc. 2005, 127, 1626-7) (300 mg) was added into the reaction mixture, and the reaction mixture was continued to stir for 15 hours. After 15 hours, precipitate was formed when acetone (150 mL) was added. Docetaxel-PEG$_3$-(folate)$_1$ was filtered and redissolved in a basic solution (pH 8). Precipitate of docetaxel-PEG$_3$-(folate)$_1$ was formed by adding a solution of diluted hydrochloric acid until pH around 3. The product was filtered, washed with water, and acetone, and air-dried, and collected to be 200 mg. The compound was characterized by $^1$H-NMR.

A solution of TFA.Amino-PEG$_3$-dendrimer-2 folates (250 mg) in DMF (10 mL) was added with triethylamine (1 mL) and the mixture reaction was stirred for 20 minutes. Docetaxel-succinic-N-hydroxysuccinimide (made in a manner similar to that described in Thierry B, Kujawa P, Tkaczyk C, Winnik F M, Bilodeau L, Tabrizian M. Delivery platform for hydrophobic drugs: prodrug approach combined with self-assembled multilayers. J Am Chem Soc. 2005, 127, 1626-7) (150 mg) was added into the reaction mixture, and the reaction mixture was continued to stir for 15 hours. After 15 hours, precipitate was formed when acetone (150 mL) was added. Docetaxel-dendrimer-(folate)$_2$ was filtered off and redissolved in a basic solution (pH 8). Precipitate of docetaxel-dendrimer-(folate)$_2$ was formed by adding a solution of diluted hydrochloric acid until pH around 3. The product was filtered, washed with water, and acetone, and air-dried, and collected to be 60 mg. The compound was characterized by $^1$H-NMR.

Example 31

Synthesis of docetaxel-dendrimer-(folate)$_2$

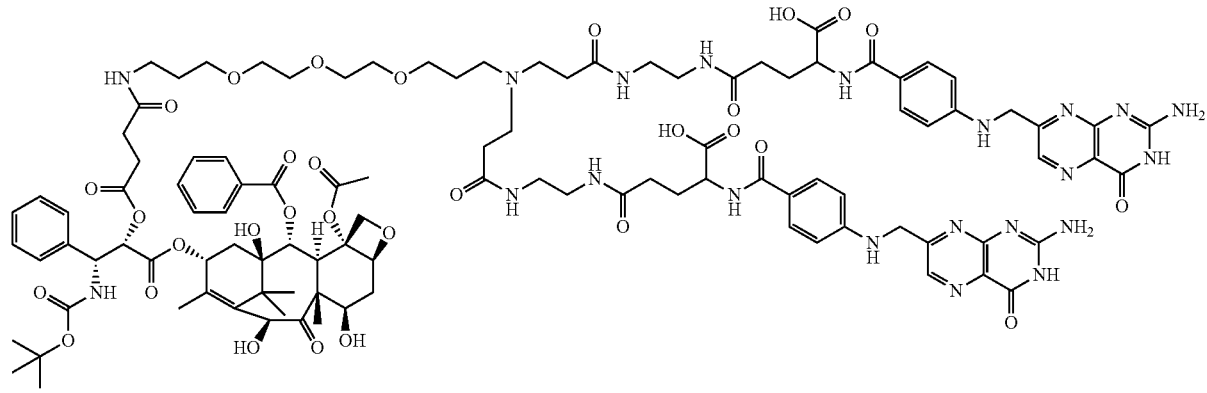 [SMILES: CC(=O)O[C@]12CO[C@H]1C[C@@H](O)[C@]1(C)C(=O)[C@@H](O)C3=C(C)[C@H](OC(=O)[C@@H](OC(=O)CCC(=O)NCCCOCCOCCOCCCN(CCC(=O)NCCNC(=O)CCC(NC(=O)c4ccc(NCc5cnc6c(=O)[nH]c(N)nc6n5)cc4)C(=O)O)CCC(=O)NCCNC(=O)CCC(NC(=O)c4ccc(NCc5cnc6c(=O)[nH]c(N)nc6n5)cc4)C(=O)O)[C@H](NC(=O)OC(C)(C)C)c4ccccc4)C[C@](O)([C@H](OC(=O)c4ccccc4)[C@@H]21)C3(C)C]

Example 32

Synthesis of docetaxel-dendrimer-(folate)$_4$

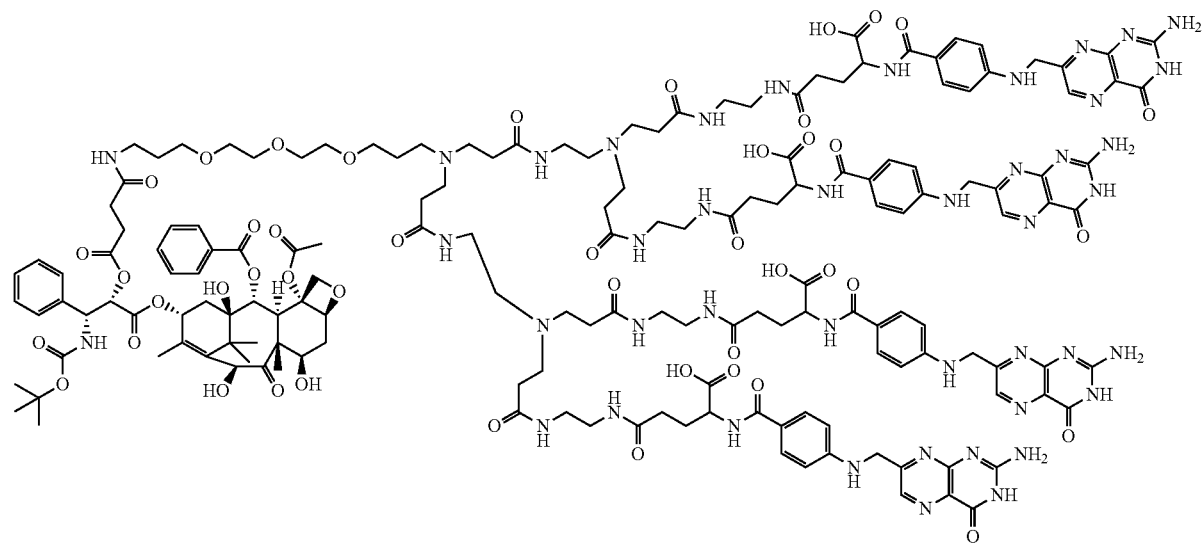 [SMILES: CC(=O)O[C@]12CO[C@H]1C[C@@H](O)[C@]1(C)C(=O)[C@@H](O)C3=C(C)[C@H](OC(=O)[C@@H](OC(=O)CCC(=O)NCCCOCCOCCOCCCN(CCC(=O)NCCN(CCC(=O)NCCNC(=O)CCC(NC(=O)c4ccc(NCc5cnc6c(=O)[nH]c(N)nc6n5)cc4)C(=O)O)CCC(=O)NCCNC(=O)CCC(NC(=O)c4ccc(NCc5cnc6c(=O)[nH]c(N)nc6n5)cc4)C(=O)O)CCC(=O)NCCN(CCC(=O)NCCNC(=O)CCC(NC(=O)c4ccc(NCc5cnc6c(=O)[nH]c(N)nc6n5)cc4)C(=O)O)CCC(=O)NCCNC(=O)CCC(NC(=O)c4ccc(NCc5cnc6c(=O)[nH]c(N)nc6n5)cc4)C(=O)O)[C@H](NC(=O)OC(C)(C)C)c4ccccc4)C[C@](O)([C@H](OC(=O)c4ccccc4)[C@@H]21)C3(C)C]

A solution of TFA.Amino-PEG$_3$-dendrimer-4 folates (310 mg) in DMF (10 mL) was added with triethylamine (1 mL) and the mixture reaction was stirred for 20 minutes. Docetaxel-succinic-N-hydroxysuccinimide (made in a manner similar to that described in Thierry B, Kujawa P, Tkaczyk C, Winnik F M, Bilodeau L, Tabrizian M. Delivery platform for hydrophobic drugs: prodrug approach combined with self-assembled multilayers. J Am Chem Soc. 2005, 127, 1626-7) (100 mg) was added into the reaction mixture, and the reaction mixture was continued to stir for 15 hours. After 15 hours, precipitate was formed when acetone (150 mL) was added. Docetaxel-dendrimer-(folate)$_4$ was filtered and redissolved in a basic solution (pH 8). Precipitate of docetaxel-dendrimer-(folate)$_4$ was formed by adding a solution of diluted hydrochloric acid until pH around 3. The product was filtered, washed with water, and acetone, and air-dried, and collected to be 80 mg. The compound was characterized by 1H-NMR.

Example 33

Synthesis of docetaxel-dendrimer-(folate)$_4$

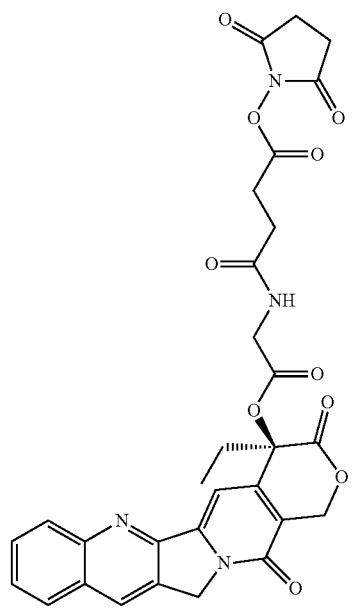

CPT-gly-succinic acid-NHS

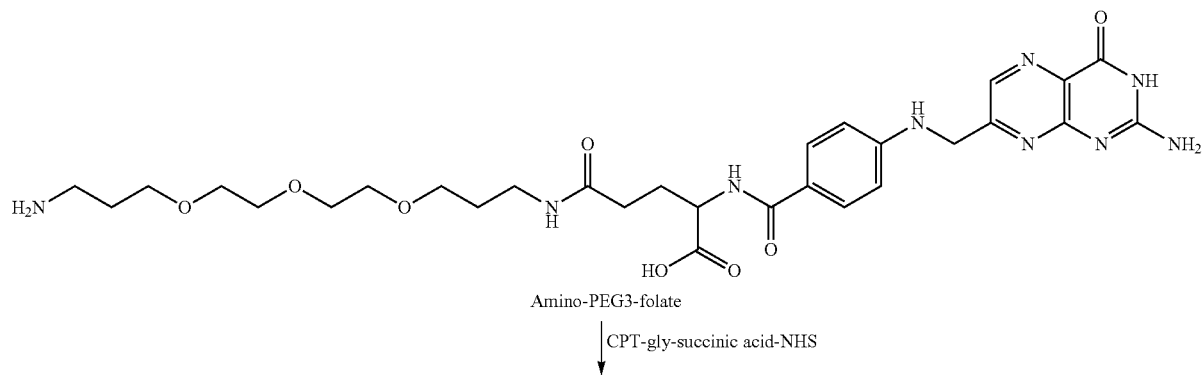

Amino-PEG3-folate

| CPT-gly-succinic acid-NHS

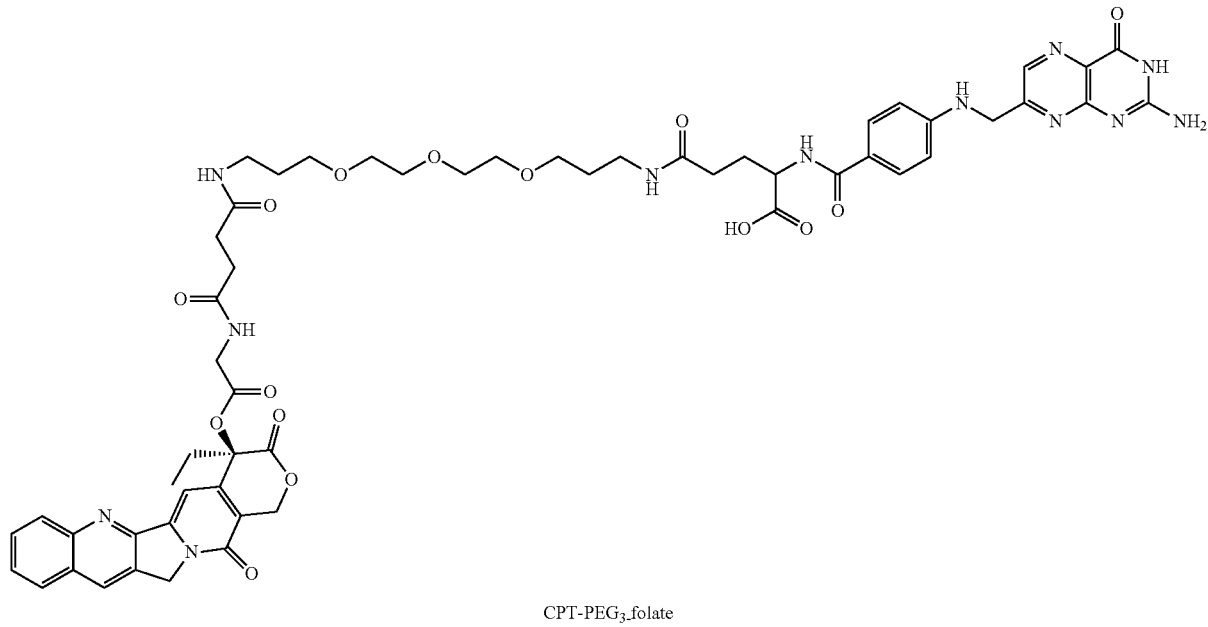

CPT-PEG$_3$-folate

A solution of TFA.Amino-PEG$_3$-folate (60 mg) in DMF (10 mL) was added with triethylamine (1 mL) and the mixture reaction was stirred for 20 minutes. CPT-gly-succinic acid-NHS (made in a manner similar to that described in Walsh M D, Hanna S K, Sen J, Rawal S, Cabral C B, Yurkovetskiy A V, Fram R J, Lowinger T B, Zamboni W C. Pharmacokinetics and antitumor efficacy of XMT-1001, a novel, polymeric topoisomerase I inhibitor, in mice bearing HT-29 human colon carcinoma xenografts. Clin Cancer Res. 2012 May 1; 18(9):2591-602) (30 mg) was added into the reaction mixture, and the reaction mixture was continued to stir for 15 hours. After 15 hours, precipitate was formed when acetone (150 mL) was added. Camptothecin-PEG$_3$-(folate)$_1$ was filtered off and redissolved in a basic solution (pH 8). Precipitate of camptothecin-PEG$_3$-(folate)$_1$ was formed by adding a solution of diluted hydrochloric acid until pH around 3. The product was filtered, washed with water, and acetone, and air-dried, and collected to be 30 mg. The compound was characterized by $^1$H-NMR.

Example 34

Synthesis of camptothecin-dendrimer-(folate)$_2$

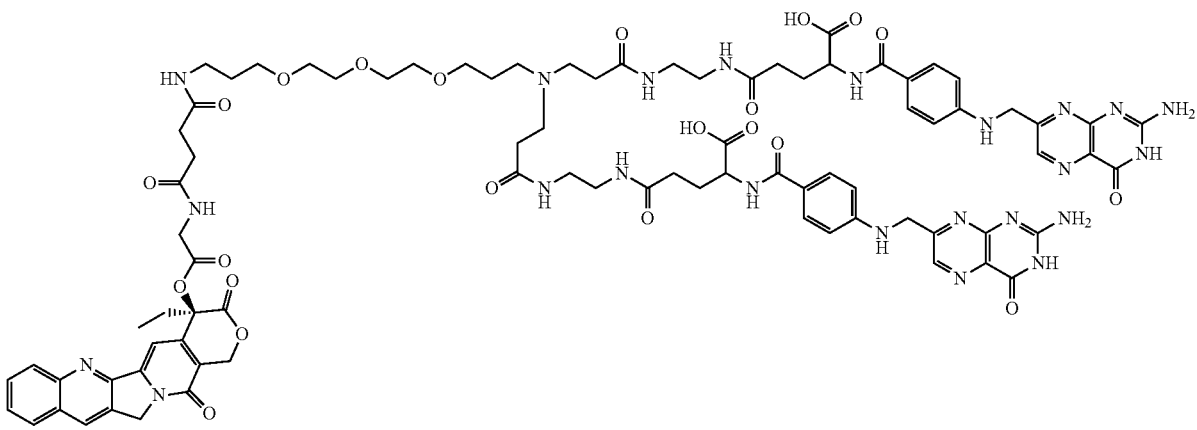 [SMILES: CC[C@]1(OC(=O)CNC(=O)CCC(=O)NCCCOCCOCCOCCCN(CCC(=O)NCCNC(=O)CCC(NC(=O)c2ccc(NCc3cnc4c(=O)[nH]c(N)nc4n3)cc2)C(=O)O)CCC(=O)NCCNC(=O)CCC(NC(=O)c2ccc(NCc3cnc4c(=O)[nH]c(N)nc4n3)cc2)C(=O)O)C(=O)OCc2c1cc1n(c2=O)Cc2cc3ccccc3nc2-1]

A solution of TFA Amino-dendrimer-(folate)₂ (90 mg) in DMF (10 mL) was added with triethylamine (1 mL) and the mixture reaction was stirred for 20 minutes. CPT-gly-succinic acid-NHS (made in a manner similar to that described in Walsh M D, Hanna S K, Sen J, Rawal S, Cabral C B, Yurkovetskiy A V, Fram R J, Lowinger T B, Zamboni W C. Pharmacokinetics and antitumor efficacy of XMT-1001, a novel, polymeric topoisomerase I inhibitor, in mice bearing HT-29 human colon carcinoma xenografts. Clin Cancer Res. 2012 May 1; 18(9):2591-602) (30 mg) was added into the reaction mixture, and the reaction mixture was continued to stir for 15 hours. After 15 hours, precipitate was formed when acetone (150 mL) was added. Camptothecin-dendrimer-(folate)₂ was filtered and redissolved in a basic solution (pH 8). Precipitate of camptothecin-dendrimer-(folate)₂ was formed by adding a solution of diluted hydrochloric acid until pH around 3. The product was filtered, washed with water, and acetone, and air-dried, and collected to be 40 mg. The compound was characterized by ¹H-NMR.

Example 35

Synthesis of chloramphenicol-succinic acid-(folate)₁

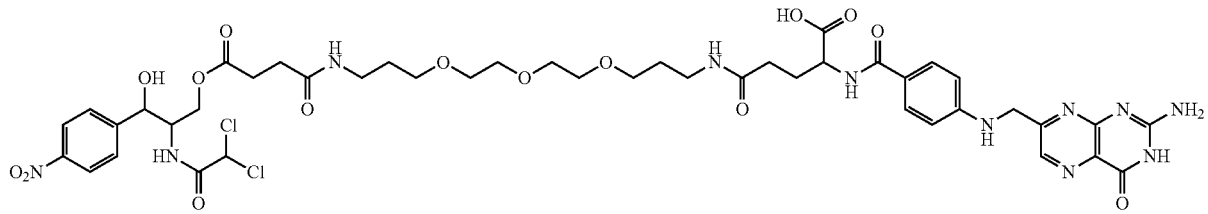 [SMILES: Nc1nc2nc(CNc3ccc(C(=O)NC(CCC(=O)NCCCOCCOCCOCCCNC(=O)CCC(=O)OCC(NC(=O)C(Cl)Cl)C(O)c4ccc([N+](=O)[O-])cc4)C(=O)O)cc3)cnc2c(=O)[nH]1]

A solution of TFA Amino-PEG₃-folate (400 mg) in DMF (10 mL) was added with triethylamine (1 mL) and the mixture reaction was stirred for 20 minutes. Chloramphenicol-succinic acid-N-hydroxysuccinimide (400 mg) was added into the reaction mixture, and the reaction mixture was continued to stir for 15 hours. After 15 hours, precipitate was formed when acetone (150 mL) was added. Chloramphenicol-succinic acid-(folate)₁ was filtered off and redissolved in a basic solution (pH 8). Precipitate of chloramphenicol-succinic acid-(folate)₁ was formed by adding a solution of diluted hydrochloric acid until pH around 3. The product was filtered, washed with water, and acetone, and air-dried, and collected to be 290 mg. The compound was characterized by ¹H-NMR.

Example 36

Synthesis of chloramphenicol-glutaric acid-(folate)₁

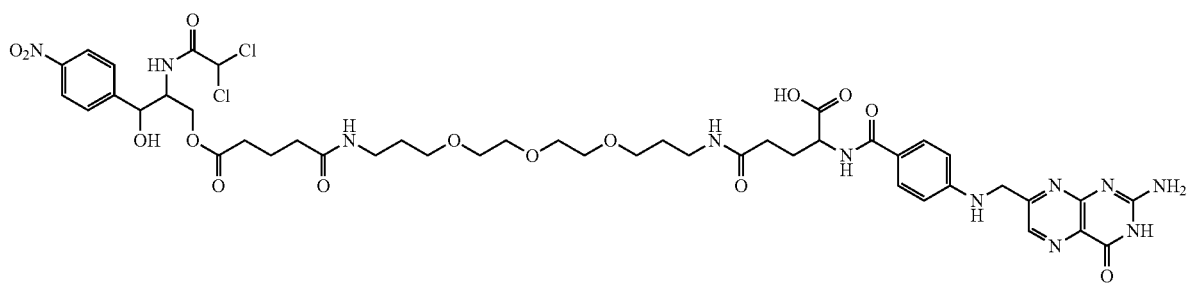 [SMILES: Nc1nc2nc(CNc3ccc(C(=O)NC(CCC(=O)NCCCOCCOCCOCCCNC(=O)CCCC(=O)OCC(NC(=O)C(Cl)Cl)C(O)c4ccc([N+](=O)[O-])cc4)C(=O)O)cc3)cnc2c(=O)[nH]1]

A solution of TFA Amino-PEG$_3$-folate (400 mg) in DMF (10 mL) was added with triethylamine (1 mL) and the mixture reaction was stirred for 20 minutes. Chloramphenicol-glutaric acid-N-hydroxysuccinimide (400 mg) was added into the reaction mixture, and the reaction mixture was continued to stir for 15 hours. After 15 hours, precipitate was formed when acetone (150 mL) was added. Chloramphenicol-glutaric acid-(folate)$_1$ was filtered off and redissolved in a basic solution (pH 8). Precipitate of chloramphenicol-glutaric acid-(folate)$_1$ was formed by adding a solution of diluted hydrochloric acid until pH around 3. The product was filtered, washed with water, and acetone, and air-dried, and collected to be 330 mg. The compound was characterized by $^1$H-NMR.

Example 37

Synthesis of chloramphenicol-dendrimer-(folate)$_2$

A solution of TFA Amino-dendrimer-(folate)$_2$ (500 mg) in DMF (10 mL) was added with triethylamine (1 mL) and the mixture reaction was stirred for 20 minutes. Chloramphenicol-glutaric acid-N-hydroxysuccinimide (250 mg) was added into the reaction mixture, and the reaction mixture was continued to stir for 15 hours. After 15 hours, precipitate was formed when acetone (150 mL) was added chloramphenicol-dendrimer-(folate)$_2$ was filtered off and redissolved in a basic solution (pH 8). Precipitate of chloramphenicol-dendrimer-(folate)$_2$ was formed by adding a solution of diluted hydrochloric acid until pH around 3. The product was filtered, washed with water, and acetone, and air-dried, and collected to be 200 mg. The compound was characterized by $^1$H-NMR.

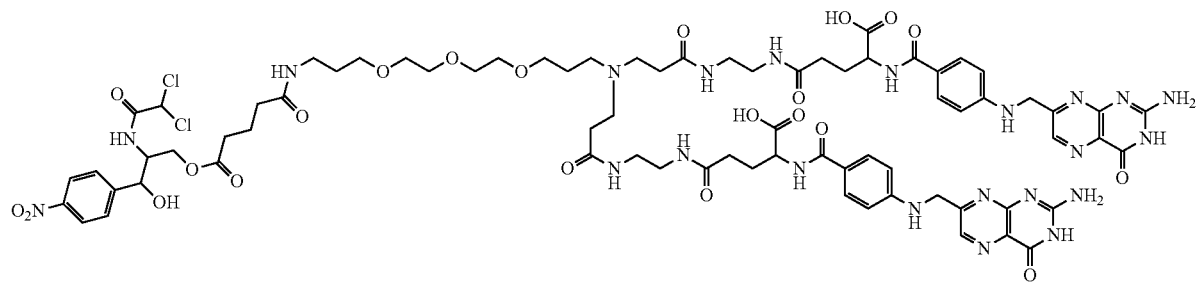 [SMILES: Nc1nc2nc(CNc3ccc(C(=O)NC(CCC(=O)NCCNC(=O)CCN(CCCOCCOCCOCCCNC(=O)CCCC(=O)OCC(NC(=O)C(Cl)Cl)C(O)c4ccc([N+](=O)[O-])cc4)CCC(=O)NCCNC(=O)CCC(NC(=O)c4ccc(NCc5cnc6c(=O)[nH]c(N)nc6n5)cc4)C(=O)O)C(=O)O)cc3)cnc2c(=O)[nH]1]

Example 38

Synthesis of chloramphenicol-dendrimer-(folate)$_4$

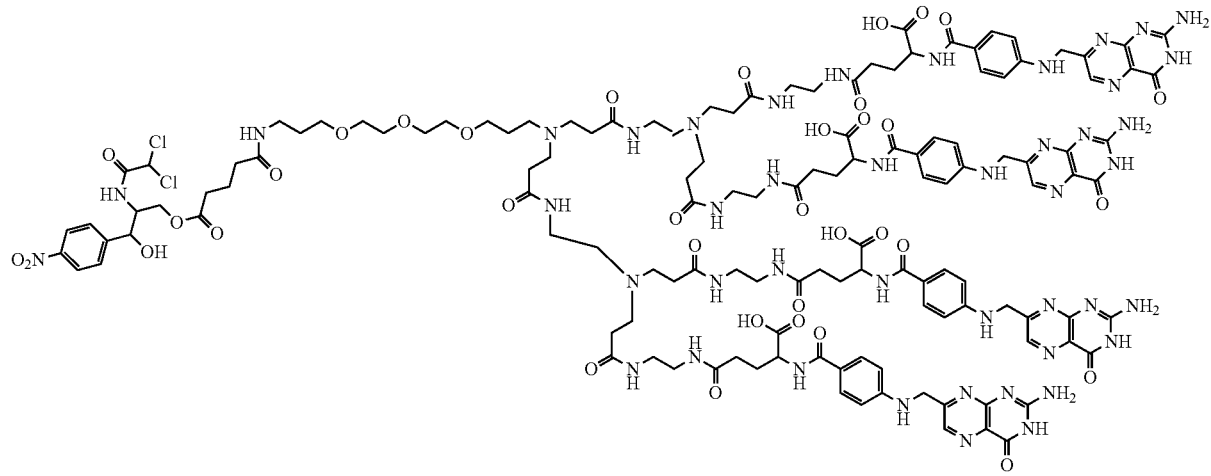

A solution of TFA Amino-dendrimer-(folate)$_4$ (500 mg) in DMF (10 mL) was added with triethylamine (1 mL) and the mixture reaction was stirred for 20 minutes. Chloramphenicol-glutaric acid-N-hydroxysuccinimide (130 mg) was added into the reaction mixture, and the reaction mixture was continued to stir for 15 hours. After 15 hours, precipitate was formed when acetone (150 mL) was added chloramphenicol-dendrimer-(folate)$_4$ was filtered off and redissolved in a basic solution (pH 8). Precipitate of chloramphenicol-dendrimer-(folate)$_4$ was formed by adding a solution of diluted hydrochloric acid until pH around 3. The product was filtered, washed with water, and acetone, and air-dried, and collected to be 300 mg. The compound was characterized by 1H-NMR.

Example 39

Synthesis of TFA.ethylenediamine-PEG$_3$-folate

A solution of TFA.Amino-PEG$_3$-folate (1000 mg) in DMF (10 mL) was added with triethylamine (2 mL) and the mixture reaction was stirred for 20 minutes. Di-Boc-ethylenediamine-NHS (560 mg) was added into the reaction mixture, and the reaction mixture was continued to stir for 15 hours. After 15 hours, precipitate was formed when acetone (150 mL) was added. Di-Boc-Ethylenediamine-PEG$_3$-folate was filtered off and redissolved in a basic solution (pH 8). Precipitate of Di-Boc-Ethylenediamine-PEG$_3$-folate was formed by adding a solution of diluted hydrochloric acid until pH around 3. Di-Boc-Ethylenediamine-PEG$_3$-folate was filtered, washed with water, and acetone, and air-dried, and collected to be 850 mg. Di-Boc-Ethylenediamine-PEG$_3$-folate was added with dichloromethane (7 mL) and TFA (7 mL) and the reaction mixture was stirred for 3 hours at ambient temperature. TFA-Ethyl-

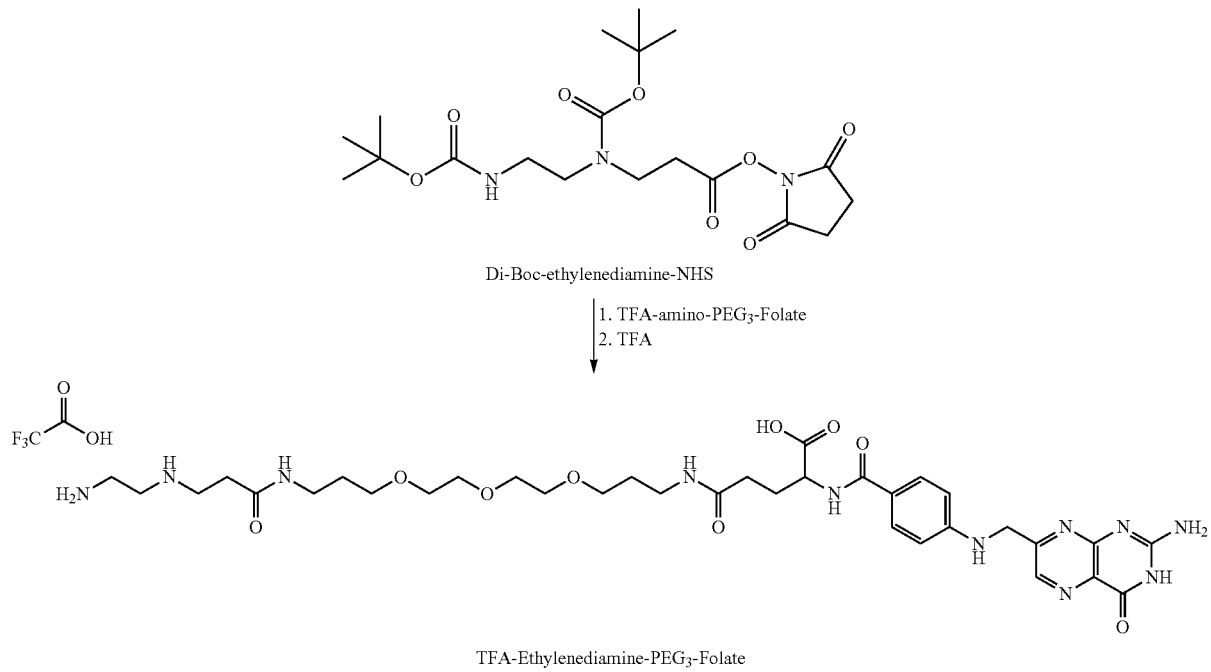

Di-Boc-ethylenediamine-NHS

1. TFA-amino-PEG$_3$-Folate
2. TFA

TFA-Ethylenediamine-PEG$_3$-Folate enediamine-PEG$_3$-folate (600 mg) was obtained. The compound was characterized by $^1$H-NMR.

Example 40

Synthesis of cisplatin-PEG$_3$-folate

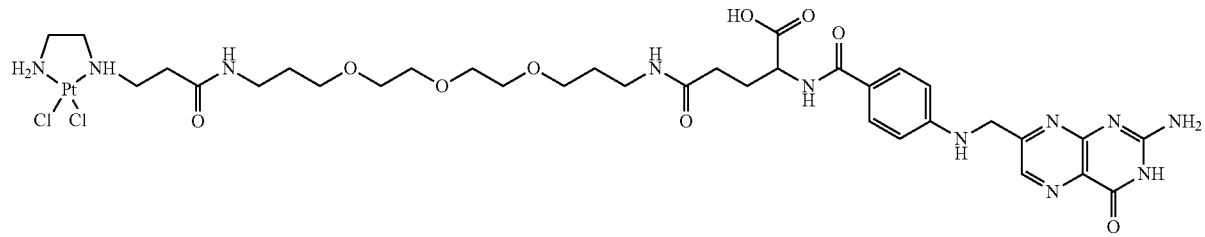

TFA-Ethylenediamine-PEG$_3$-folate (320 mg) and Pt(DMSO)$_2$Cl$_2$ (120 mg) was stirred in 10 mL solution of methanol:water mixture (1:1). A diluted solution of sodium hydroxide was added to adjust the pH the reaction mixture to pH>10. The mixture was stirred for 5 hours. Acetone was added to induce precipitation of cisplatin-PEG$_3$-folate. The product was filtered and washed with acetone and collected (200 mg). The compound was characterized by $^1$H-NMR.

Example 41

Synthesis of cisplatin-PEG$_3$-ketone

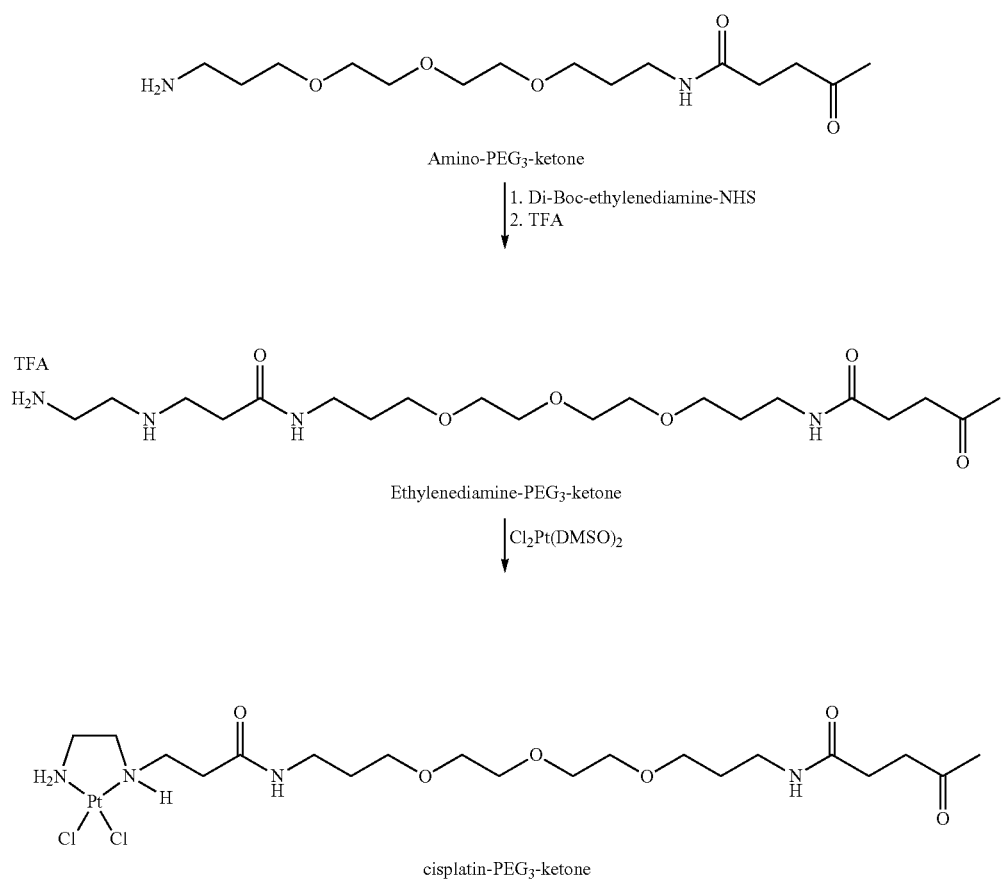

A solution of di-Boc-ethylenediamine-NHS (5 grams) and TFA Amino-PEG$_3$-ketone (6 grams) in dichloromethane (DCM, 10 mL) was added with triethylamine (8 mL). DCM (20 mL) was added. The mixture reaction was stirred for 15 hours. Water (50 mL) was added, and a diluted HCl solution was added to adjust pH to 3. Organic product was extracted in DCM, and the solvent was removed by rotary evaporation. A 50% TFA in DCM (20 mL) was added to the organic product. The reaction was stirred for 5 hours. The volatiles were removed and TFA. Ethylenediamine-PEG$_3$-ketone was obtained (2 grams).

TFA.Ethylenediamine-PEG$_3$-ketone (350 mg) and Pt(DMSO)$_2$Cl$_2$ (200 mg) was stirred in a mixture of methanol:water (1:1) (10 mL). A diluted solution of sodium hydroxide was added until pH>10. The reaction was stirred for 5 hours. Acetone (150 mL) was added to induce precipitation and solid cisplatin-PEG$_3$-ketone was filtered, washed with acetone, dried, and collected (120 mg). The compound was characterized by $^1$H-NMR.

Example 42

Synthesis of cisplatin-hydrazone-dendrimer-(folate)$_2$

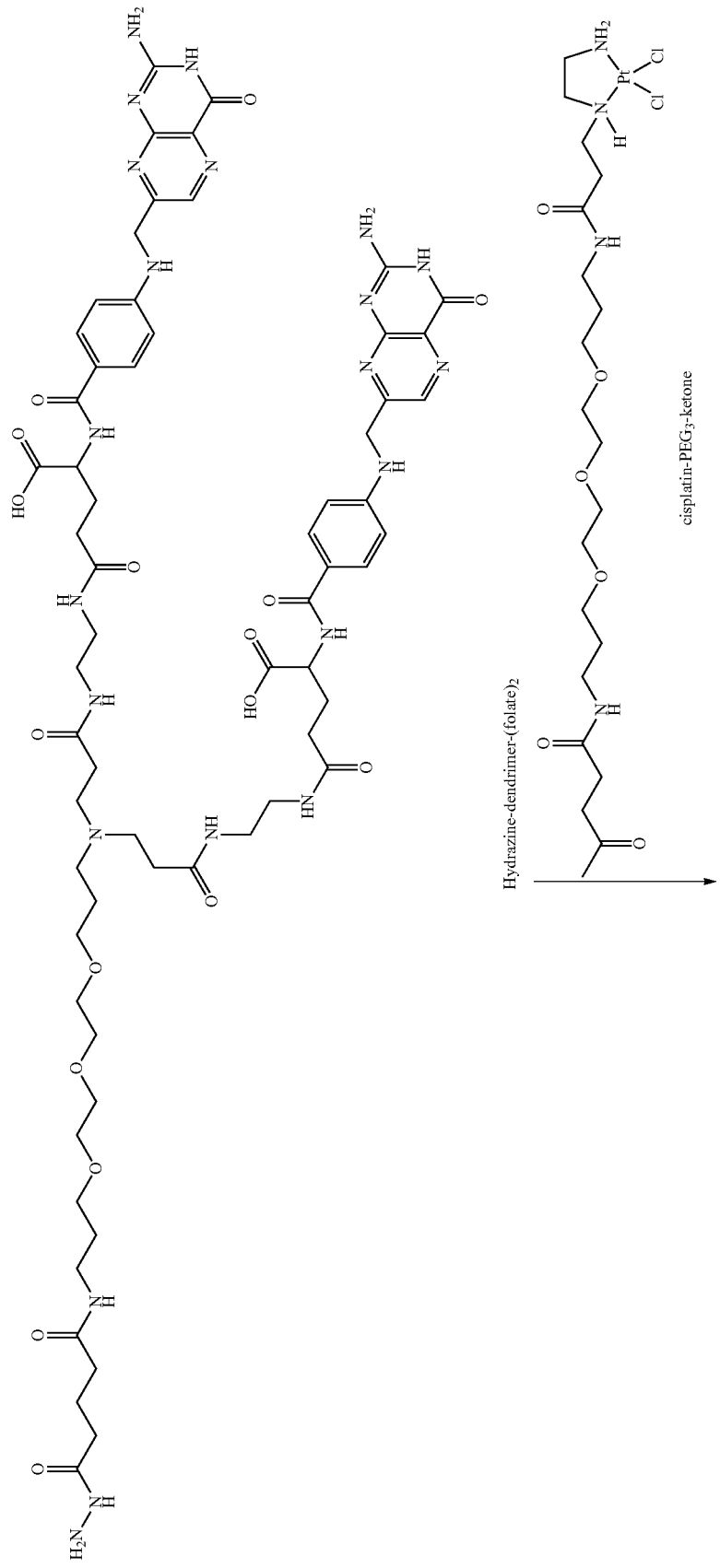

-continued
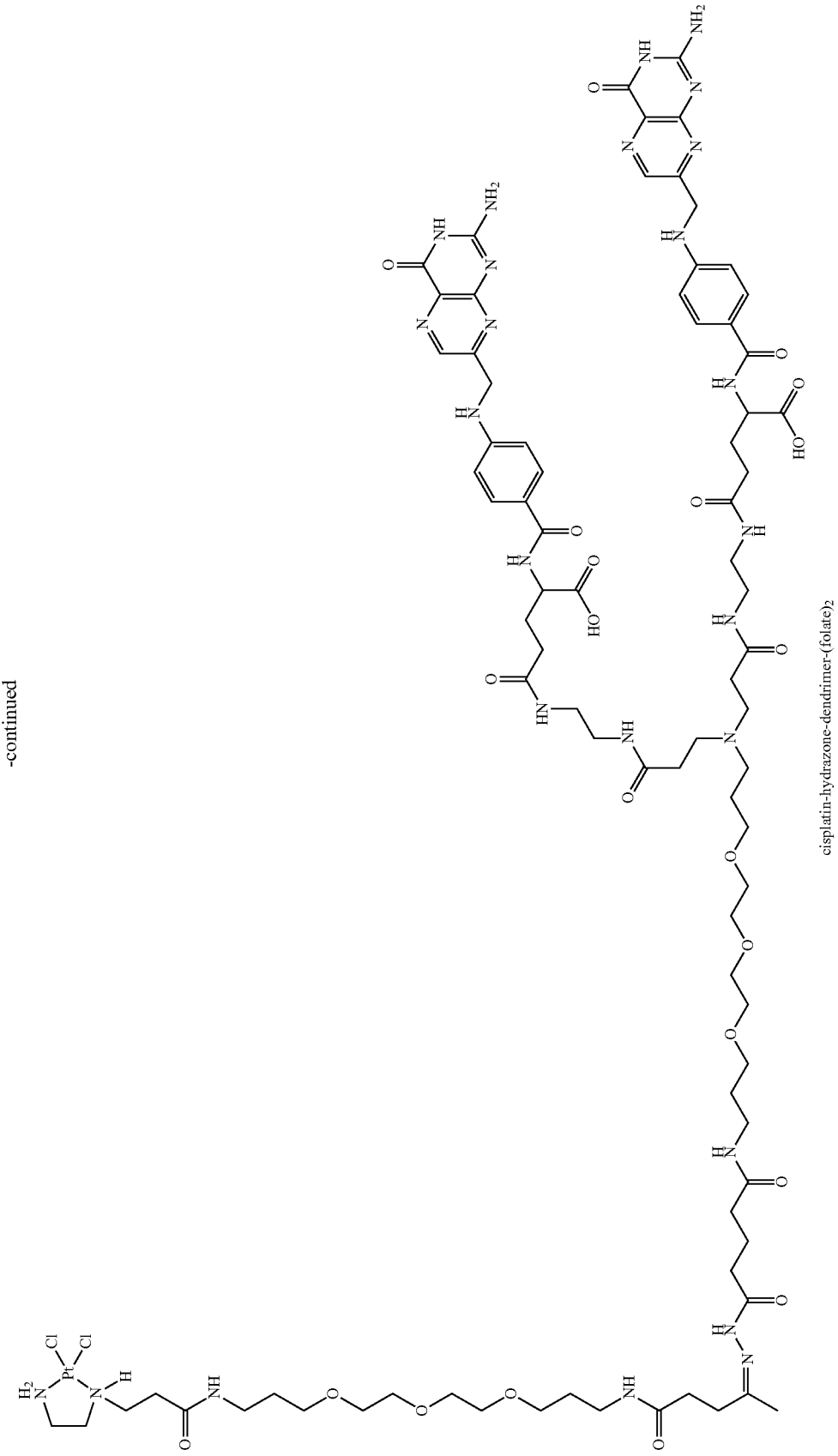
cisplatin-hydrazone-dendrimer-(folate)₂

A mixture of cisplatin-PEG$_3$-ketone (50 mg) and hydrazine-dendrimer-(folate)$_2$ (130 mg) was stirred in methanol. A drop of TFA was added and the mixture was stirred for 15 hours. Cisplatin-hydrazine-dendrimer-(folate)$_2$ was formed as solid, filtered, washed, dried, and collected (40 mg). The compound was characterized by 1H-NMR.

Example 43

Synthesis of cisplatin-hydrazone-dendrimer-(folate)$_4$

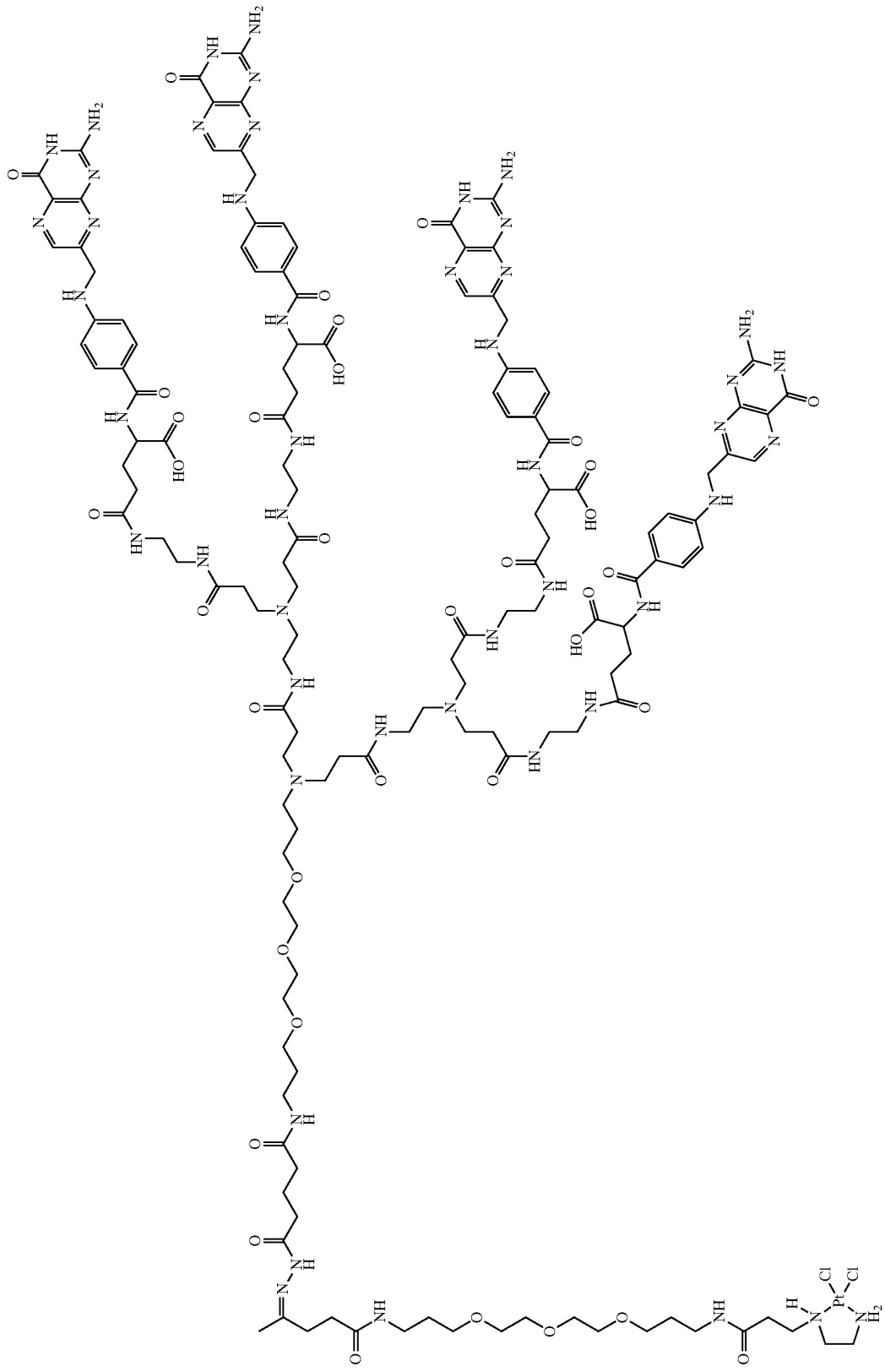
cisplatin-hydrazone-dendrimer-(folate)₄

A mixture of cisplatin-PEG$_3$-ketone (50 mg) and hydrazine-dendrimer-(folate)$_4$ (250 mg) was stirred in methanol. A drop of TFA was added and the mixture was stirred for 15 hours. Cisplatin-hydrazine-dendrimer-(folate)$_4$ was formed as solid, filtered, washed, dried, and collected (70 mg). The compound was characterized by 1H-NMR.
Example 44
Synthesis of Gd-chelate-dendrimer-(folate)$_2$
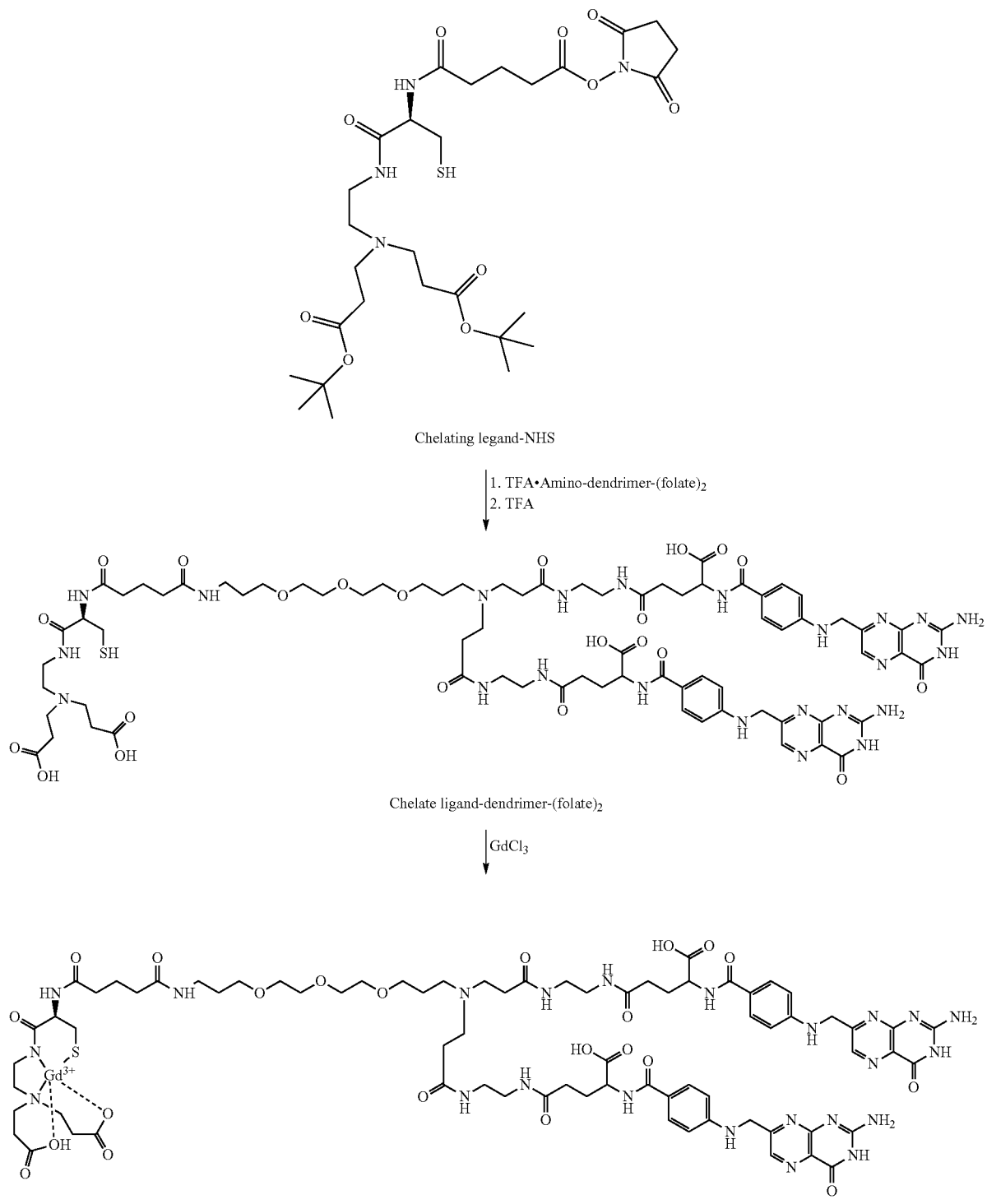

A solution of TFA Amino-dendrimer-(folate)$_2$ (650 mg) in DMF (10 mL) was added with triethylamine (2 mL) and the mixture reaction was stirred for 20 minutes. Chelating ligand-NHS (240 mg) was added into the reaction mixture, and the reaction mixture was continued to stir for 15 hours. After 15 hours, precipitate was formed when acetone (150 mL) was added. The compound was filtered, washed with acetone, air-dried, and collected to be 380 mg. The compound was characterized by $^1$H-NMR. The compound was further treated with TFA (20 mL) for 24 hours to become chelating ligand-dendrimer-(folate)$_2$. Chelating ligand-dendrimer-(folate)$_2$ (320 mg) was suspended in water (10 mL) and a diluted sodium hydroxide solution was added to adjust the pH to above 10 (checked by pH paper). GdCl$_3$ (40 mg) was added and stirred for 15 hours. A diluted solution of HCl was added to adjust pH to 3-4, precipitate of Gd-chelate-dendrimer-(folate)$_2$ was formed, filtered, washed with water and acetone, and collected (80 mg). Gd-chelate-dendrimer-(folate)$_2$ (10 mg) was soluble in an aqueous solution (5 mL) with pH greater than 7.

Example 45

Figure 9:
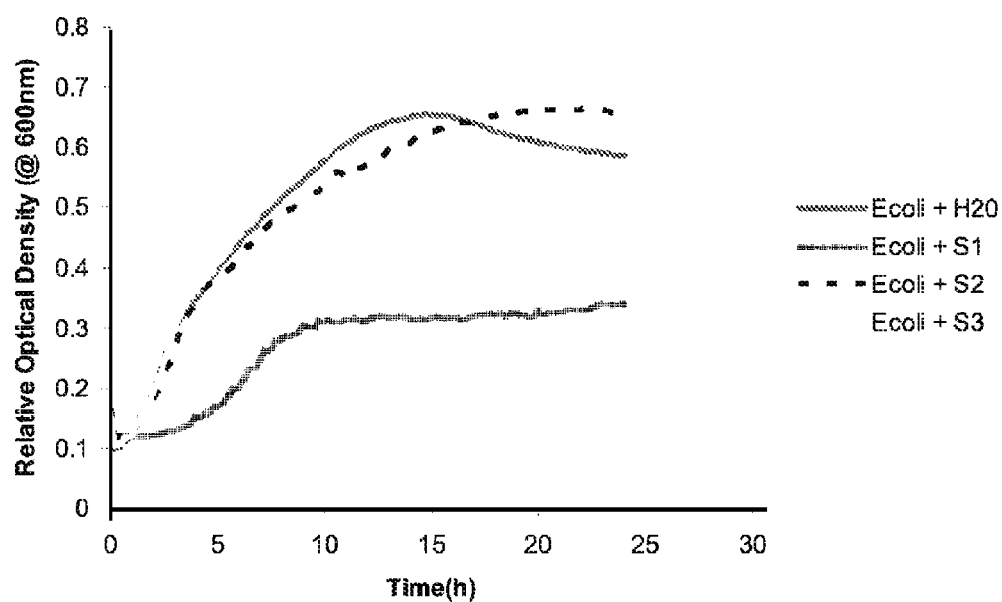
FIG. 9 is a plot showing the growth inhibition of E. coli bacteria by a drug conjugate of chloramphenicol-succinic acid-dendrimer-(folate)$_4$. The results show that the inhibition is dose dependent response.
Figure 10:
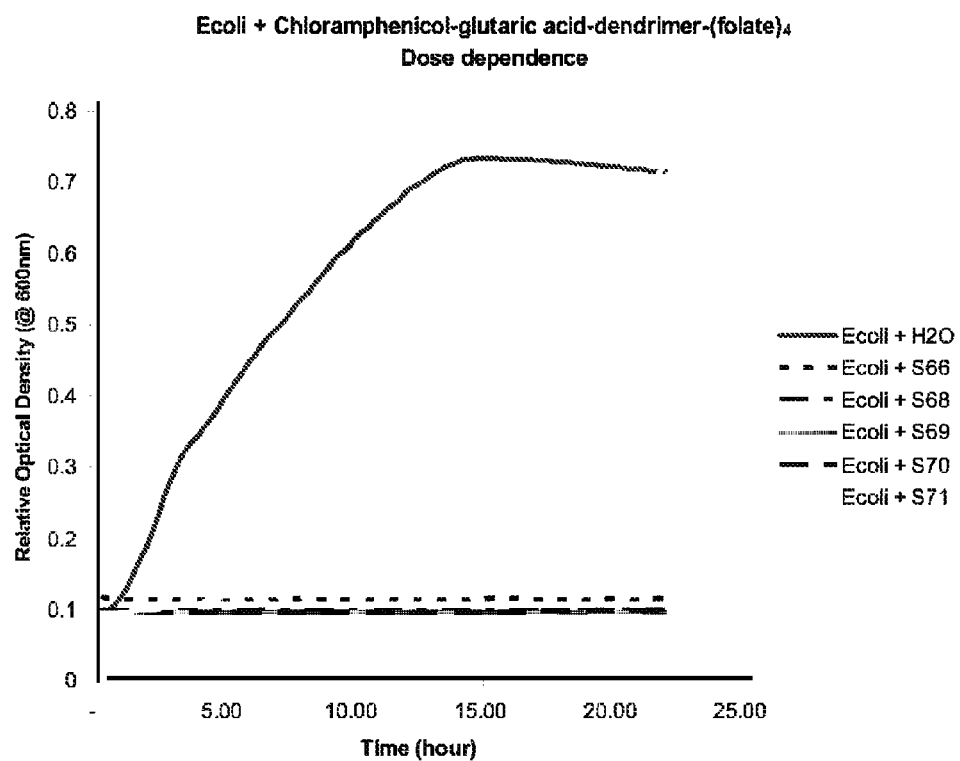
FIG. 10 is a plot showing the growth inhibition of E coli bacteria by a drug conjugate of chloramphenicol-glutaric acid-dendrimer-(folate)$_4$. The results show that the inhibition is dose dependent response and the drug conjugate with 4 folate molecules can inhibit the bacterial growth at very low dose.

One colony of *E. coli* was grown overnight in LB broth. Then the bacteria were diluted 1:50 with LB broth and then cultured for 2 h. Then a sample of 50 ul of the culture was mixed with 50 ul LB broth and 50 ul of different solutions at a different concentration. The mixture was placed on a plate reader, with sampling every 15 minutes for 22 h under incubation at 37° C. The experiment was performed in triplicate and the average of the data was plotted (FIGS. 9-10).

Example 46

Figure 11:
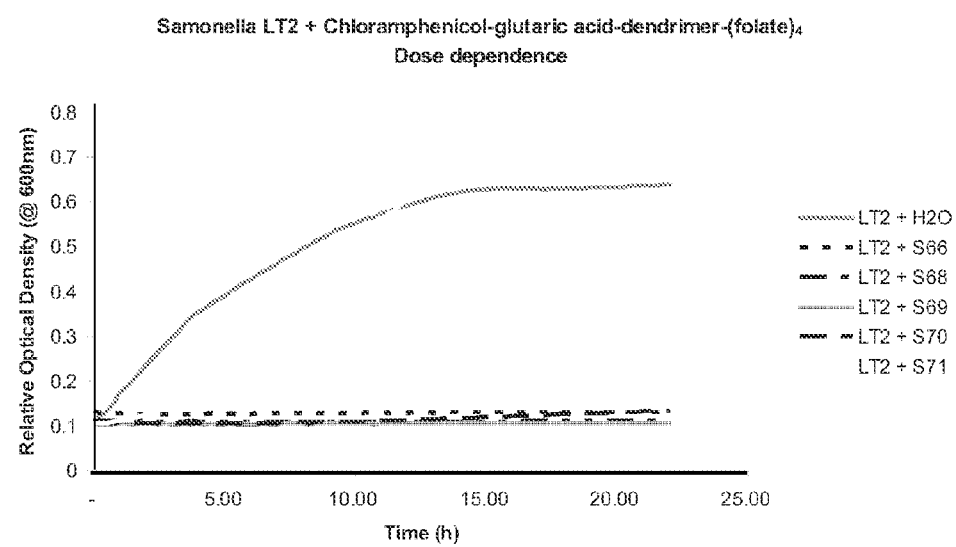
FIG. 11 is a plot showing the growth inhibition of Samonella LT2 bacteria by a drug conjugate of chloramphenicol-glutaric acid-dendrimer-(folate)$_4$. The results show that the inhibition is dose dependent response and the drug conjugate with 4 folate molecules can inhibit the bacterial growth at very low dose.

One colony of *Salmonella* LT2 was grown overnight in LB broth. Then the bacteria were diluted 1:10 with LB broth and then cultured for 2 h. Then a sample of 50 ul of the culture was mixed with 50 ul LB broth and 50 ul of different solutions at a different concentration. The mixture was placed on a plate reader, with sampling every 15 minutes for 22 h under incubation at 37° C. The experiment was performed in triplicate and the average of the data was plotted (FIG. 11).

It will be understood by those of skill in the art that numerous and various modifications can be made without departing from the spirit of the present invention. Therefore, it should be clearly understood that the forms of the present invention are illustrative only and not intended to limit the scope of the present invention.

What is claimed is:

1. An asymmetrical dendritic compound represented by the Formula (I):

$$R^1—X^1—NH-L-Gn-(NH—X^2—R^2)_m \quad (I)$$

wherein:

Gn is a dendritic PAMAM (poly(amidoamine)) group, having a core group and a shell group, for which n is zero or an integer in the range of 1 to 3 that specifies the generation of the dendritic PAMAM group;

$R^1$—$X^1$—NH-L is a group attached to the core group, wherein $R^1$ is selected from H, NH$_2$NH, CO$_2$C(CH$_3$)$_3$, a maleimide group, a targeting ligand, a drug, and an imaging agent; $X^1$ is absent or selected from C(=O) (CH$_2$)$_a$C(=O), C$_{1-4}$ alkylene and C$_{1-8}$ alkyleneoxide; and L is absent or selected from C$_{1-4}$ alkylene and C$_{1-8}$ alkyleneoxide;

(NH—$X^2$—$R^2$)$_m$ is a terminal group attached to the shell group, wherein m is 2, 4, 8 or 16 and specifies the number of the attached NH—$X^2$—$R^2$ terminal groups; each $X^2$ is independently absent or a linker selected from C$_{1-4}$ alkylene, succinimidyl, C$_{1-8}$ alkyleneoxide, C(=O)(CH$_2$)$_a$C(=O), C(=O)(CH$_2$)$_a$C(=O)—NH—C$_{1-4}$alkylene-NH, and C(=O)(CH$_2$)$_a$C(=O)—NH—C$_{1-8}$alkyleneoxide-NH; and each $R^2$ is independently selected from H, hydroxyl, a maleimide group, a succinimide group, a targeting ligand, a drug, and an imaging agent;

each a is independently an integer in the range of 1 to 4; and each $R^2$ is different from $R^1$.

2. The asymmetrical dendritic compound of claim 1, represented by the Formula (Ia), (Ib), (Ic) or (Id):

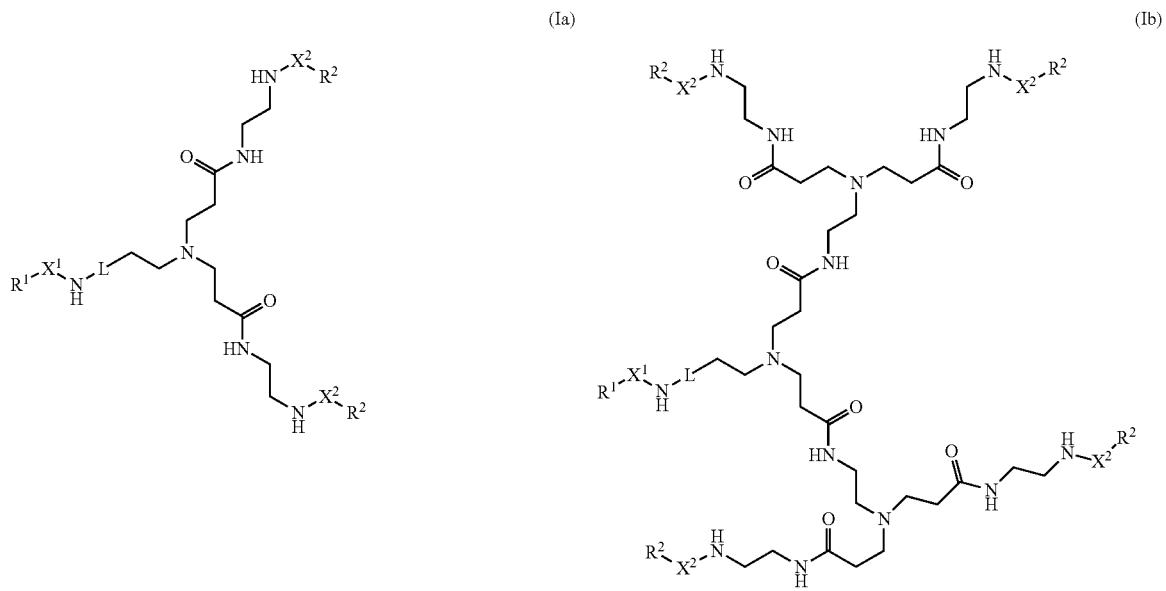

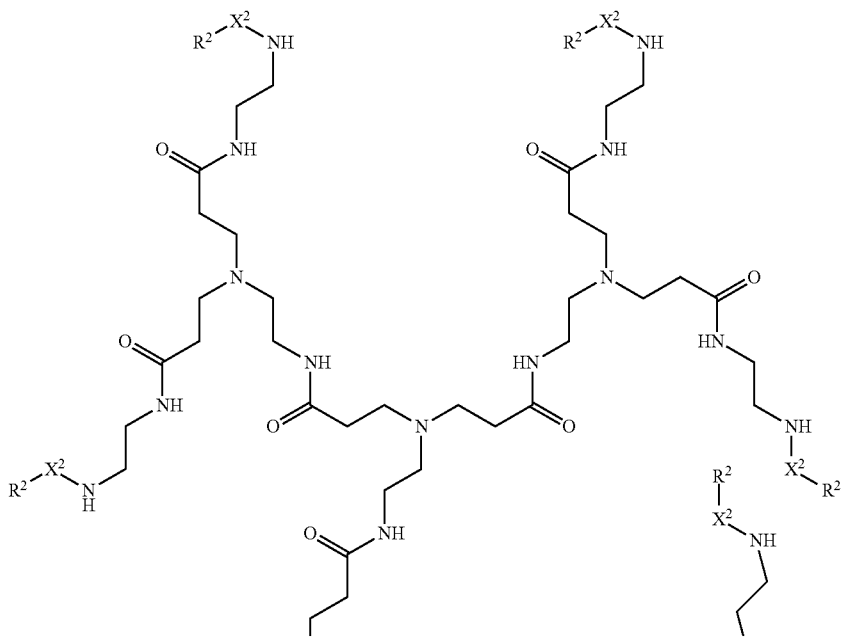
(Ic)
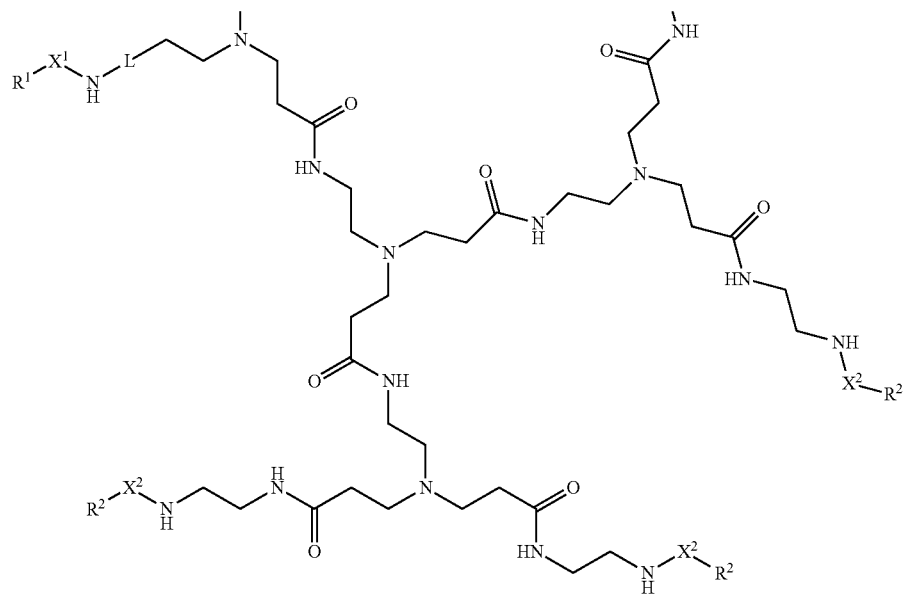

-continued
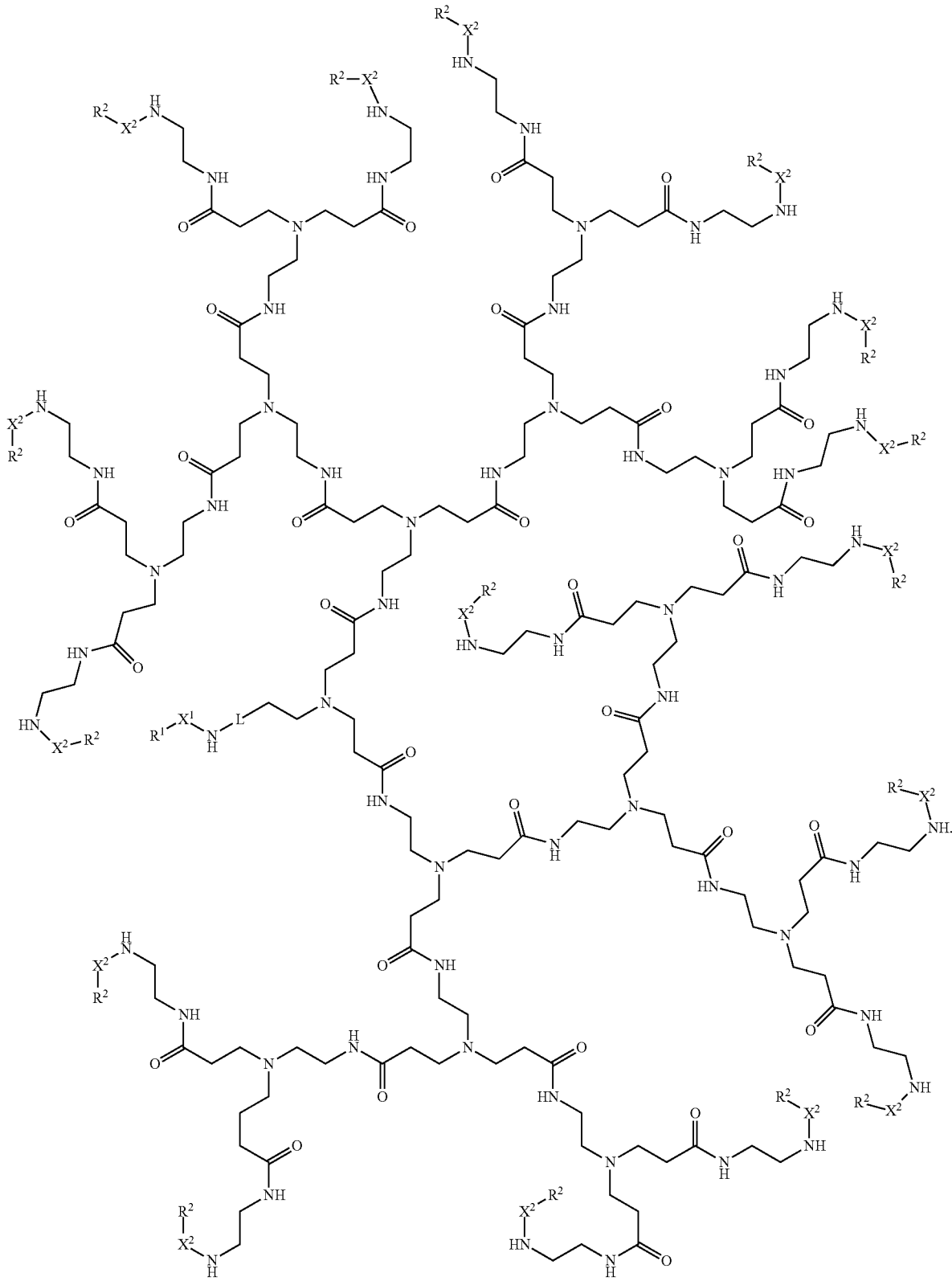
(Id)

3. The asymmetrical dendritic compound of claim 1, wherein $R^1$ is selected from the group consisting of H, $CO_2C(CH_3)_3$, and maleimide.

4. The asymmetrical dendritic compound of claim 1, wherein $R^2$ comprises a targeting ligand.

5. The asymmetrical dendritic compound of claim 1, wherein the targeting ligand is selected from the group consisting of folic acid, mannose, anisamide, RGD peptide, NGR peptide, galactosamine, antibody, antibody fragment, and protein.

6. The asymmetrical dendritic compound of claim 1, wherein $R^2$ comprises an imaging agent.

7. The asymmetrical dendritic compound of claim 1, wherein the imaging agent is selected from the group consisting of a Gadolinium (III)-chelate, a Technetium (99m)-chelate, a Gallium-chelate, and a Thallium-chelate.

8. The asymmetrical dendritic compound of claim 1, wherein the imaging agent is selected from the group consisting of $^{64}Cu$ diacetyl-bis($N^4$-methylthiosemicarbazone), $^{18}F$-fluorodeoxyglucose, 3'-deoxy-3'-($^{18}F$)fluorothymidine, and $^{18}F$-fluoromisonidazole.

9. The asymmetrical dendritic compound of claim 1, wherein $R^2$ comprises a drug.

10. A therapeutic agent represented by the Formula (I):

$$R^1—X^1—NH-L-Gn-(NH—X^2—R^2)_m \quad (I)$$

wherein:

Gn is a dendritic PAMAM group, having a core group and a shell group, for which n is zero or an integer in the range of 1 to 3 that specifies the generation of the dendritic PAMAM group;

$R^1$—$X^1$—NH-L is a group attached to the core group, wherein $R^1$ is selected from a targeting ligand, an anticancer drug, and an imaging agent; $X^1$ is absent or selected from $C(=O)(CH_2)_aC(=O)$, $C_{1-4}$ alkylene and $C_{1-8}$ alkyleneoxide; and L is absent or selected from $C_{1-4}$ alkylene and $C_{1-4}$ alkyleneoxide;

$(NH—X^2—R^2)_m$ is a terminal group attached to the shell group, wherein m is 2, 4, 8 or 16 and specifies the number of the attached $NH—X^2—R^2$ terminal groups; each $X^2$ is independently absent or a linker selected from $C_{1-4}$ alkylene, succinimidyl, $C_{1-8}$ alkyleneoxide, $C(=O)(CH_2)_aC(=O)$, $C(=O)(CH_2)_aC(=O)—NH—C_{1-4}$alkylene-NH, and $C(=O)(CH_2)_aC(=O)—NH—C_{1-8}$alkyleneoxide-NH; and each $R^2$ is independently selected from a targeting ligand, an anticancer drug, and an imaging agent;

each a is independently an integer in the range of 1 to 4; and each $R^2$ is different from $R^1$.

11. The therapeutic agent of claim 10, wherein one of $R^1$ and $R^2$ comprises a targeting ligand and the other of $R^1$ and $R^2$ comprises an anticancer drug or an imaging agent.

12. The therapeutic agent of claim 10, wherein $R^1$ comprises an anticancer drug.

13. The therapeutic agent of claim 10, wherein the anticancer drug is selected from the group consisting of doxorubicin, platinum, paclitaxel, docetaxel, combretastin A-4, vinblastine, vincristine, vinorelbine, camptothecin, SN-38, etoposide, teniposide, auristatin, calicheamicin, maytansinoid, and duocarmycin.

14. The therapeutic agent of claim 10, wherein $R^1$ comprises an anticancer drug and $R^2$ comprises a folic acid targeting ligand.

15. The therapeutic agent of claim 10 wherein $R^1$ comprises an imaging agent.

16. The therapeutic agent of claim 15, wherein the imaging agent is selected from the group consisting of a Gadolinium (III)-chelate, a Technetium(99m)-chelate, a Gallium-chelate, and a Thallium-chelate.

17. The therapeutic agent of claim 15, wherein the imaging agent is selected from the group consisting of $^{64}Cu$ diacetyl-bis($N^4$-methylthiosemicarbazone), $^{18}F$-fluorodeoxyglucose, 3'-deoxy-3'-($^{18}F$)fluorothymidine, and $^{18}F$-fluoromisonidazole.

18. A method of delivering a therapeutic agent to a cell, comprising contacting the cell with the therapeutic agent of claim 10.

19. The method of claim 18, wherein the contacting is conducted in vitro.

20. The method of claim 18, wherein the contacting is conducted in vivo.

21. A method of treating cancer, comprising identifying a patient in need of cancer treatment and administering a therapeutically effective amount of the therapeutic agent of claim 10 to the patient.

* * * * *